(12) United States Patent
Boku

(10) Patent No.: US 9,078,720 B2
(45) Date of Patent: Jul. 14, 2015

(54) DENTURE SYSTEM, ENGAGEMENT PIECE USED FOR DENTURE SYSTEM, METHOD FOR PRODUCING DENTURE BASE AND DENTURE

(71) Applicant: TUM CORPORATION, Osaka (JP)

(72) Inventor: Nariyuki Boku, Osaka (JP)

(73) Assignee: TUM Corporation, Osaka (JP)

( * ) Notice: Subject to any disclaimer, the term of this patent is extended or adjusted under 35 U.S.C. 154(b) by 0 days.

(21) Appl. No.: 14/035,280

(22) Filed: Sep. 24, 2013

(65) Prior Publication Data
US 2014/0023989 A1    Jan. 23, 2014

Related U.S. Application Data

(63) Continuation-in-part of application No. PCT/JP2012/055961, filed on Mar. 8, 2012.

(30) Foreign Application Priority Data

Mar. 28, 2011 (JP) .................................. 2011-069282
Jun. 29, 2011 (JP) .................................. 2011-144112
Sep. 14, 2011 (WO) .................. PCT/JP2011/070933

(51) Int. Cl.
*A61C 8/00* (2006.01)
*A61C 13/265* (2006.01)
(Continued)

(52) U.S. Cl.
CPC ............. *A61C 8/0062* (2013.01); *A61C 8/0001* (2013.01); *A61C 8/0048* (2013.01);
(Continued)

(58) Field of Classification Search
CPC .. A61C 8/0001; A61C 8/0048; A61C 8/0062; A61C 8/0082; A61C 13/2656; A61C 13/04; A61C 13/081

USPC .................................. 433/171, 172, 173, 177
See application file for complete search history.

(56) References Cited

U.S. PATENT DOCUMENTS 4,215,986 A      8/1980   Riess
4,540,367 A  *   9/1985   Sulc .............................. 433/181
(Continued)

FOREIGN PATENT DOCUMENTS

DE        4127436 A1    3/1992
EP     0 896 812 A1    2/1999
(Continued)

OTHER PUBLICATIONS

International Search Report for corresponding International Application No. PCT/JP2012/055961 mailed Apr. 10, 2012.
(Continued)

*Primary Examiner* — Ralph Lewis
(74) *Attorney, Agent, or Firm* — Renner, Otto, Boisselle & Sklar, LLP

(57) ABSTRACT

A denture system comprising: abutments coupled to the fixtures; and a denture to be detachably attached to the abutments, the denture including: a denture base; an artificial tooth supported by the denture base; a plurality of engagement piece members defining slits extending in the up-down direction; and a lid portion connecting end portions of the engagement piece members as well as closing one end of fitting hole in the up-down direction and covering an entire surface of the tip of the abutment, wherein the lid portion configures a part of the denture base, the piece member has a first surface and a second surface, and a grooved allowance portion is provided allowing the piece member to deform and spread in direction from the first surface toward the second surface.

6 Claims, 66 Drawing Sheets

(51) Int. Cl.
*A61C 13/01* (2006.01)
*A61C 13/08* (2006.01)
*A61K 6/08* (2006.01)

(52) U.S. Cl.
CPC .............. *A61C 13/04* (2013.01); *A61C 13/081* (2013.01); *A61C 13/2656* (2013.01); *A61K 6/08* (2013.01); *A61C 8/0086* (2013.01)

(56) References Cited

U.S. PATENT DOCUMENTS

| | | | |
|---|---|---|---|
| 5,098,295 A | 3/1992 | Dürr et al. | |
| 5,417,570 A * | 5/1995 | Zuest et al. | 433/177 |
| 5,556,280 A | 9/1996 | Pelak | |
| 5,564,928 A | 10/1996 | Gittleman | |
| 5,678,997 A * | 10/1997 | De Buck | 433/177 |
| 5,947,733 A | 9/1999 | Sutter et al. | |
| 5,997,300 A * | 12/1999 | Tseng | 433/177 |
| 6,030,219 A * | 2/2000 | Zuest et al. | 433/181 |
| 6,190,169 B1 * | 2/2001 | Bluemli et al. | 433/172 |
| 6,332,777 B1 * | 12/2001 | Sutter | 433/173 |
| 7,704,076 B2 * | 4/2010 | Mullaly et al. | 433/174 |
| 7,959,439 B2 * | 6/2011 | Bulloch et al. | 433/173 |
| 2004/0166476 A1 | 8/2004 | Weissman | |
| 2008/0176186 A1 | 7/2008 | Schaub | |
| 2009/0263763 A1 * | 10/2009 | Shepard | 433/174 |
| 2010/0112520 A1 | 5/2010 | Worthington | |
| 2012/0315599 A1 * | 12/2012 | Mullaly | 433/173 |

FOREIGN PATENT DOCUMENTS

| | | |
|---|---|---|
| EP | 1 627 612 A1 | 2/2006 |
| JP | 55-10979 A | 1/1980 |
| JP | 3-54 | 7/1991 |
| JP | 05-293123 A | 11/1993 |
| JP | 11-104150 A | 4/1999 |
| JP | 11-506688 A | 6/1999 |
| JP | 2000-512884 | 10/2000 |
| JP | 2000-512884 A | 10/2000 |
| JP | 2006-512179 A | 4/2006 |
| WO | WO 2005/115270 A1 | 12/2005 |

OTHER PUBLICATIONS

International Search Report in corresponding Japanese Patent Application No. PCT/JP2014/072720 dated Dec. 2, 2014.

* cited by examiner

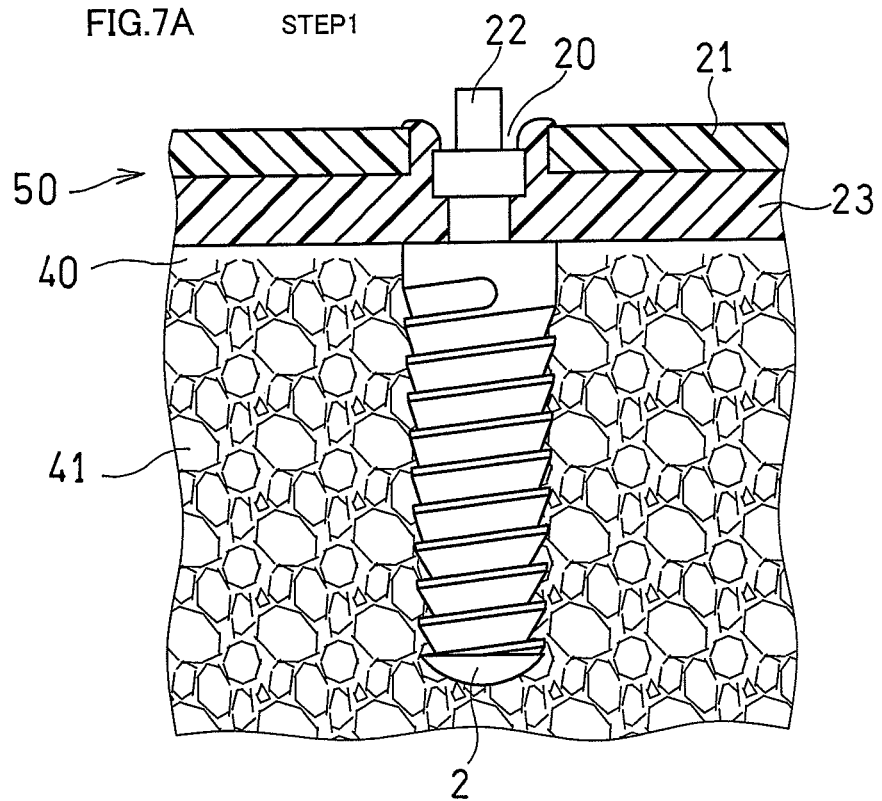
FIG.7A STEP1
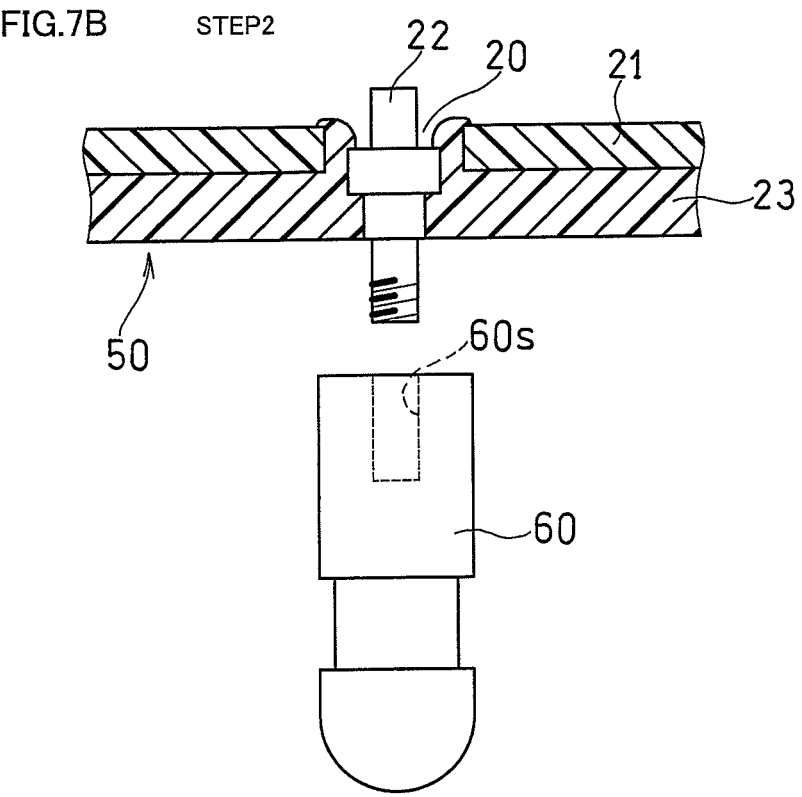
FIG.7B STEP2

STEP3

STEP4

STEP5

STEP6

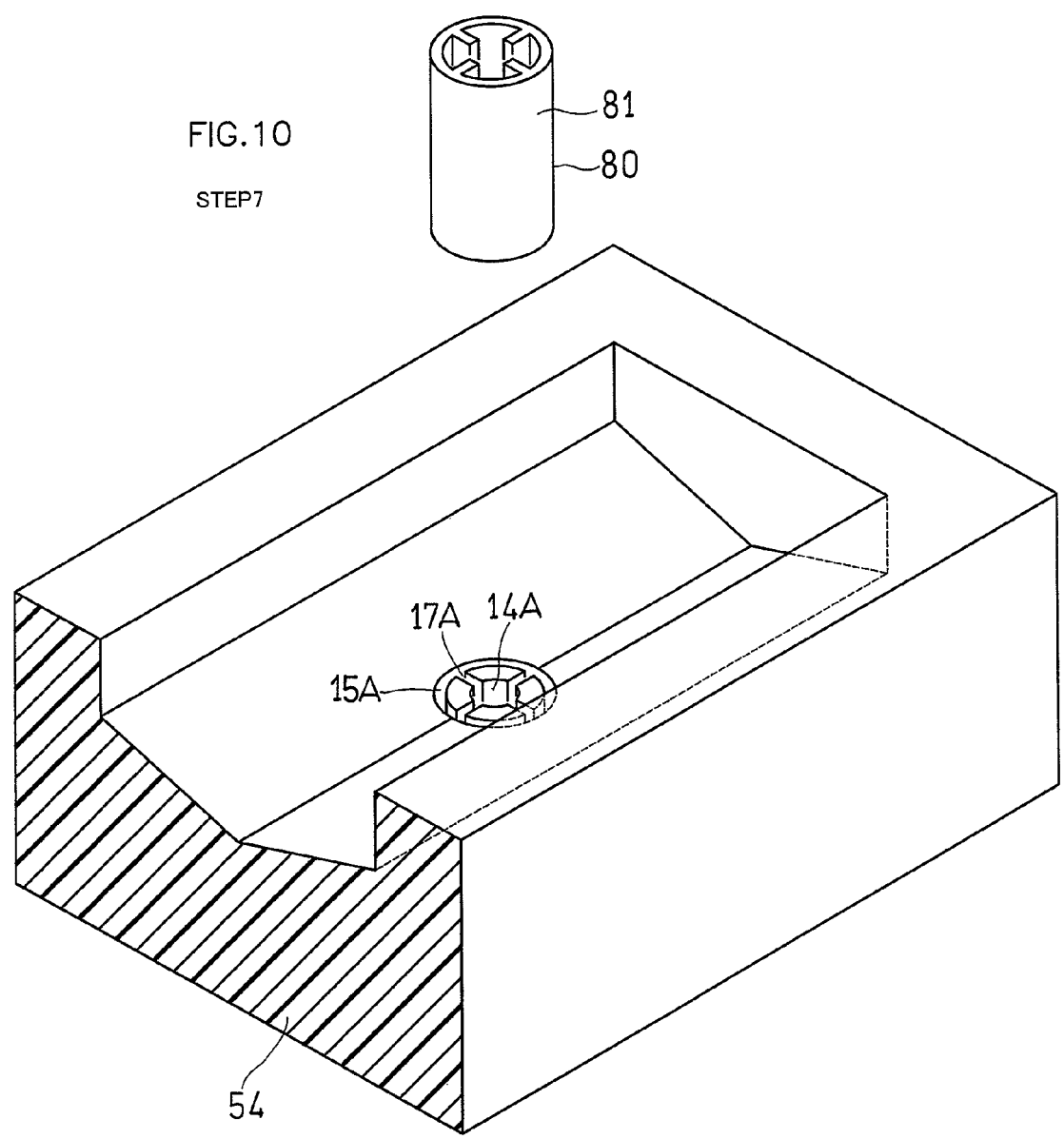

STEP8

STEP9

STEP10

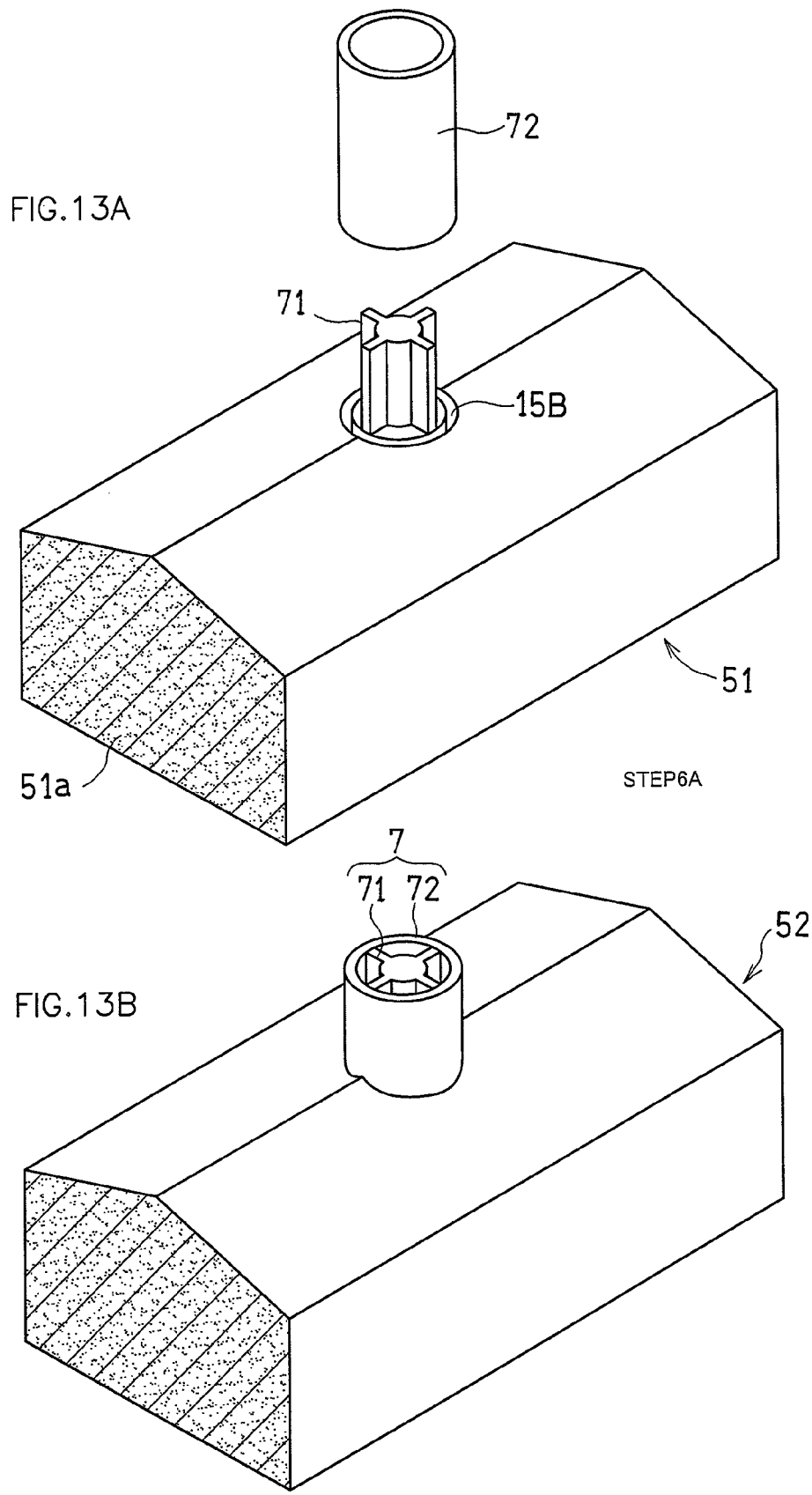

STEP11

STEP12

STEP13

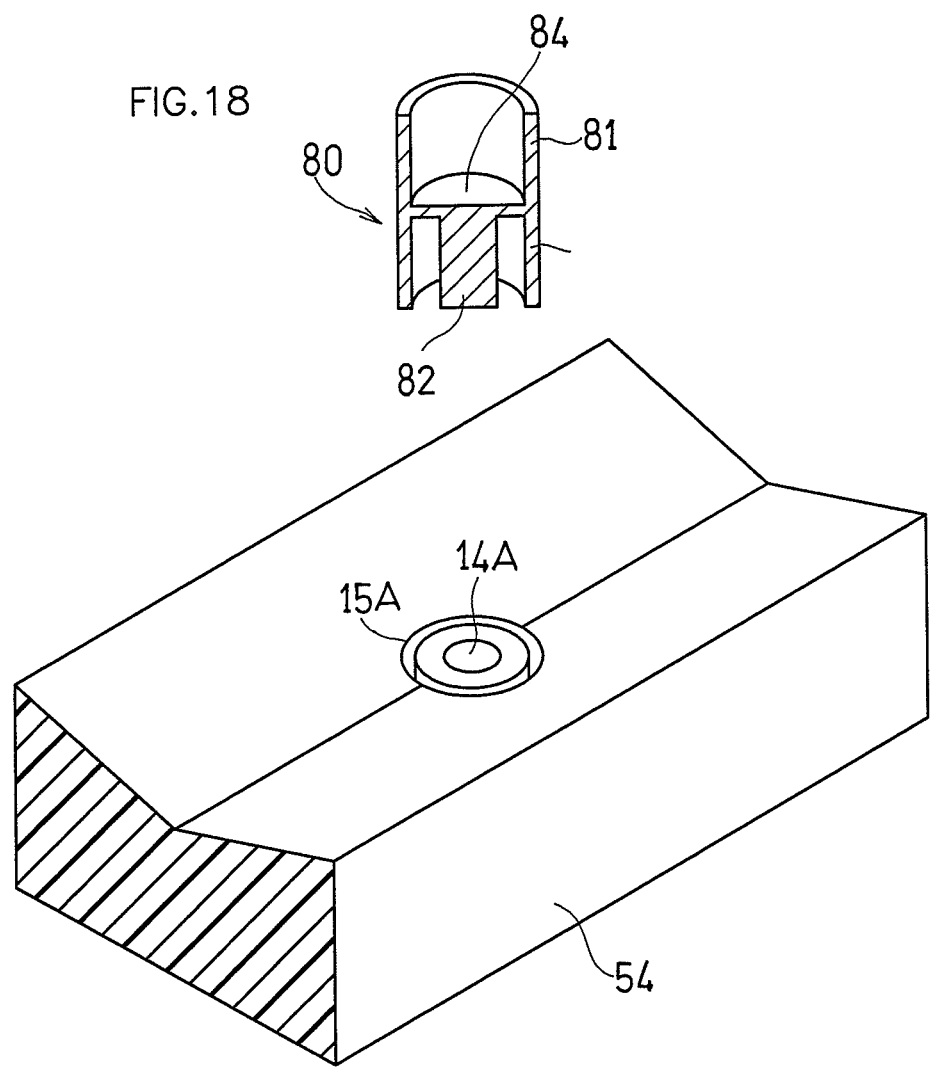

STEP2

STEP1

STEP34

STEP3

STEP35

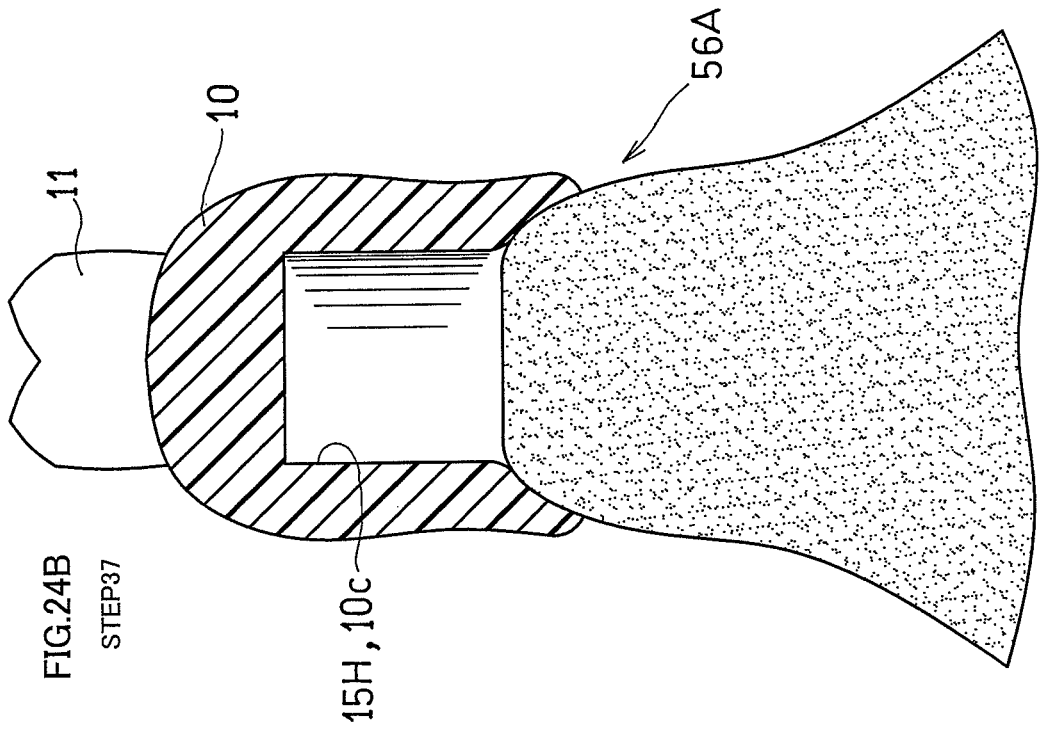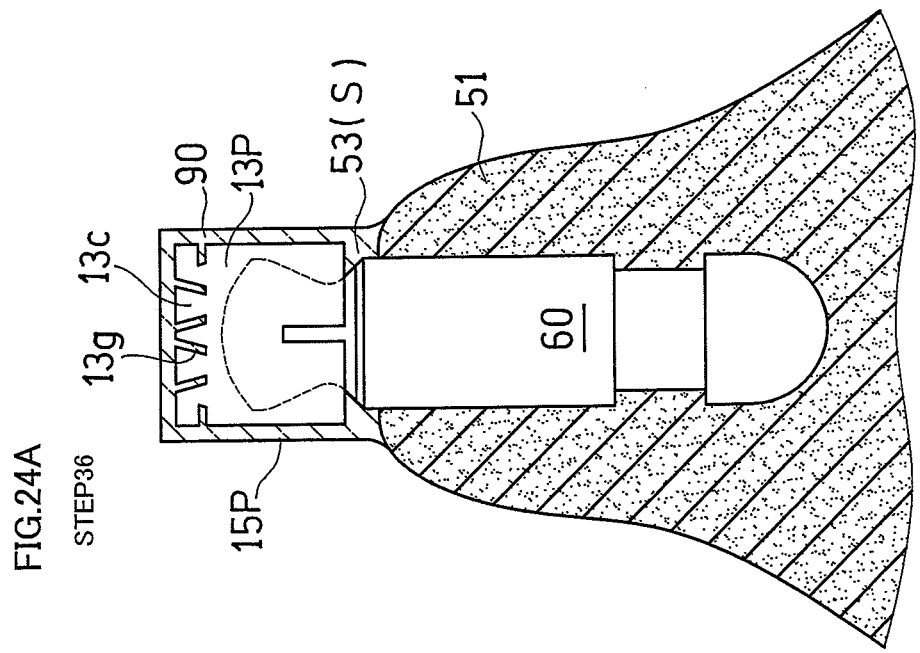

STEP39

STEP38

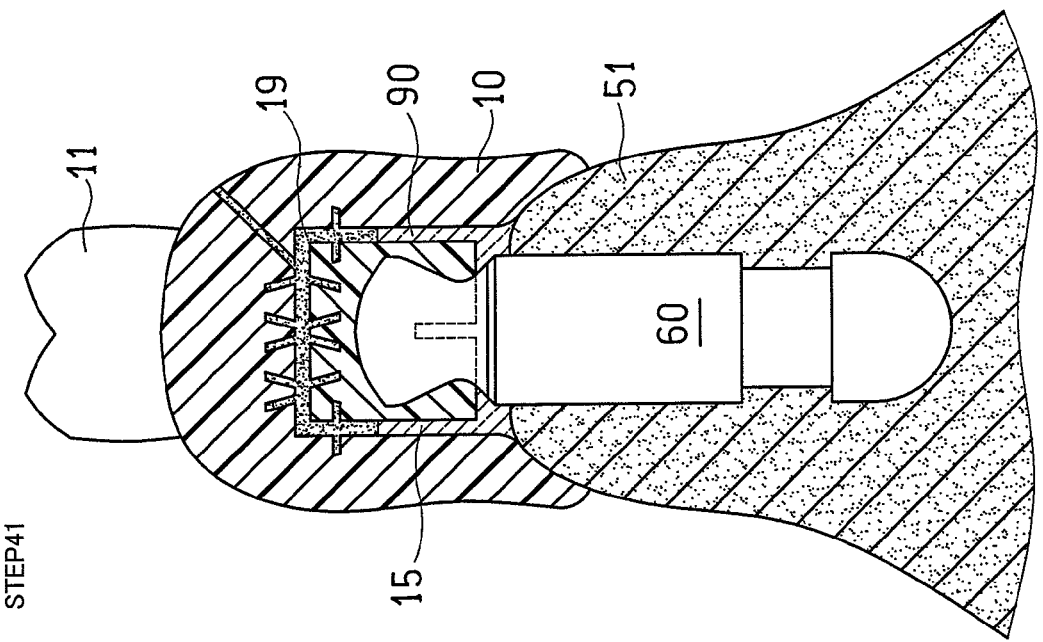
FIG.26A STEP40
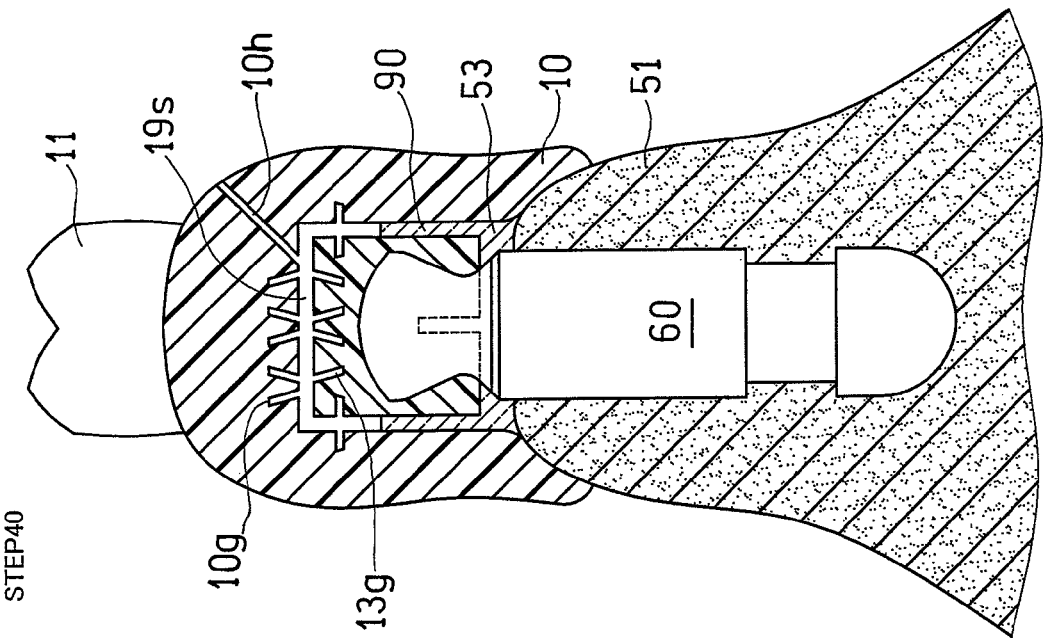
FIG.26B STEP41

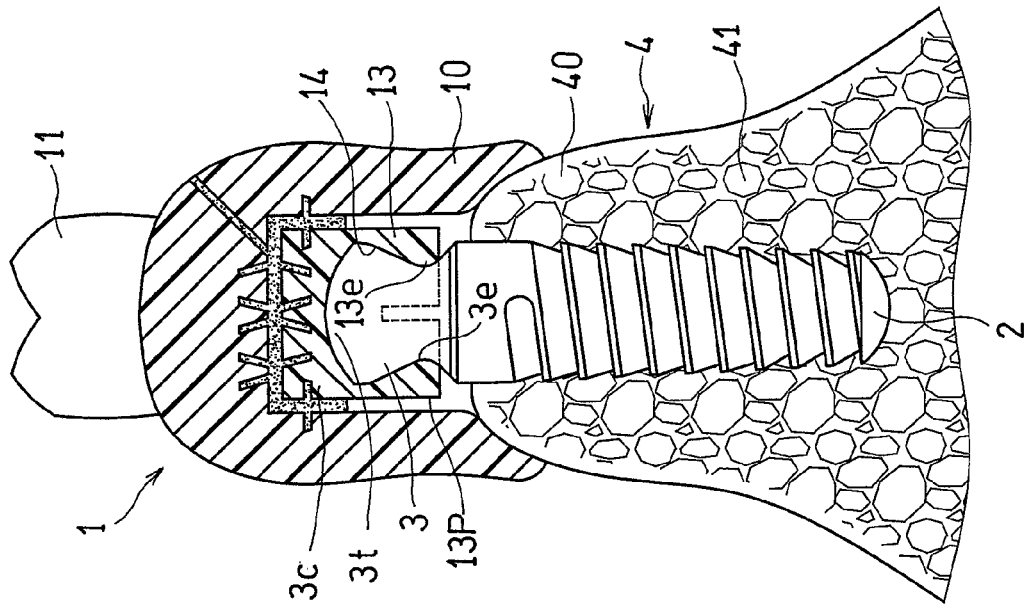
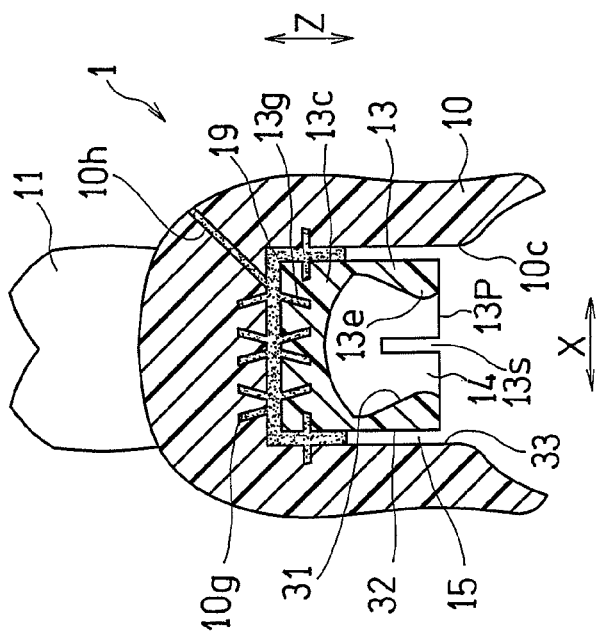
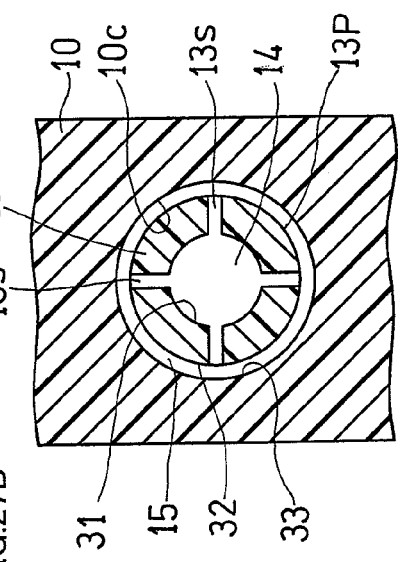

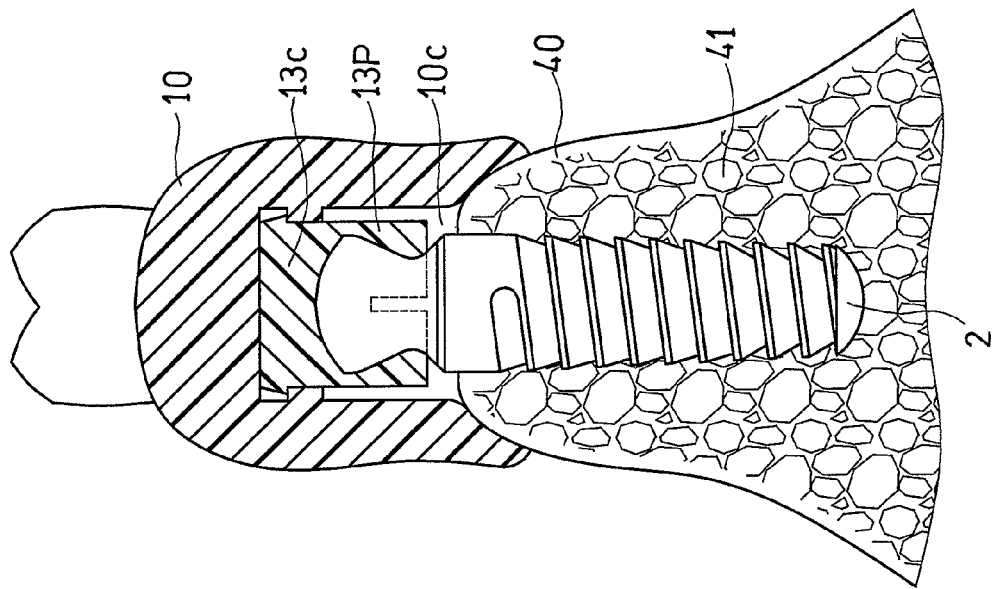
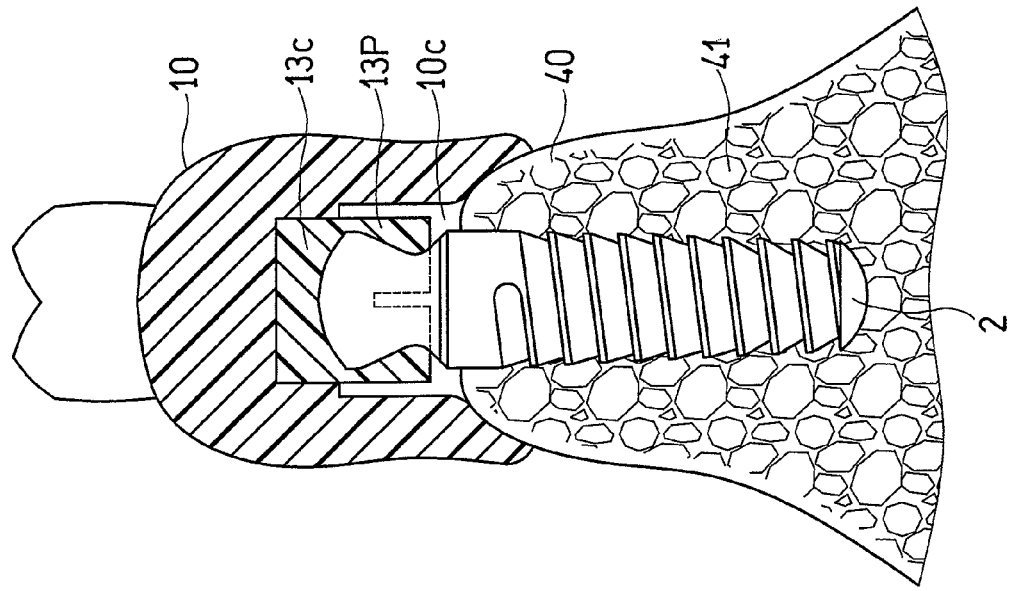

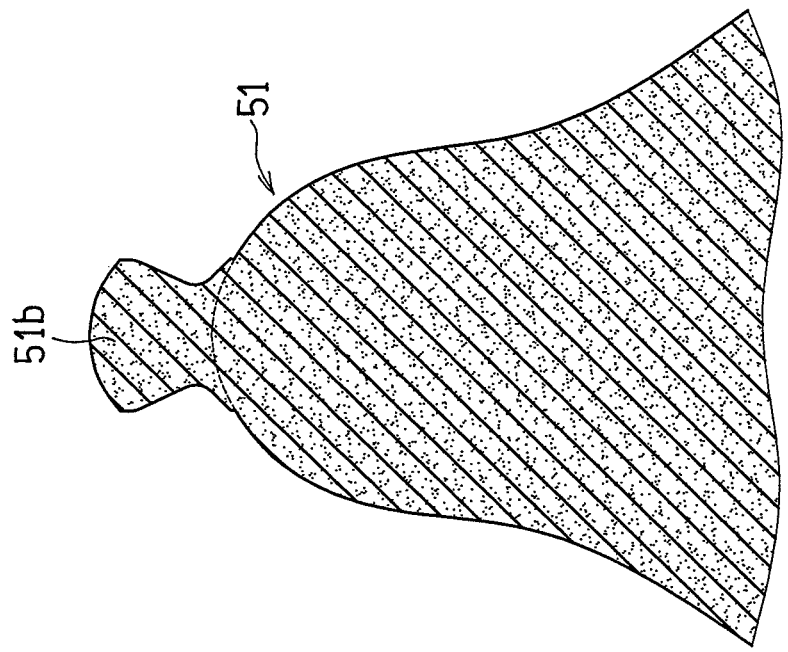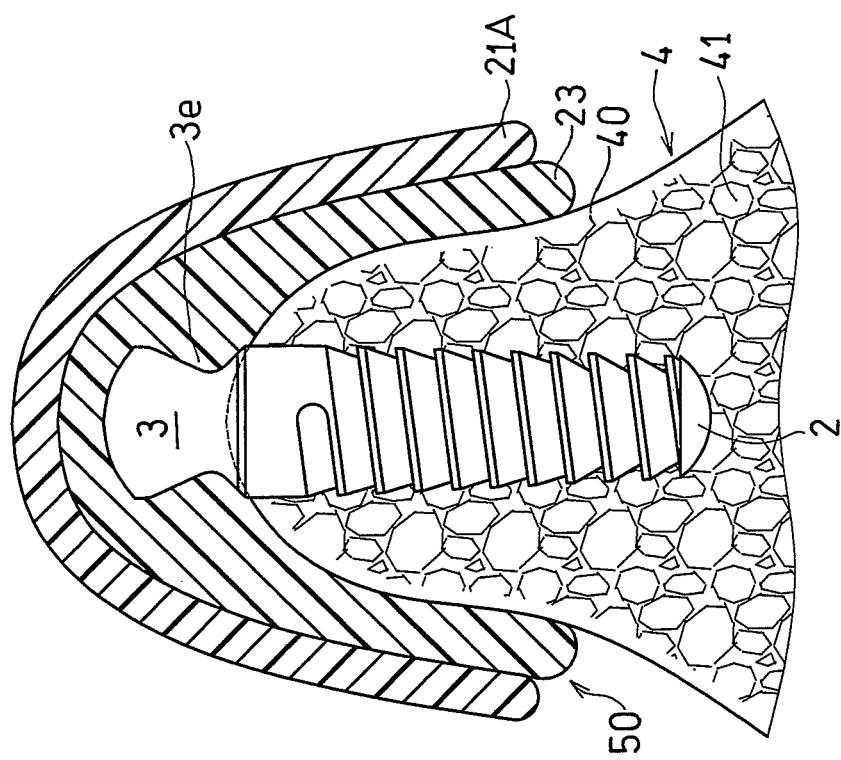
FIG.31A STEP51
FIG.31B STEP52

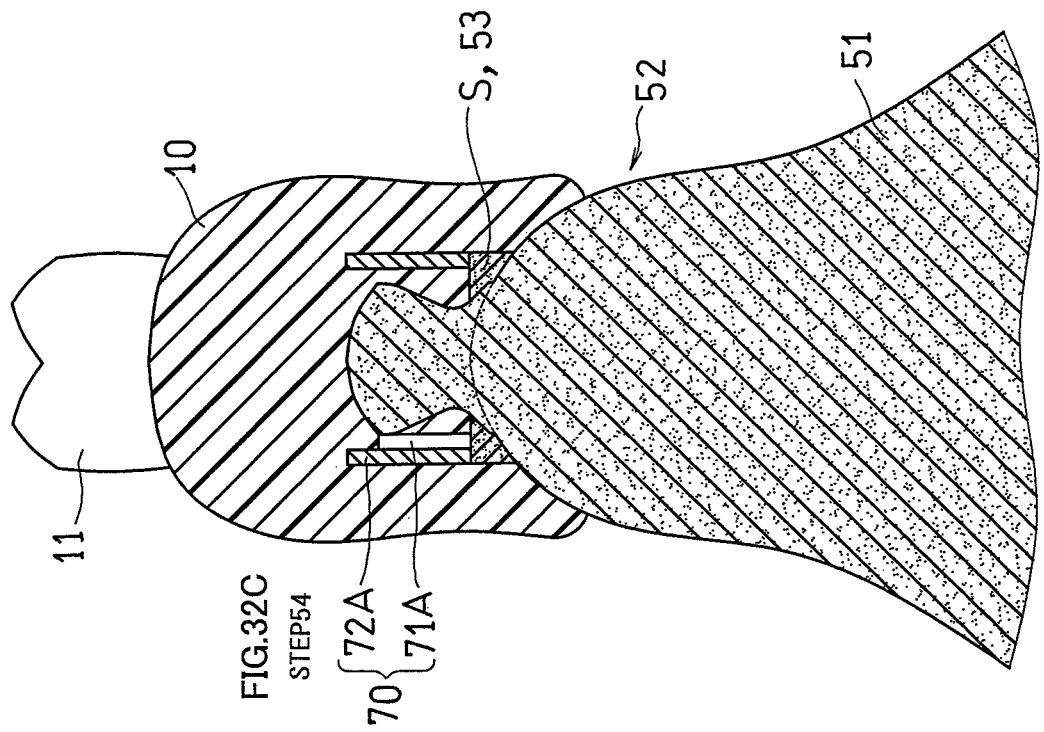
FIG.32C STEP54
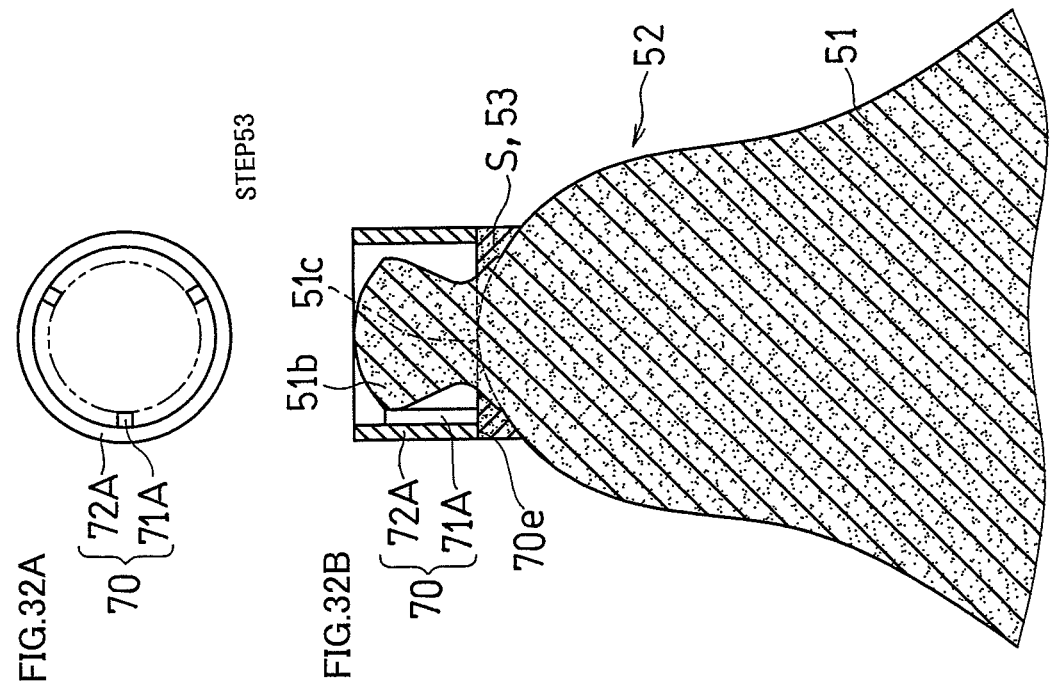
FIG.32A
FIG.32B STEP53

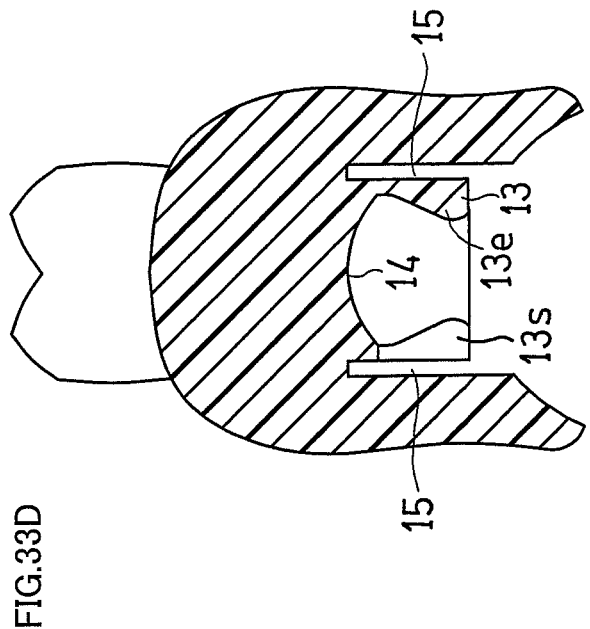
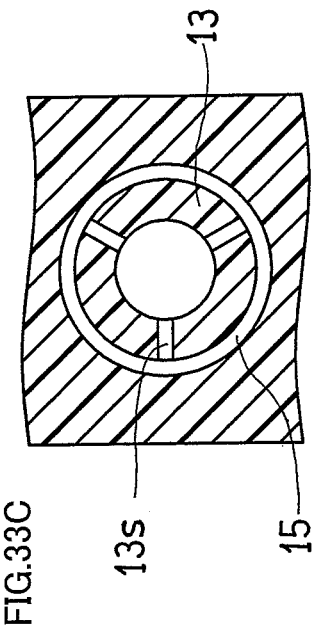
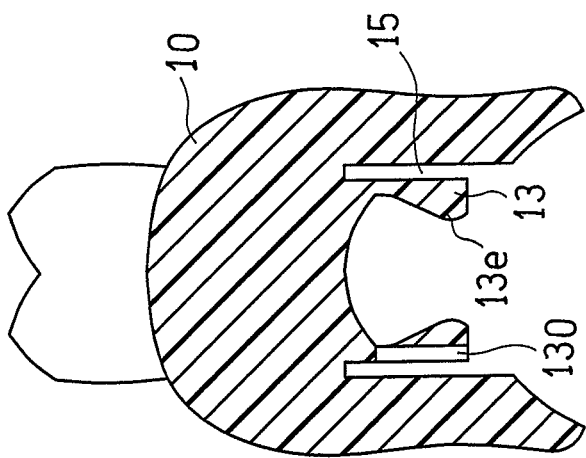
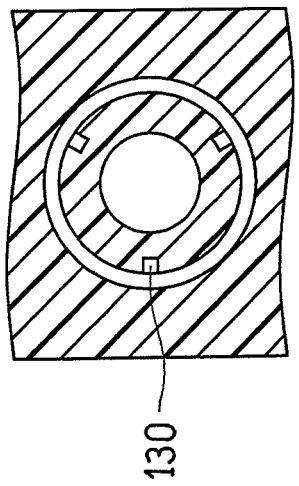

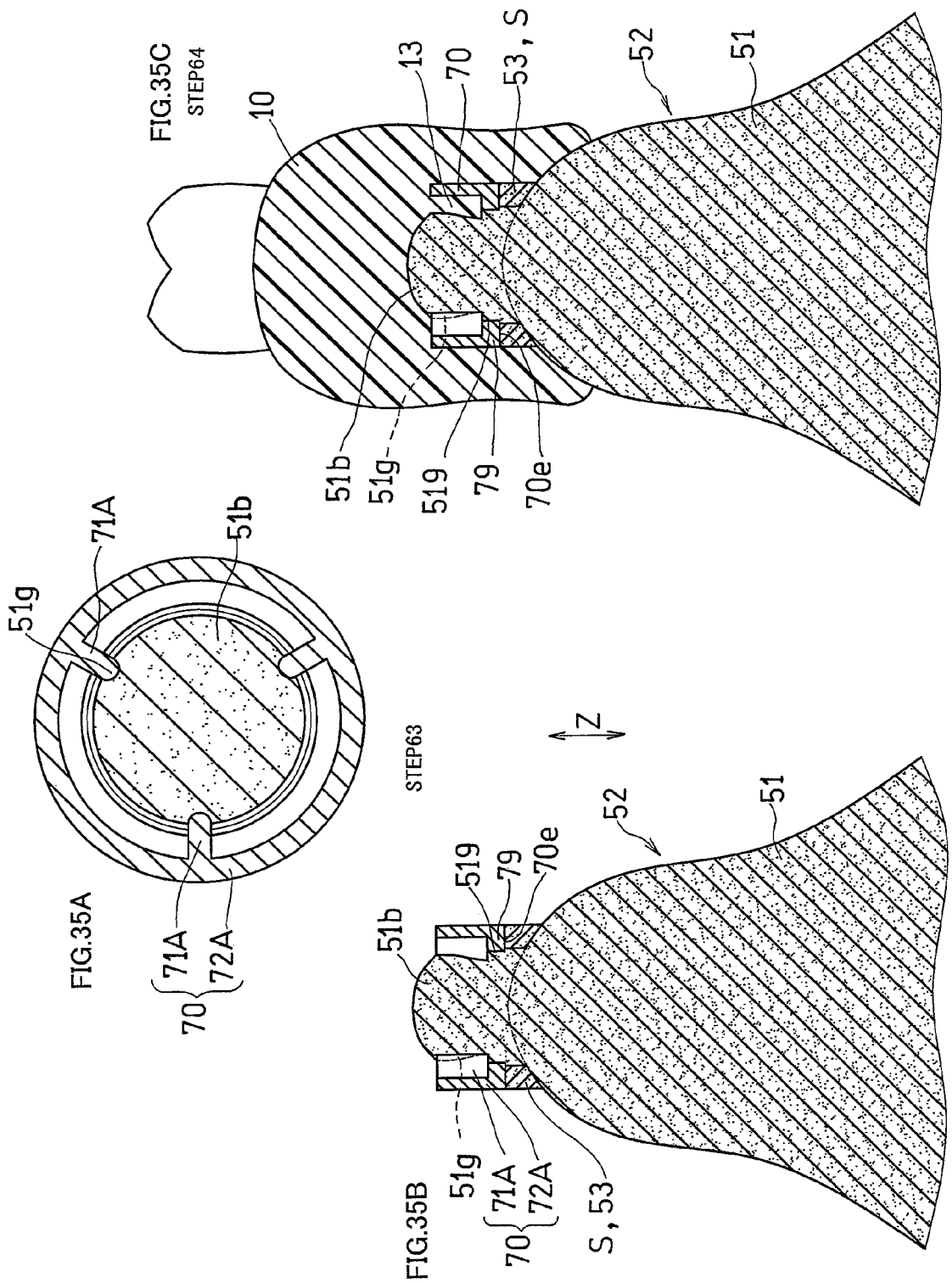

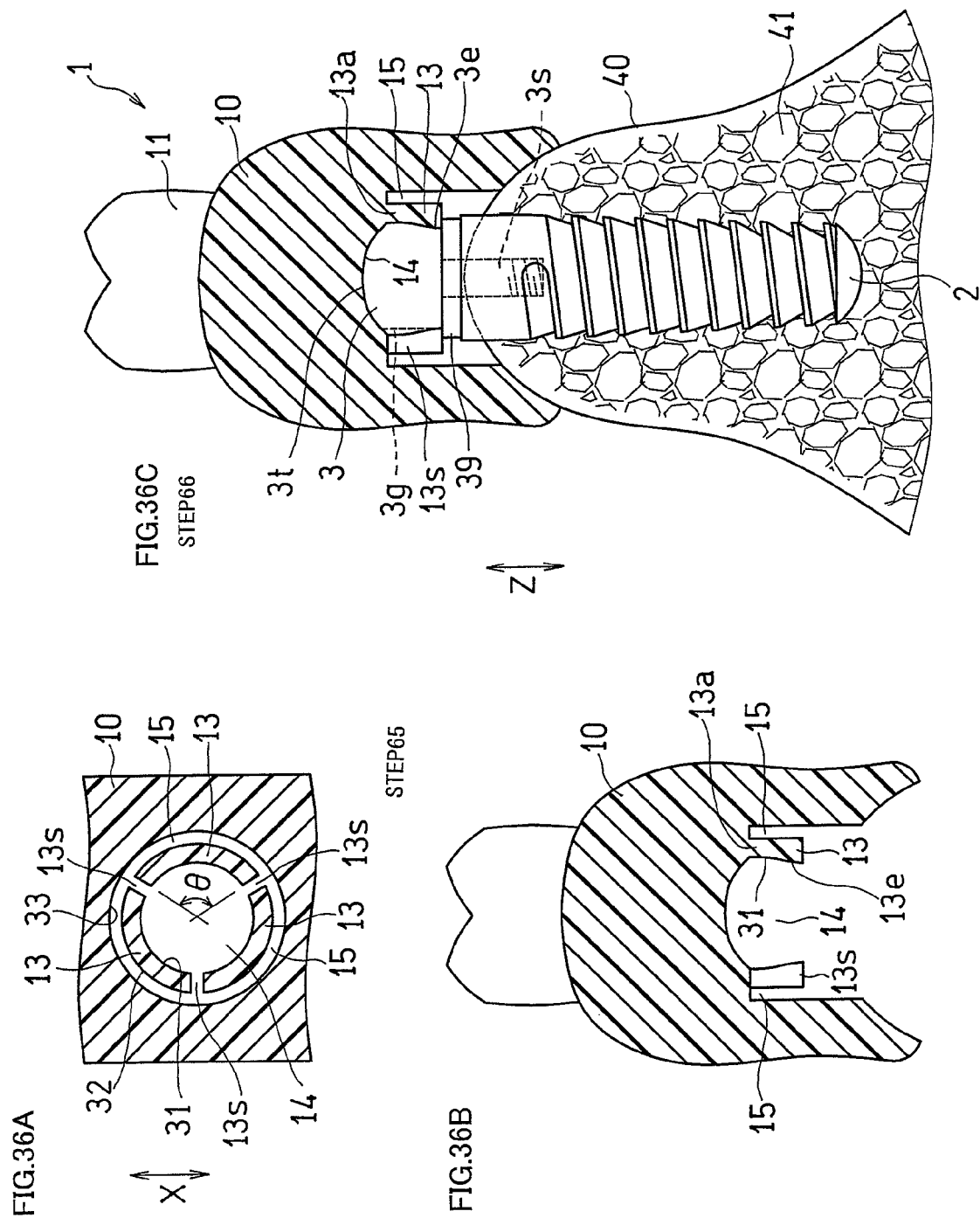

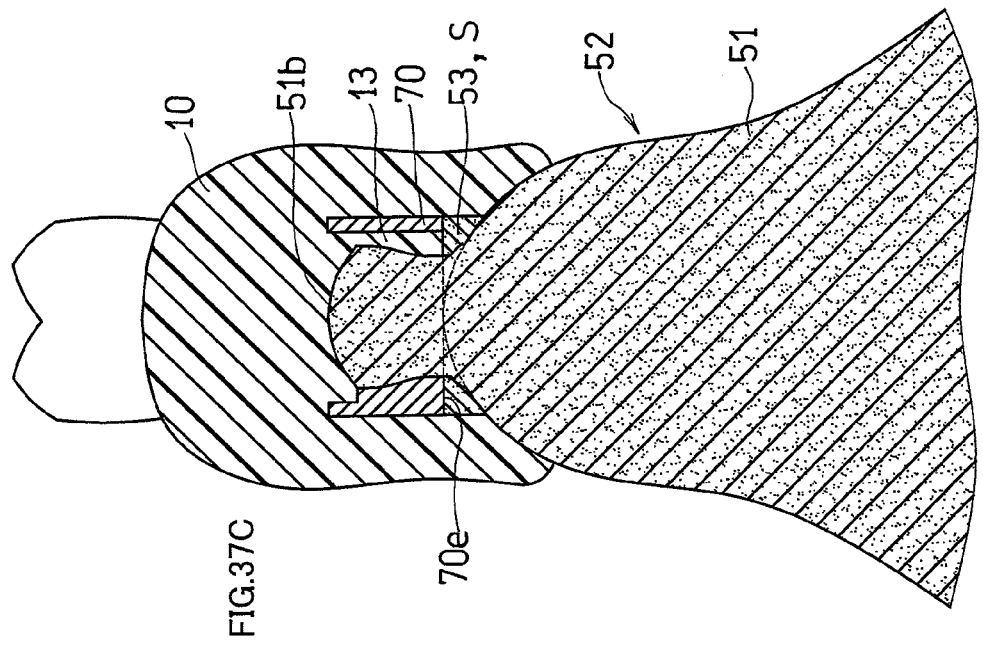
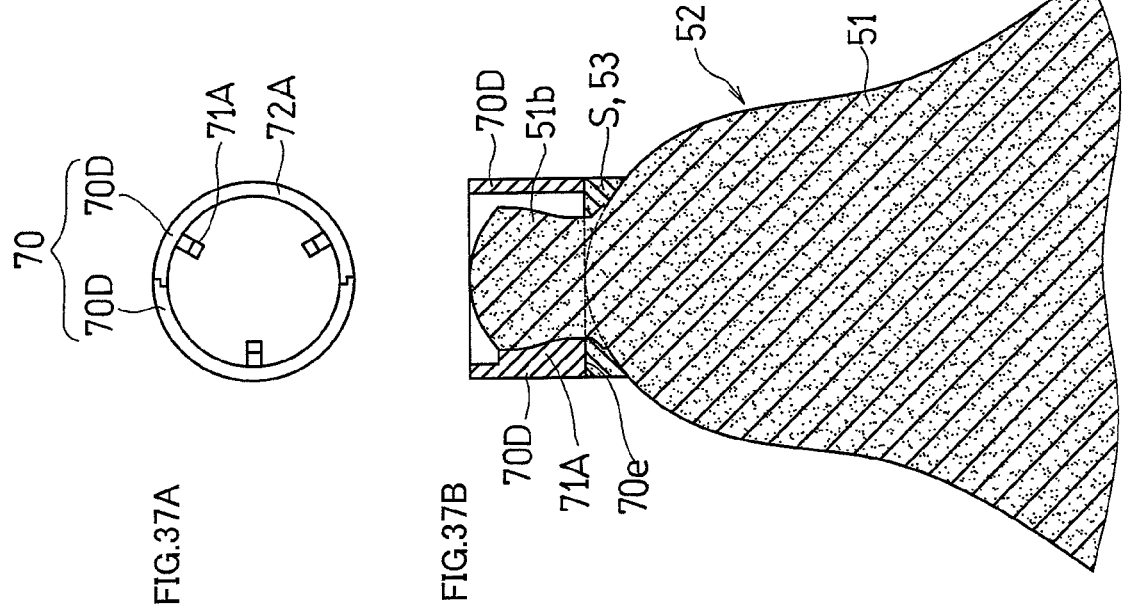

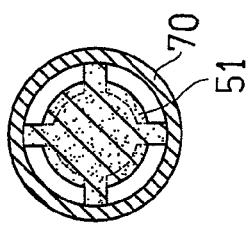
FIG.41A
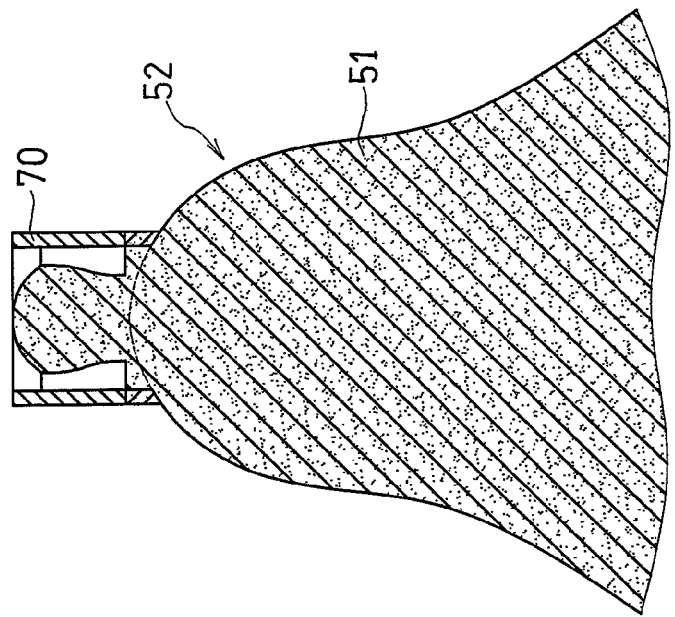
FIG.41C
FIG.41D
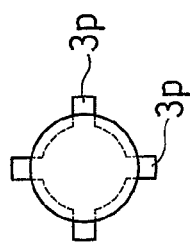
FIG.41B
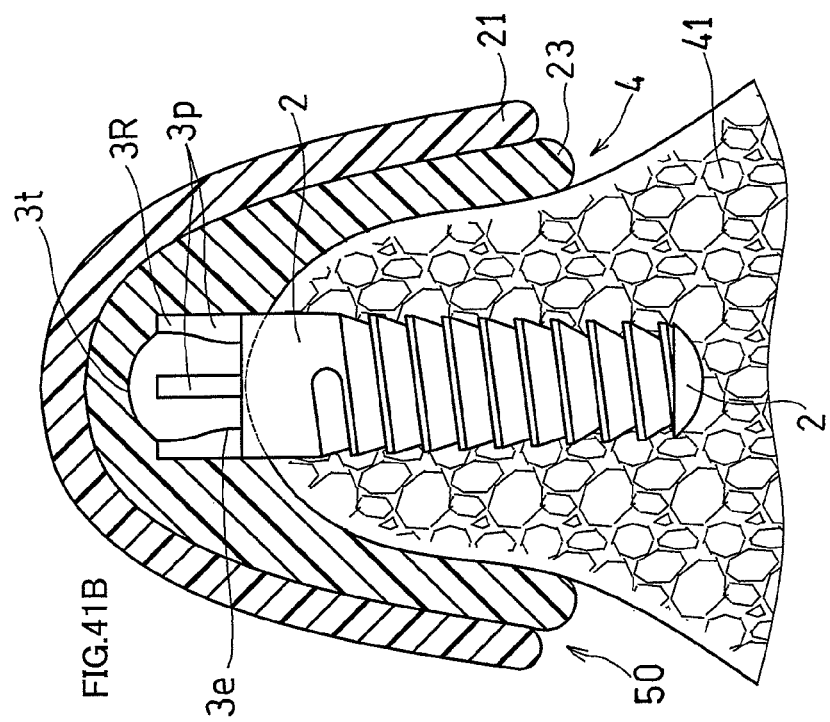

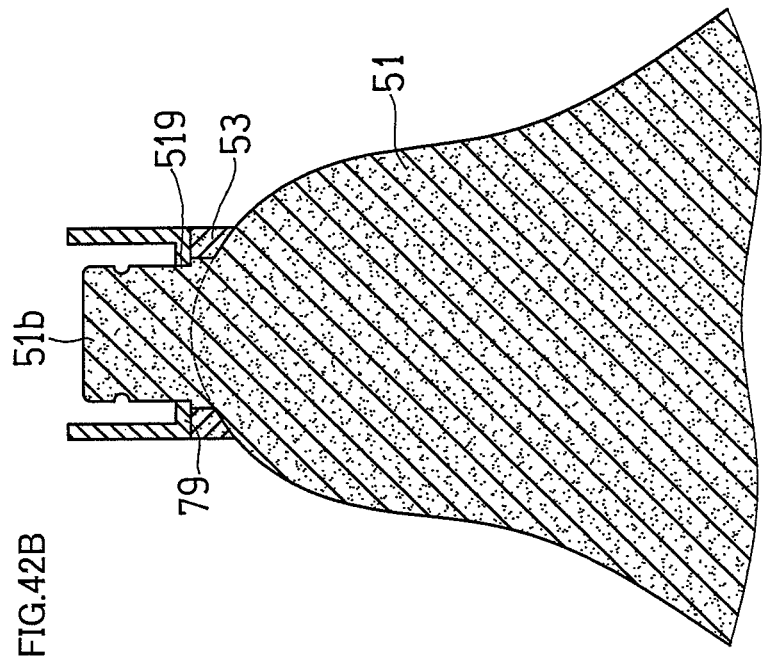
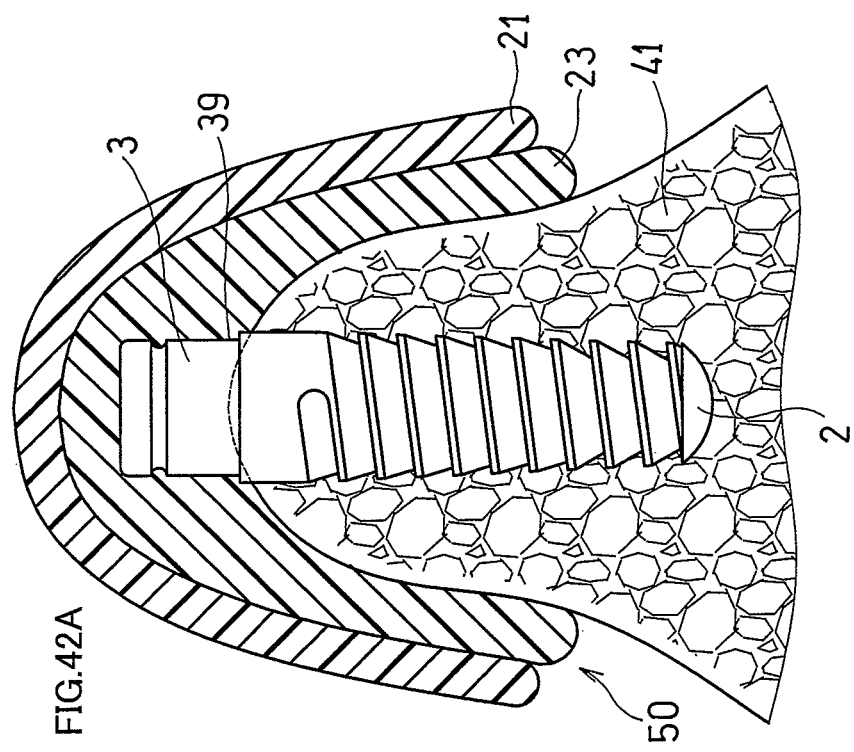

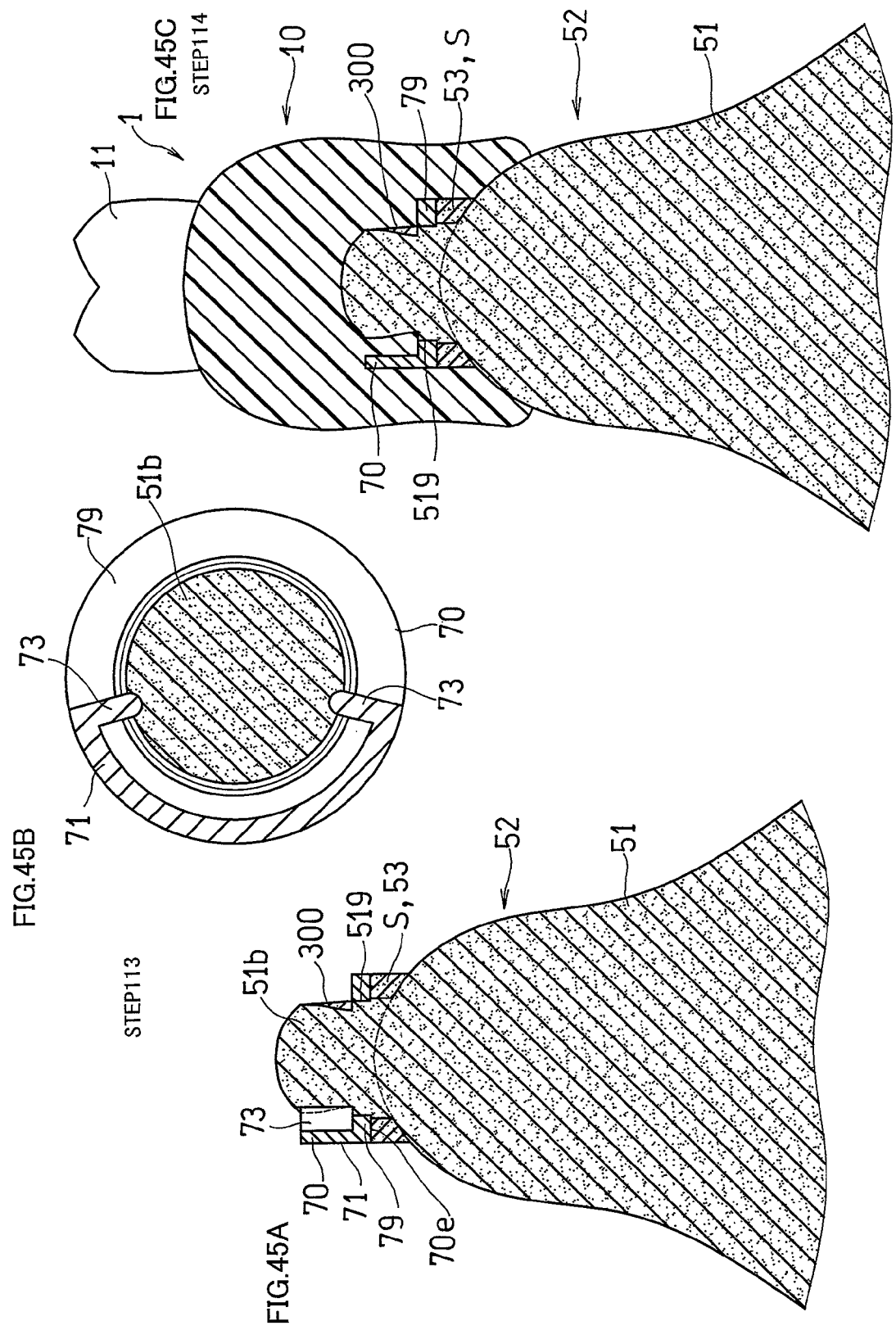

STEP115

STEP116

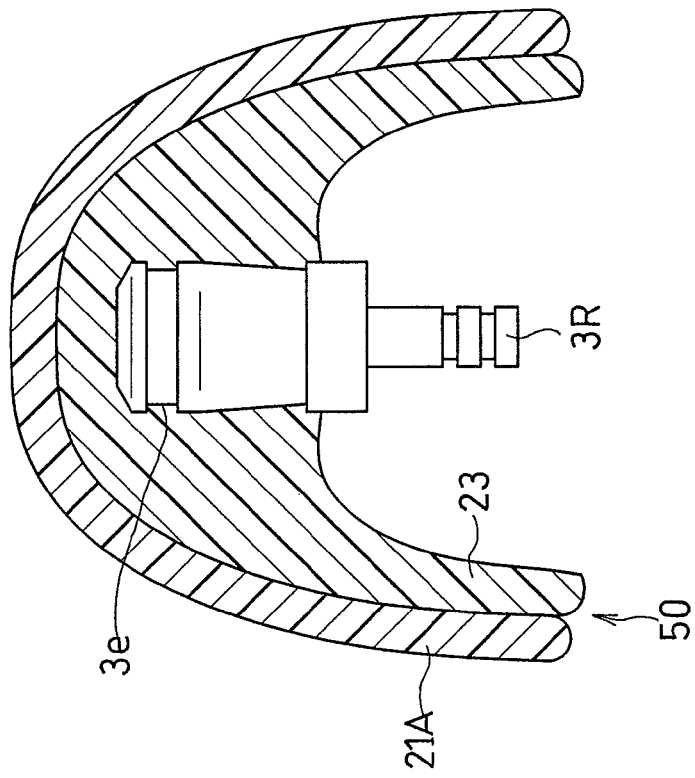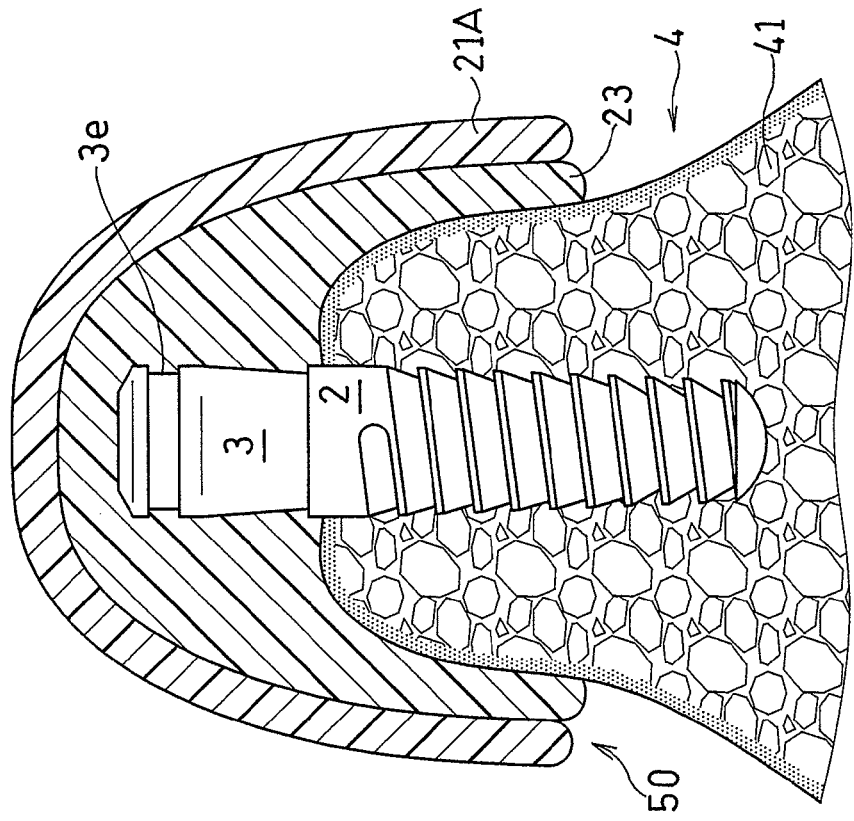

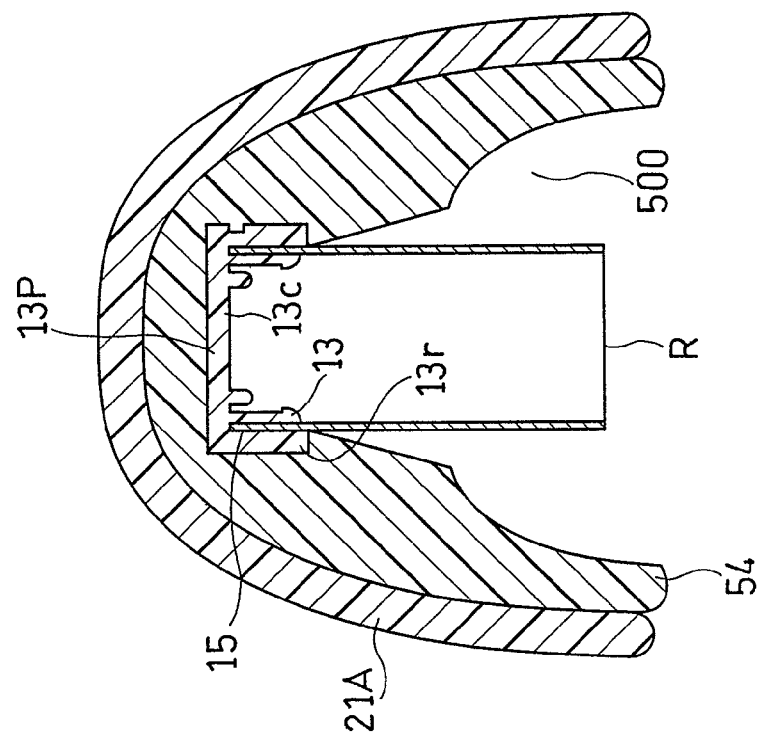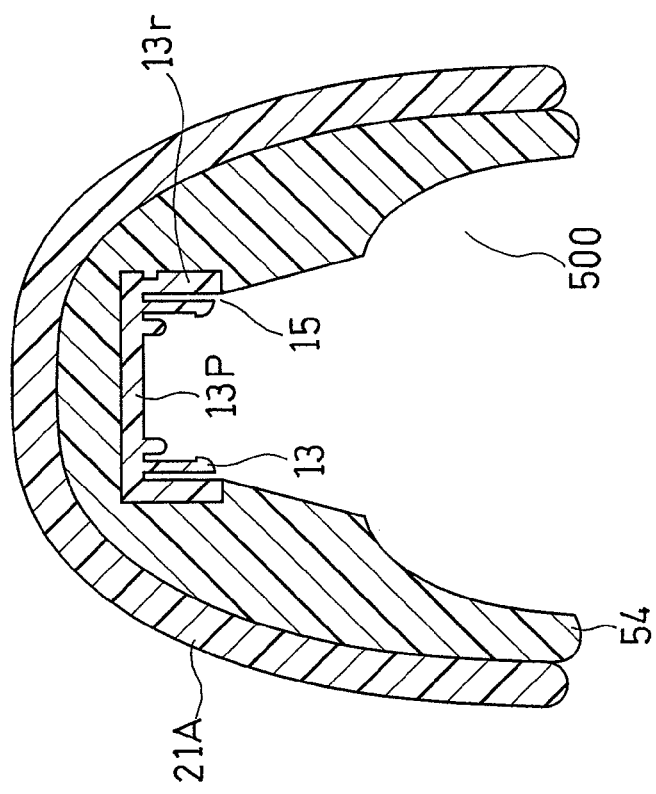

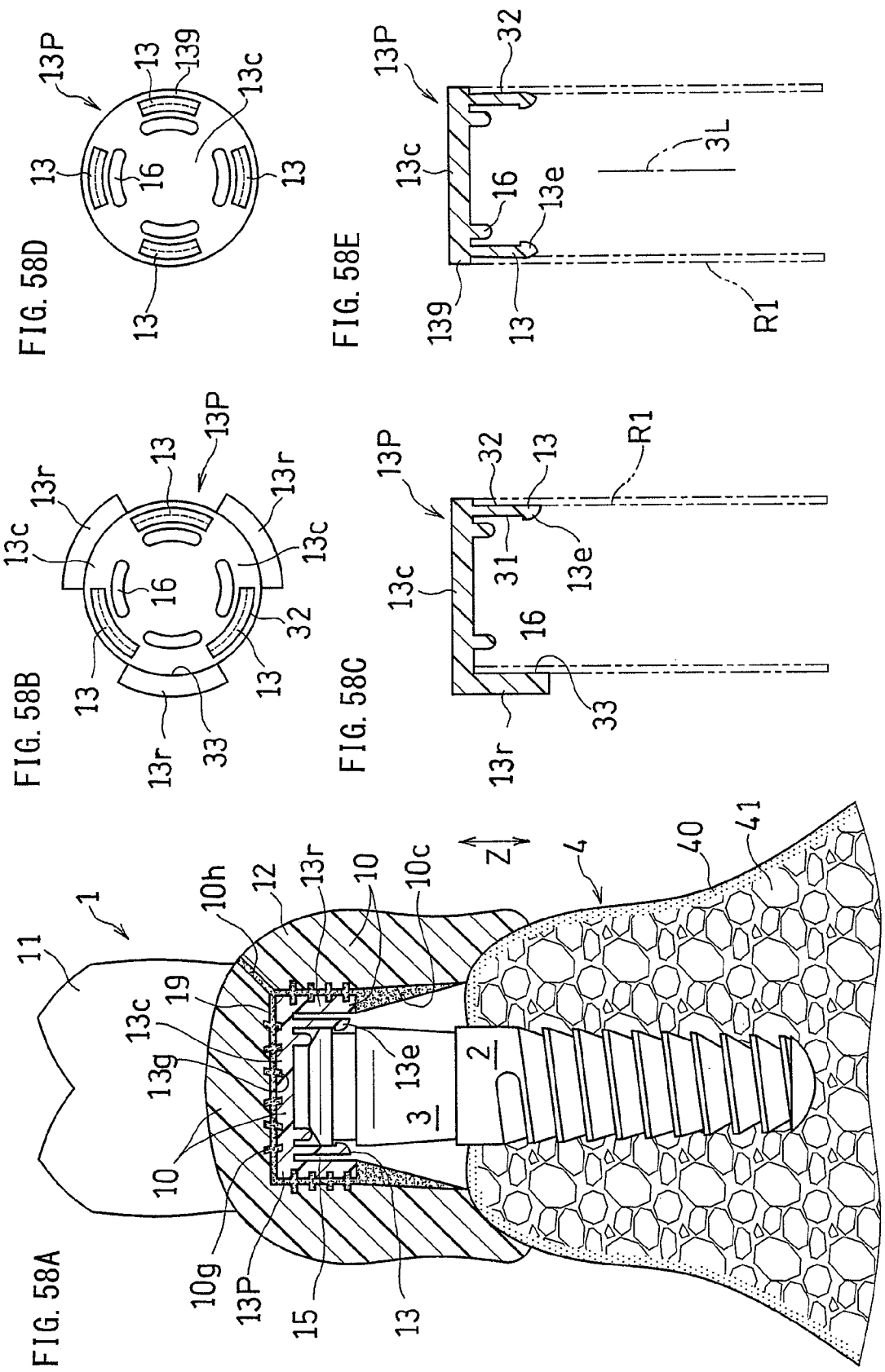

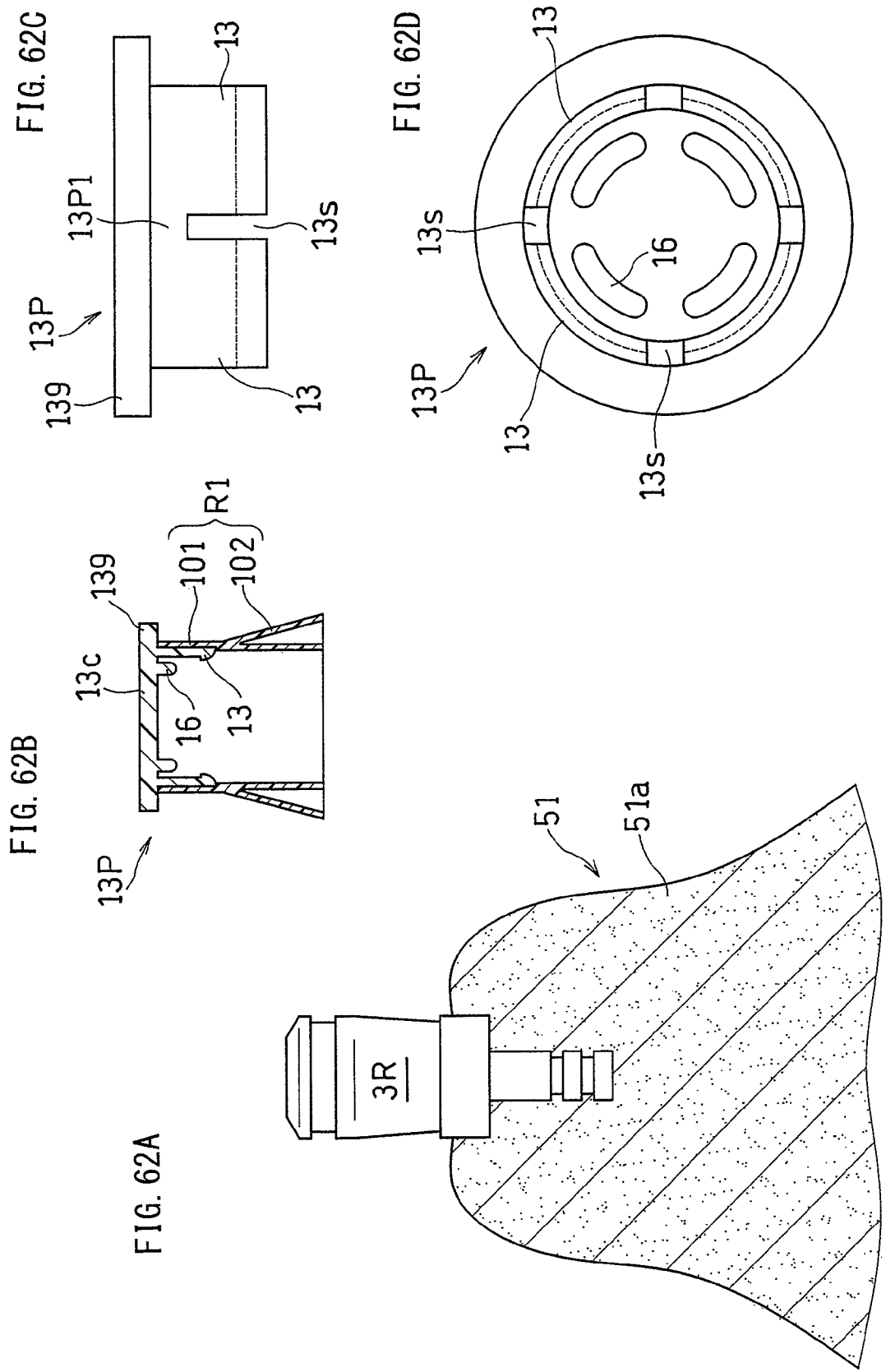

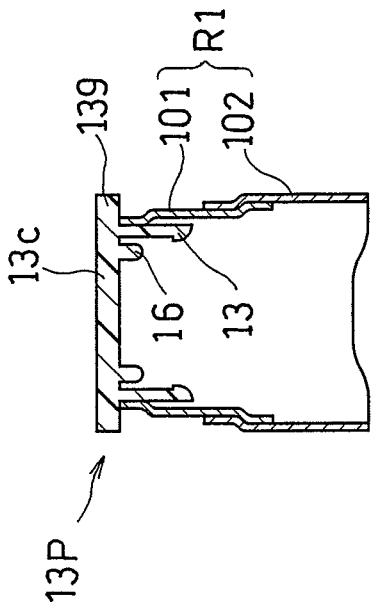
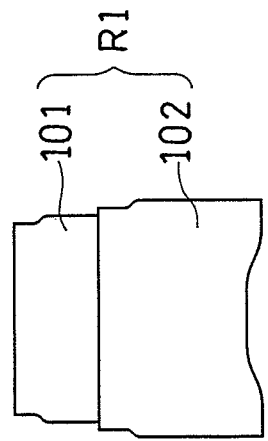
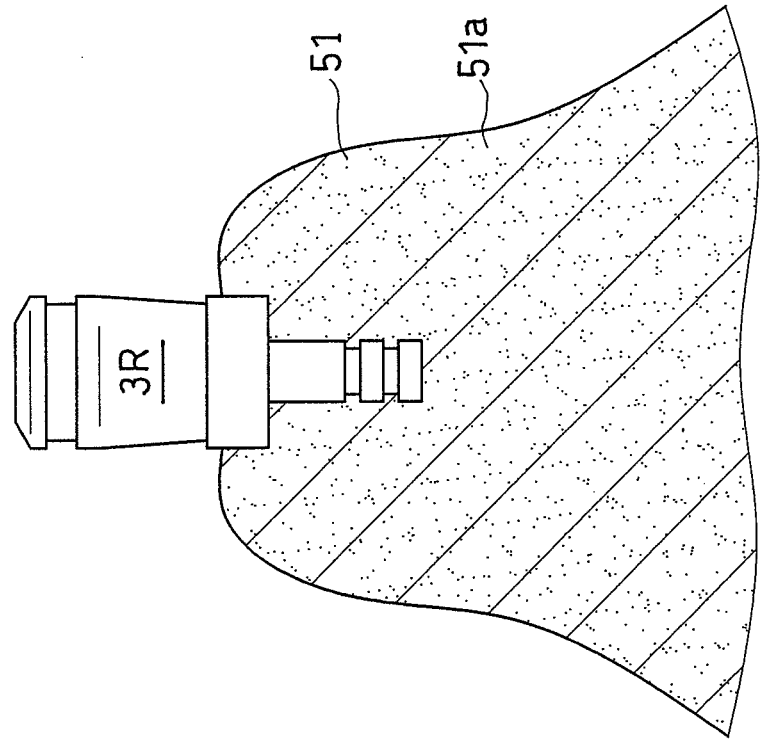

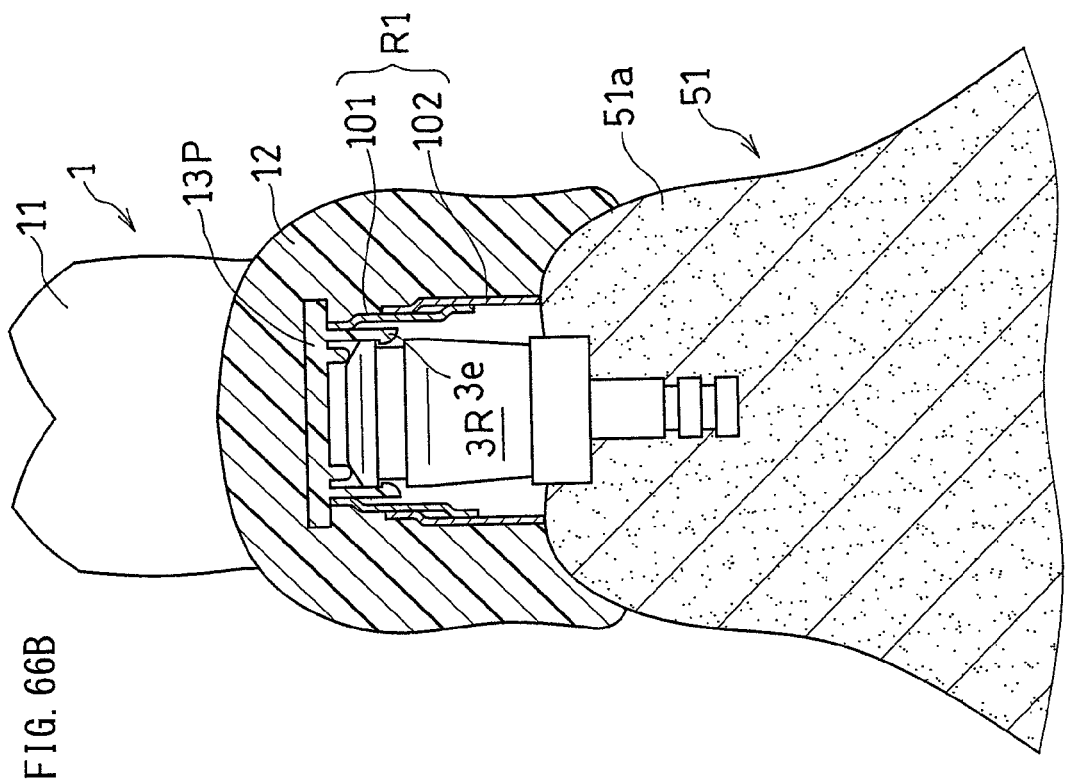
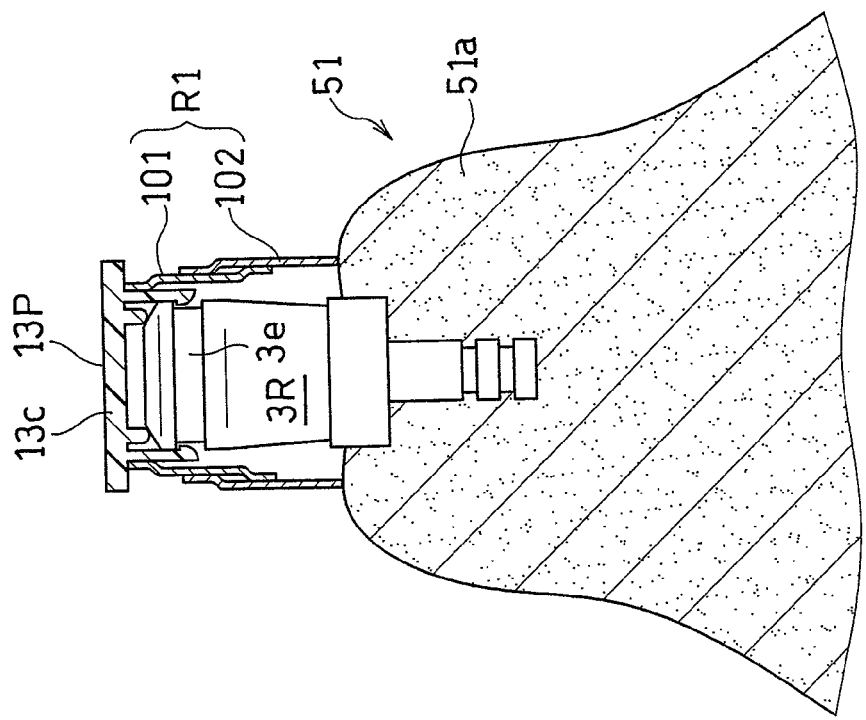

DENTURE SYSTEM, ENGAGEMENT PIECE USED FOR DENTURE SYSTEM, METHOD FOR PRODUCING DENTURE BASE AND DENTURE

CROSS-REFERENCE TO RELATED APPLICATIONS

This application is a continuation in part of the PCT international application No. PCT/JP2012/55961 filed on Mar. 8, 2012, which claims the priority based on the following applications. The entire contents of all these applications are hereby incorporated herein by reference.
(1) Patent application number: JP2011-069282; Application date: Mar. 28, 2011
(2) Patent application number: JP2011-144112; Application date: Jun. 29, 2011
(3) International application number: PCT/JP2011/070933; International filing date: Sep. 14, 2011

TECHNICAL FIELD

The present invention relates to a denture system and dentures.

BACKGROUND ART

In recent years, denture systems so called "implants" are beginning to employ a structure including one or more fixtures (implant bodies), and a number of artificial teeth greater than the number of fixtures. With such a system, the number of fixtures can be reduced, thereby reducing the physical and economic burden on the patient.

On the other hand, in a system of this type, a denture including a denture base and artificial teeth is detachably attached to an abutment fixed to a fixture. (the first patent document)

CITATION LIST

Patent Literature

[First Patent Document] JP2006-512179 (Abstract)

SUMMARY OF INVENTION

However, the conventional technique requires a step of finishing the denture by filling an area to be the denture base with a resin, with a semi-finished product (unfinished) denture, which has been obtained by taking an impression and molding, attached to the abutment. This step may increase the physical/time burden on the patient and the dentist and the cost.

This problem will be described in detail.

Impression materials used when taking an impression of the oral cavity and plasters, which are materials of male molds produced from the impression materials, have very little shrinkage when set. On the other hand, with conventional techniques, a hook attached to the abutment is firmly fitted to the abutment with no gap therebetween.

Therefore, even if materials have little shrinkage, it will not be possible to prevent the hook from giving an external force onto a plurality of abutments spaced apart from one another. Such an external force may deteriorate the fit and may also apply a load on the fixture.

Therefore, as described above, with conventional techniques, a semi-finished product of a denture is filled with a resin to be the denture base, with the semi-finished product attached to the abutment installed in the oral cavity.

Therefore, it is an object of the present invention to reduce the physical/time burden on the patient and the dentist and the cost.

In order to achieve the object set forth above, a system of the present invention is, in one aspect, a denture system including a fixture 2 to be buried in an oral tissue 4, an abutment 3 coupled to the fixture 2 and having a surface to be exposed in an oral cavity, and a denture 1 to be detachably attached to the abutment 3, wherein: the denture 1 includes a denture base 10 made of a nylon-based thermoplastic resin to be in contact with a gum 40, an artificial tooth 11 supported by the denture base 10, and at least one tongue-shaped engagement piece member 13, wherein the engagement piece member 13 is deformed to flare out, as if by pivoting about an end portion 13a thereof in a vertical direction Z, when attaching/detaching the denture 1, and the engagement piece member 13 engages with the abutment 3 when worn, and wherein the engagement piece member 13, by itself or together with the denture base 10, defines a fitting hole 14 to be detachably fitted over said surface of the abutment 3; the engagement piece member 13 is formed by a nylon-based thermoplastic resin, and the engagement piece member 13 has a first surface 31 extending in a horizontal direction X along said surface of the abutment 3 over a range of a center angle θ less than 180° and extending in the vertical direction Z from the end portion 13a to be in contact with said surface of the abutment 3, and has a second surface 32 opposite to the first surface 31; and the denture base 10 has a third surface 33 opposing the second surface 32 while being spaced apart from the second surface 32, defining a groove-shaped allowance portion 15 between the second surface 32 of the engagement piece member 13 and the third surface 33 of the denture base 10, wherein the allowance portion 15 allows the engagement piece member 13 to be deformed to flare out in a direction X of moving from the first surface 31 toward the second surface 32.

In the system of the present invention, the abutment 3 fits into the fitting hole 14, formed by the engagement piece members 13, thereby making it possible to attach/detach the entire denture 1 to the abutment 3.

Since the fitting hole 14 is formed by the engagement piece members 13 made of a nylon-based resin, a high positional precision of the fitting hole 14 with respect to the abutment 3 is not needed because of the elastic deformation of the engagement piece members 13.

That is, even if the position of the fitting hole 14 is slightly shifted with respect to the abutment 3, the engagement piece member 13 made of a nylon-based resin is elastically deformed, as if by pivoting about the end portion 13a thereof, thereby improving the fit of the denture 1. Moreover, the external force acting upon the fixture 2 due to the shifting will be reduced significantly.

There is no longer a need for the step of fixing a metal piece to the denture base with the denture base placed in the patient. This reduces the physical/time burden on the patient and the dentist.

In the present system, the denture base and the engagement piece members are formed by a nylon-based thermoplastic resin (polyamide). The polyamide resin can stretch significantly in response to a stress and is easily elastically deformed. This results in a good fit. Note that the polyamide may be TR90 from EMS.

In the present invention, a metal base may be included, in addition to the denture base 10 made of nylon. The metal base is formed by a metal or an alloy, such as a gold alloy, cobalt chrome or titanium, for example, and is arranged on the inner surface or the inside of the denture base 10, thereby reinforcing the denture base 10 or connecting together a plurality of denture bases 10 for reinforcement.

In the present invention, a reinforcement material of a glass fiber, a metal, or the like, may be added inside the denture base 10 made of nylon, and the denture base 10 may be formed by an FRP, for example.

Now, since the denture 1 is removed and cleaned on a daily basis, engagement piece members 13 made of a resin may deteriorate or may be deformed permanently. In contrast, if engagement piece members 13 are formed by a nylon-based resin, they are less likely to be deformed permanently, and the engagement piece members 13 can be restored by adjusting the shape of the engagement piece members 13 back to its initial shape, etc., while blowing a hot air at and around the engagement piece members 13.

BRIEF DESCRIPTION OF DRAWINGS

FIGS. 7A and 7B are cross-sectional views showing steps 1 and 2 of a first method for producing a denture according to Embodiment 3.

FIG. 10 is an exploded perspective view showing step 7.

FIGS. 13A and 13B are perspective views showing step 6A, corresponding to the step 6, in a second method for producing a denture according to Embodiment 3.

FIG. 18 is an exploded perspective view showing step 20 according to the fourth method.

FIGS. 24A and 24B are cross-sectional views showing steps 36 and 37, respectively.

FIGS. 26A and 26B are cross-sectional views showing steps 40 and 41, respectively.

FIGS. 27A and 27B are a lateral cross-sectional view and a cross-sectional plan view, respectively, showing a denture of Embodiment 5, and FIG. 27C is a cross-sectional view showing the denture placed in the patient.

FIGS. 28A and 28B are cross-sectional views showing dentures according to Embodiments 6 and 7, respectively.

FIGS. 31A and 31B are cross-sectional views showing steps 51 and 52, respectively, of a method for producing a denture according to Embodiment 10.

FIGS. 32A and 32B are a plan view and a cross-sectional view, respectively, showing step 53, and FIG. 32C is a cross-sectional view showing step 54.

FIGS. 33A and 33B are a longitudinal cross-sectional view and a cross-sectional plan view, respectively, showing step 55, and FIGS. 33C and 33D are a cross-sectional plan view and a longitudinal cross-sectional view showing step 56.

FIGS. 35A and 35B are a cross-sectional plan view and a longitudinal cross-sectional view, respectively, showing step 63, and FIG. 35C is a longitudinal cross-sectional view showing step 64.

FIGS. 36A and 36B are a cross-sectional plan view and a longitudinal cross-sectional view, respectively, showing step 65, and FIG. 36C is a longitudinal cross-sectional view showing step 66.

FIGS. 37A and 37B are a plan view and a longitudinal cross-sectional view, respectively, showing step 71 of a method for producing a denture according to Embodiment 12, and FIG. 37C is a longitudinal cross-sectional view showing step 72.

FIGS. 41A and 41B are a cross-sectional plan view and a longitudinal cross-sectional view, respectively, showing step 91 of a method for producing a denture according to Embodiment 14, and FIGS. 41C and 41D are a cross-sectional plan view and a longitudinal cross-sectional view, respectively, showing step 92.

FIGS. 42A and 42B are cross-sectional views showing steps 101 and 102, respectively, of a method for producing a denture according to Embodiment 15.

FIGS. 45A and 45B are, a cross-sectional plan view and a longitudinal cross-sectional view, respectively, showing step 113, and FIG. 45C is a longitudinal cross-sectional view showing step 114.

FIG. 52A and FIG. 52B are cross sectional views each showing a process for producing a denture.

FIG. 55A and FIG. 55B are cross sectional views each showing a process for producing a denture.

FIG. 58A is a cross-sectional view showing a denture of another embodiment attached to an abutment, FIG. 58B and FIG. 58C are a plan view and a cross sectional view, respectively, showing further another embodiment of an engagement piece, and FIG. 58D and FIG. 58E are a plan view and a cross sectional view, respectively, showing still further embodiment of an engagement piece.

FIG. 62A is a cross sectional view of a male model in which a replica of an abutment projects, FIG. 62B is a cross sectional view of a kit comprising an engagement piece and a tubular member, FIG. 62C is a side view of the engagement piece, and FIG. 62D is a bottom view of the engagement piece.

FIG. 65A is a cross sectional view in which a replica of an abutment projects, FIG. 65B is a cross sectional view of a kit comprising an engagement piece and a tubular member, and FIG. 65C is a side view of the kit.

FIG. 66A and FIG. 66B are cross sectional views each showing still another process in a method for producing a denture.

DESCRIPTION OF EMBODIMENTS

Figure 1A:
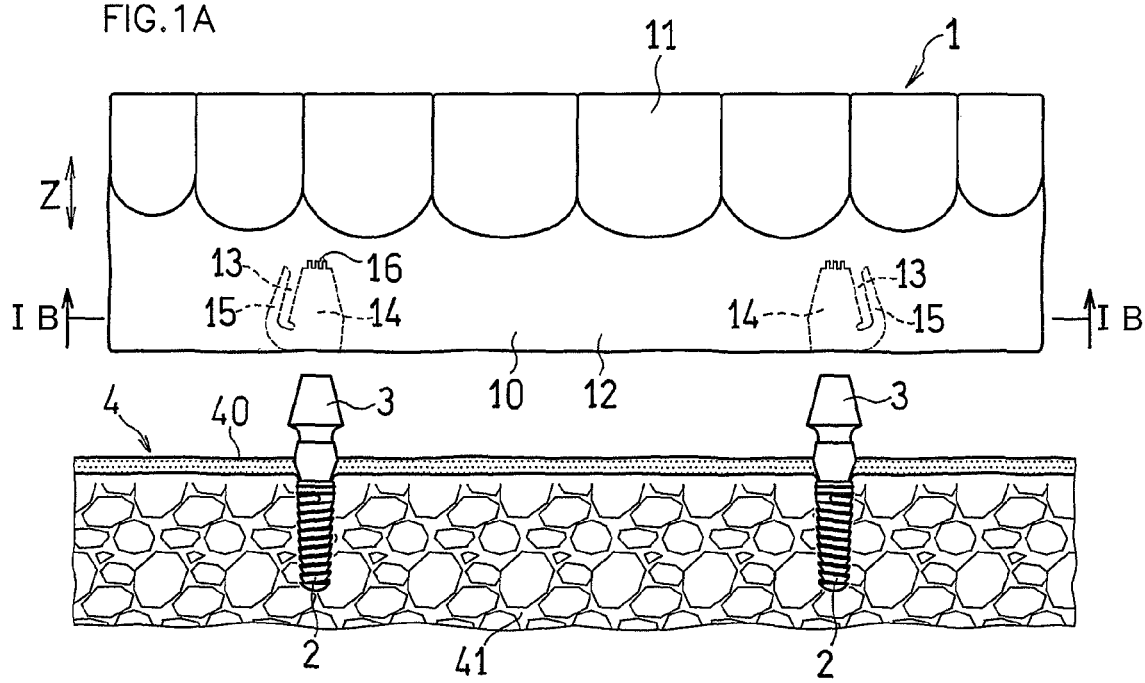
FIG. 1A is a front view showing Embodiment 1 of the present system with the denture removed from the oral cavity.

In a preferred embodiment of the present invention, one or more engagement piece members 13 are provided for one fitting hole 14, and a slit 13s extending in the vertical direction Z is defined between the engagement piece member 13 and the denture base 10 or between the plurality of engagement piece members 13 and 13; and more preferably, the engagement piece members are integrally continuous with one another via the end portion 13a and an area of the denture base 10 that covers the head of the abutment.

One or more engagement piece members 13 can freely deform with respect to one another by virtue of slits 13s extending in the vertical direction Z. Therefore, the positional shift of the fitting hole 14 with respect to the abutment 3 can be easily absorbed.

In a more preferred embodiment of the present invention, the abutment 3 includes a male screw portion 3s to be screwed into the fixture 2, and a top 3t projecting from the fixture 2 to be fitted into the denture 1 through the fitting hole 14, wherein the abutment 3 defines a narrowed circumferential engaged groove 3e to be engaged by the engagement piece member 13 between the top 3t and the male screw portion 3s, and a plurality of longitudinal grooves 3g, the number of which is equal to the number of slits 13s, spaced apart from one another in a direction of the circumference, extending from the top 3t toward the male screw portion 3s, and having a depth generally equal to or greater than a depth of the engaged groove 3e.

Note that the term "toppu (top)" means "top" in English, referring to the top portion, irrespective of whether it is pointing upward/downward.

In such a case, the longitudinal groove 3g of the abutment 3 allows the core to come into the engaged groove 3e of the abutment 3. A plurality of longitudinal grooves 3g of the abutment 3 are useful as grooves to be engaged with a tool when screwing the abutment 3 into the fixture 2.

In another preferred embodiment of the present invention, the system further includes a replica 3R having a similar shape to the abutment 3, the replica 3R including a male screw portion 3s to be screwed into the fixture 2, and a top 3t projecting from the fixture 2 so that the top 3t can be fitted into the denture 1 through the fitting hole 14, wherein the replica 3R of the abutment defines a narrowed circumferential engaged groove 3e which can be engaged with the engagement piece member 13 between the top 3t and the male screw portion 3s, and a plurality of longitudinal grooves 3g, the number of which is equal to the number of slits 13s, spaced apart from one another in a direction of the circumference, extending from the top 3t toward the male screw portion 3s, and having a depth generally equal to or greater than a depth of the engaged groove 3e.

In such a case, the longitudinal groove 3g of the replica 3R allows the core to come into the engaged groove 3e of the abutment 3.

Since the longitudinal groove 3g is formed in the replica 3R of the abutment 3 and there is no need to provide the longitudinal groove 3g in the abutment 3, the engagement between the abutment 3 without the longitudinal groove 3g and the engagement piece members 13 may likely be stable.

In a preferred embodiment of the present invention, the end portion 13a of the engagement piece member 13 is integrally continuous with the denture base 10. The engagement piece member 13 and the denture base 10 integrally continuous with each other will less likely be damaged by an external force.

In another preferred embodiment of the present invention, a plurality of engagement piece members 13 are formed as a single engagement piece 13P made of the nylon-based thermoplastic resin. The engagement piece 13P does not have a shape unique to the patient, and can therefore be mass-produced in advance with a high precision. This allows for a cost reduction and a performance enhancement.

In a more preferred embodiment of the present invention, another resin different from the resin for coupling together the engagement piece member 13 and the denture base 10 is inserted.

The other resin in such a case may be a two-component resin, called an "autopolymerizing resin (selfcuring resin)", and since technicians always have such a resin on hand, the method can easily be carried out.

In a more preferred embodiment of the present system, a plurality of fixtures 2 and abutments 3 are provided in the oral cavity, and the system is applied to the fixtures 2 and the abutments 3.

Note however that the fixture 2 and the abutment 3 may be provided only in one location with the provision of a clasp.

In a more preferred embodiment of the present system, the engagement piece member 13 and the allowance portion 15 are provided on the left side and on the right side of each fitting hole 14 so that the positions of the fitting holes 14 for the abutments 3 can be slightly moved in the left-right direction X1 of the horizontal direction X.

In such a case, even if there is a slight error between the pitch between a plurality of abutments 3 and 3 and the pitch between a plurality of fitting holes 14 and 14, awkwardness will unlikely be felt when the denture 1 is worn because of the slight movement of the engagement piece members 13.

In a more preferred embodiment of the present system, the engagement piece member 13 and the allowance portion 15 are arranged in front of the fitting hole 14 and on the back of the fitting hole 14 so that the position of the fitting hole 14 with respect to the abutment 3 is allowed to move slightly in the front-back direction Y.

In such a case, as the engagement piece member 13 slightly moves also in the front-back direction Y, substantially no awkwardness will be felt when the denture 1 is worn.

On the other hand, in one aspect, a method for producing the denture 1 of the present invention includes the steps of: producing a female mold 50 of the oral cavity using a flexible impression material 23 with at least the fixture 2 buried in the oral tissue 4; producing, from the female mold 50, a male mold 51 having a shape of the abutment 3 and a shape of the oral cavity; attaching a core 70 at least having a shape of a groove 15 forming the allowance portion 15 over an area of the male mold 51 corresponding to the abutment 3; producing a matrix 52 by filling, with a filler 53, a gap S to be an undercut formed between an end face at an upper end or a lower end of the core 70 and a surface of the male mold 51; and obtaining, from the matrix 52, the denture base 10 and the engagement piece member 13 made of a resin.

With this method, the core 70 forms the groove 15 to be the allowance portion 15, and an undercut S is filled with the filler 53. This allows the resin of the denture base 10 to be released from the core 70.

In an embodiment of the present method, in the step of producing the female mold 50, the female mold 50 is produced with the abutment 3 or the replica 3R of the abutment 3 attached to the fixture 2.

In such a case, in a preferred embodiment, the abutment 3 or the replica 3R is provided with a cylindrical outer circumferential surface 39 at a position in the vicinity of the fixture 2, wherein the cylindrical outer circumferential surface 39 has an outer diameter which is larger than an outer diameter of a top 3t projecting from the fixture 2 to be fitted into the denture 1 through the fitting hole 14 and which is smaller than an outer diameter of the fixture 2;

the core 70 includes a C-shaped or ring-shaped positioning portion 79 for positioning the core 70 with respect to the male mold 51 by being fitted over, while being in contact with, an area 519 of the male mold 51 corresponding to the cylindrical outer circumferential surface; and in the attachment step, the core 70 is attached to the male mold 51 with the positioning portion 79 fitted over the area 519 corresponding to the cylindrical outer circumferential surface 39.

In this preferred embodiment, the core 70 is positioned with respect to the male mold 51 with the positioning portion 79 fitted to the area 519 of the male mold 51 corresponding to the cylindrical outer circumferential surface 39. Therefore, even an inexperienced technician can position the core 70 with respect to the male mold 51 with a high precision.

Herein, the term "cylindrical outer circumferential surface" means that the outer circumferential surface does not need to be a complete cylindrical surface, but a portion of the cylindrical surface may be missing, and it may also be a tapered cylindrical surface.

The C-shaped or ring-shaped positioning portion 79 means that the positioning portion 79 may have an incomplete, C-shaped ring shape, as well as a complete ring shape.

In still another preferred embodiment, the core 70 includes a cylindrical portion 72A having a cylindrical shape, and a plurality of blade portions 71A extending from an inner circumferential surface of the cylindrical portion 72A toward a center of the cylindrical portion 72A at positions corresponding to the slits 13s, wherein a part or whole of the slits 13s is formed by virtue of the blade portions 71A in the step of obtaining the denture base 10.

Since the blade portions 71A form the slits 13s, the formation of the slits 13s is facilitated.

Note that the slits 13s may be partially formed by the blade portions 71A, with the remaining portion of the slits 13s being formed by removing the resin by processing.

In a more preferred embodiment of the present method, in the step of producing the male mold 51, longitudinal grooves 51g for receiving projecting ends of the blade portions 71A fitted thereto and allowing the blade portions 71A to move vertically when the core 70 is attached are provided in an area of the male mold 51 corresponding to the abutment 3, and the blade portions 71A of the core 70 are attached in the vertical direction Z along the longitudinal grooves 51g.

In such a case, the blade portions 71A come into the engaged grooves 3e of the abutment 3. Therefore, since a part or whole of the slits 13s is formed in the molding process, the formation of the slits 13s is facilitated.

In another preferred embodiment of the present method, the method further includes a processing step of removing portions of the denture base 10, produced from the matrix 52, to be slits 13s.

In such a case, since the slits 13s are formed by subsequent processing, the shape of the core 70 is simplified, and it is possible, with cores 70 of a single shape, to accommodate abutments 3 of different shapes.

In still another embodiment of the present method, in the step of producing the male mold 51, the male mold 51 having a shape of the oral cavity, with the replica 60 of the fixture 2 buried in the male mold 51, is produced from the female mold 50; and in the step of attaching the core 70, the core 70 having a shape of the fitting hole 14 and a shape of a groove 15 forming the allowance portion 15 is attached to the replica 60.

In such a case, since the core 70 is attached to the replica 60 of the fixture 2, the positional shift of the allowance portion 15 with respect to the fixture 2 is unlikely to occur.

In still another embodiment of the present method, the method includes: a step of producing a female mold 50 of an oral cavity with at least the fixture 2 buried in the oral tissue 4; a step of producing, from the female mold 50, a male mold 51 having a shape of a projecting portion 15P corresponding to the allowance portion 15 and a shape of the oral cavity; a step of producing, from the male mold 51, a denture base 10 having a shape of a hole 15H forming the allowance portion 15; and a coupling step of coupling an end portion of the engagement piece 13P in the vertical direction Z to the denture base 10, with the engagement piece 13P and the denture base 10 being spaced apart from each other over the allowance portion 15, thereby obtaining the denture 1 while ensuring the allowance portion 15.

If an engagement piece 13P including a plurality of engagement piece members 13 is formed in advance, as described above, it saves the technician's labor of molding slits between a plurality of engagement piece members 13, thus facilitating the fabrication of the denture 1.

A system of the present invention is, in another aspect, a denture system applied to a plurality of fixtures 2 buried in an oral tissue 4, the denture system comprising: abutments 3 coupled to the fixtures 2 and having a surface to be exposed in an oral cavity; and a denture 1 to be detachably attached to the abutments 3, the denture 1 including:

a denture base 10 made of a resin and to be in contact with a gum 40;

an artificial tooth 11 supported by the denture base 10;

a plurality of tongue-shaped engagement piece members 13 that are plurally separated in a circumferential direction, wherein the engagement piece members 13 are deformed to spread, as if by pivoting about each end portion 13a thereof in an up-down direction Z, when attaching and detaching the denture 1, and the engagement piece members 13 engage with the abutments 3 when worn, and wherein the engagement piece members 13 define a slit 13s extending in the up-down direction Z and define a fitting hole 14 to be detachably fitted over the surface of the abutment 3;

a lid 13c configuring a part of the denture base 10, wherein the lid portion 13c closes one end of the fitting hole 14 in the up-down direction Z as well as connects end portions 13a of the engagement piece members 13 with each other, and covers an entire surface of a top 3t of each of the abutments 3, each of the engagement piece members 13 and the lid portion 13c are formed by a nylon-based thermoplastic resin, each of the engagement piece members 13 has a first surface 31 extending in a horizontal direction X along the surface of the abutment 3 over a range of a center angle θ less than 180° and extending in the up-down direction Z from one of the end portions 13a to be in contact with the surface of the abutment 3, and has a second surface 32 opposite to the first surface 31; and a groove-shaped allowance portion 15 provided for an outer circumference of the second surface 32 of each of the engagement piece members 13, wherein the allowance portion 15 allows the engagement piece members 13 to be deformed to spread in a direction from the first surface 31 toward the second surface 32.

Preferably, the denture base 10 has a third surface 33 opposing the second surface 32 while being spaced apart from the second surface 32, and the groove-shaped allowance portion 15 is defined between the second surface 32 of each the engagement piece members 13 and the third surface 33 of the denture base 10.

Preferably, a plurality of cushion portions 16, a plurality of arc-shaped cushion portions 16, or an annular cushion portion 16 is integrally formed in an area of the lid portion 13c corresponding to an outer circumferential edge of the top 3t of each of the abutments 3, and each of the cushion portions 16 projects toward each of the abutments 3 inside the engagement piece members 13.

The cushion portion 16 works as a cushion to the denture 1 instead of a natural periodontal ligament by elastically deforming after receiving the reaction force from a surface of the top 3t of the abutment 3 when biting.

In this case, the cushion portion 16 is integrally formed in the engagement piece 13P in advance, thereby further reducing a dental technician's burden.

An engagement piece of the present invention is used for a denture system including an abutment 3 having a surface to be exposed in an oral cavity and a denture 1 to be detachably attached to the abutment 3, the denture 1 comprising: a body part 12 of a denture base 10, the denture base 10 formed by a resin and to be in contact with a gum 40; an artificial tooth 11 supported by the body part 12 of the denture base 10; and an engagement piece 13P for engaging the body part 12 of the denture base 10 to the abutment 3, the engagement piece 13P formed by a nylon-based thermoplastic resin and forming a part of the denture base 10, wherein the engagement piece 13P includes:

a lid portion 13c to cover an entire surface of a top 3t of the abutment 3 and to be covered by the body part 12 of the denture base 10, and a plurality of engagement piece members 13 extending from the lid portion 13c in an up-down direction Z, wherein the engagement piece members 13 elastically deform to spread around an end portion 13a in the up-down direction Z when attaching and detaching the denture 1, engage with the abutment 3 when worn, and are spaced apart from one another in a circumferential direction, wherein each of the engagement piece members 13 has a first surface 31 to be in contact with an outer circumferential surface of the abutment 3 and has a second surface 32 opposite to the first surface 3, and the first surfaces 31 of the engagement piece members 13 define a fitting hole 14 to be detachably fitted over the outer circumferential surface of the abutment 3, and the lid portion 13c closes one end, in the up-down direction Z, of the fitting hole 14 defined by the engagement piece members 13.

When the engagement piece 13P is produced by injection molding with metal patterns in a lot production, it is not necessary for a dental technician to manufacture every time a plurality of engagement piece members 13 or a slit 13s between the engagement piece members 13.

Preferably, the engagement piece 13P further comprises an outer portion 13r extending in the up-down direction Z from a circumference of the lid portion 13c to sandwich a tubular member between the outer portion 13r and the engagement piece members 13, and the outer portion 13r has a third surface 33 being further from an axis 3L of the abutment 3 than the second surfaces 32 of the engagement piece members 13, and the outer portion 13r is joined to the body part 12 of the denture base 10, an allowance portion 15 is defined between the second surfaces 32 and the third surface 33 of the outer portion 13r and allows the engagement piece members 13 to be elastically deformed to spread in a direction from the first surface 31 toward the second surface 32, and the lid portion 13c closes one end, in the up-down direction, of the fitting hole 14 defined by the engagement piece members 13 and the one end, in the up-down direction, of the allowance portion 15.

In this case, it is easy for a dental technician to form the allowance portion 15 when molding the denture base 10.

More preferably, the outer portion 13r of the engagement piece 13P extends in the up-down direction Z from an outer circumference of the lid portion 13c and is formed in tubular shape, and an inner circumferential surface of the tubular outer portion 13r defines the third surface 33.

In this case, it becomes much easier to form the allowance portion 15.

Preferably, a plurality of cushion portions 16, a plurality of arc-shaped cushion portions 16, or an annular cushion portion 16 is integrally formed in an area of the lid portion 13c corresponding to an outer circumference of the top 3t of the abutment 3, and each of the cushion portions 16 projects toward the abutment 3 inside the engagement piece members 13.

The cushion portion 16 works as a cushion to the denture 1 instead of a natural periodontal ligament by elastically deforming after receiving the reaction force from a surface of the top 3t of the abutment 3 when biting.

In this case, the cushion portion 16 is integrally formed in the engagement piece 13P in advance, thereby further reducing a dental technician's burden.

Now, a resin itself is colorless and transparent. A resin used for the denture base 10 of a denture is always provided with a pigment in order to obtain a tone of color similar to gum. However, in light of safety to human body, such a pigment is limited to fine powder of metallic oxide such as $Fe_2O_3$ and $TiO_2$ having a rough surface in microscopic.

Such fine powder having rough surface damages resin material of an engagement piece member 13 in microscopic when the engagement piece member 13 deforms. Therefore, if an additive amount of the pigment is set to be from 0.10 weight percent to 0.20 weight percent as in the past, strength of the engagement piece member 13 may be deteriorated by detaching and attaching a denture 1 every day. If this deterioration becomes remarkable, elasticity of the engagement piece member 13 may be lost, or the engagement piece member 13 may be damaged.

Therefore, preferably, a ratio of a pigment to a resin forming the engagement piece 13P is set to be from 0 weight percent to 0.07 weight percent.

In this case, since a ratio of the pigment is smaller than a conventional ratio of the pigment, the denture 1 shows an excellent durability when repeatedly detaching from and attaching to the abutment 3.

When no pigment is contained into the engagement piece 13, the engagement piece member 13 may show the most excellent durability. On the other hand, when texture (feeling) of a denture base 10 is considered to be important, it is preferable to contain a small amount of pigment.

From such a view point, it is preferable that a ratio of a pigment to a resin (nylon) forming an engagement piece 13 is set to be from 0 weight percent to 0.05 weight percent, and it is most preferable that such a ratio is set to be from 0 weight percent to 0.03 weight percent.

Note: even if no pigment is added to nylon of the engagement piece 13P, adding a pigment into a resin of the body part 12 of the denture base 10 prevents texture (feeling) from degrading.

Preferably, a ratio of pigment contained in a resin forming the engagement piece 13P is smaller than a ratio of pigment contained in a resin forming the body part 12.

In this case, a ratio of pigment contained in a nylon of the engagement piece member 13 is smaller than a ratio of pigment contained in a resin of the body part 12 of the denture base 10. Therefore, an excellent durability and good texture (feeling) will be achieved.

A method for producing a denture 1 according to the present invention, in another aspect, is a method for producing a denture 1 to be detachably attached to the abutment 3 having a surface to be exposed in an oral cavity, the denture 1 including a body part 12 of a denture base 10 made of a resin and to be in contact with a gum 40, an artificial tooth 11 supported by the body part 12 of the denture base 10, and an engagement piece 13P made of a nylon-based thermoplastic resin, forming a part of the denture base 10, and engaging the body part 12 of the denture base 10 to the abutment 3, wherein the engagement piece 13P includes:

a lid portion 13c to cover an entire surface of a top 3t of the abutment 3 and to be covered by the body part 12 of the denture base 10;

a plurality of engagement piece members 13 extending from the lid portion 13c in an up-down direction Z, wherein the engagement piece members 13 elastically deform to spread around an end portion 13a in the up-down direction Z when attaching and detaching the denture 1, engage with the abutment 3 when worn, and are spaced apart from one another in a circumferential direction, wherein each of the engagement piece members 13 has a first surface 31 to be in contact with an outer circumferential surface of the abutment 3 and has a second surface 32 opposite to the first surface 3, and the first surfaces 31 of the engagement piece members 13 define a fitting hole 14 to be detachably fitted over the outer circumferential surface of the abutment 3; and an outer portion 13r extending in the up-down direction Z from a circumference of the lid portion 13c to sandwich a tubular member between the outer portion 13r and the engagement piece members 13, and the outer portion 13r has a third surface 33 being further from an axis 3L of the abutment 3 than the second surfaces 32 of the engagement piece members 13, and the outer portion 13r is joined to the body part 12 of the denture base 10, an allowance portion 15 is defined between the second surfaces 32 and the third surface 33 of the outer portion 13r and allows the engagement piece members 13 to be elastically deformed to spread in a direction from the first surface 31 toward the second surface 32, and the lid portion 13c closes one end, in the up-down direction, of the fitting hole 14 defined by the engagement piece members 13 and the one end, in the up-down direction, of the allowance portion 15, wherein the method for producing the denture 1 comprises the steps of:

producing a female resin mold 54 having a depressed portion 500 corresponding to a shape of an oral tissue 4, and the engagement piece 13P embedded in the depressed portion 500;

inserting a restraint member R into the allowance portion 15 of the engagement piece 13P, the restraint member R to be inserted into the allowance portion 15 and to be a core when molding the body part 12 of the denture base 10, preventing the outer portion 13r from deforming toward the engagement piece members 13 when molding the body part 12 of the denture base 10;

producing a male plaster mold 56 by pouring a plaster into the depressed portion 500 of the female resin mold 54 after the insertion of the restraint member R, the restraint member R and the engagement piece 13P being integral with the plaster;

producing a denture base 10 in which the engagement piece 13P is integral with the body part 12 of the denture base 10 by supplying a molten resin around the male plaster mold 56; and removing the male plaster mold 56 and the restraint member R.

In this case, the restraint member R restrains the outer part 13r from deforming toward the engagement piece members 13 when molding the denture base 10. Thereby, the allowance portion 15 is secured, and the engagement piece members 13 engage with an engaged part of the abutment 3, and the denture 1 is attached to or detached from the abutment 3.

Furthermore, since the engagement piece members 13 are formed in the engagement piece 13P in advance, it is easy for a dental technician to work.

Especially, since the restraint member R or a tubular member R1 is inserted into the allowance portion 15, the outer portion 13r is prevented from its deformation caused by pressure in molding process of the denture base 10.

A method for producing a denture 1 according to the present invention, in still another aspect, is a method for producing a denture 1 to be detachably attached to the abutment 3, the denture 1 including a body part 12 of a denture base 10 made of a resin and to be in contact with a gum 40, an artificial tooth 11 supported by the body part 12 of the denture base 10, and an engagement piece 13P made of a nylon-based thermoplastic resin, forming a part of the denture base 10, and engaging the denture base 10 to the abutment 3, wherein the engagement piece 13P includes:

a lid portion 13c to cover an entire surface of a top 3t of the abutment 3 and to be covered by the body part 12 of the denture base 10; and a plurality of engagement piece members 13 extending from the lid portion 13c in an up-down direction Z, wherein the engagement piece members 13 elastically deform to spread around an end portion 13a in the up-down direction Z when attaching and detaching the denture 1, engage with the abutment 3 when worn, and are spaced apart from one another in a circumferential direction, wherein each of the engagement piece members 13 has a first surface 31 to be in contact with an outer circumferential surface of the abutment 3 and has a second surface 32 opposite to the first surface 31, and the first surfaces 31 of the engagement piece members 13 define a fitting hole 14 to be detachably fitted over the outer circumferential surface of the abutment 3, the method for producing the denture comprising the steps of:

producing a female mold 50 having a depressed portion 500 corresponding to a shape of an oral tissue 4, and a replica 3R of the abutment 3 embedded in the depressed portion 500;

producing a male mold 51 by pouring a plaster into the depressed portion 500 of the female mold 50, the replica 3R projecting from the male mold 51;

externally fitting the engagement piece 13P on the replica 3R of the male mold 51, wherein a tubular member R1 for forming an allowance portion 15 is externally fitted on an outer circumference of the engagement piece members 13 of the engagement piece 13P, and the allowance portion 15 allows an elastic deformation of the engagement piece members 13;

producing a denture base 10 in which the engagement piece 13P and the tubular member R1 are integral with the body part 12 of the denture base 10 by supplying a molten resin around the male plaster mold 56; and removing the male plaster mold 51 and the tubular member R1.

The present invention will be understood more clearly from the following description of preferred embodiments taken in conjunction with the accompanying drawings. Note however that the embodiments and the drawings are merely illustrative, and should not be relied upon for defining the scope of the present invention. The scope of the present invention shall be defined only by the appended claims. In the accompanying drawings, like reference numerals denote like components throughout the plurality of figures.

[Embodiment]

Embodiments of the present invention will now be described with reference to the drawings.

Figure 1B:
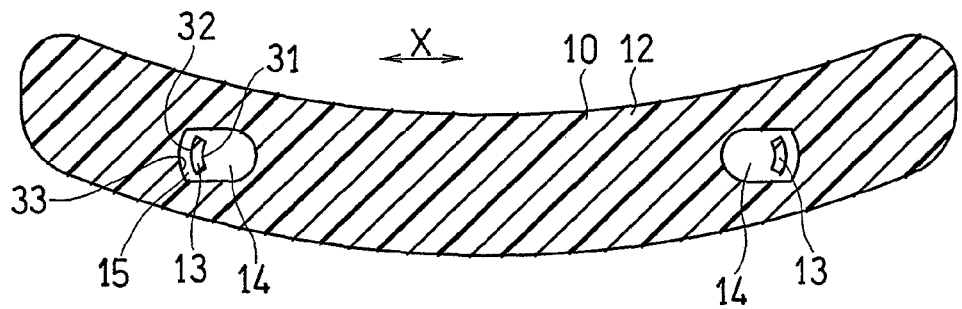
FIG. 1B is a cross-sectional plan view of the denture base taken along line IB-IB.
Figure 1C:
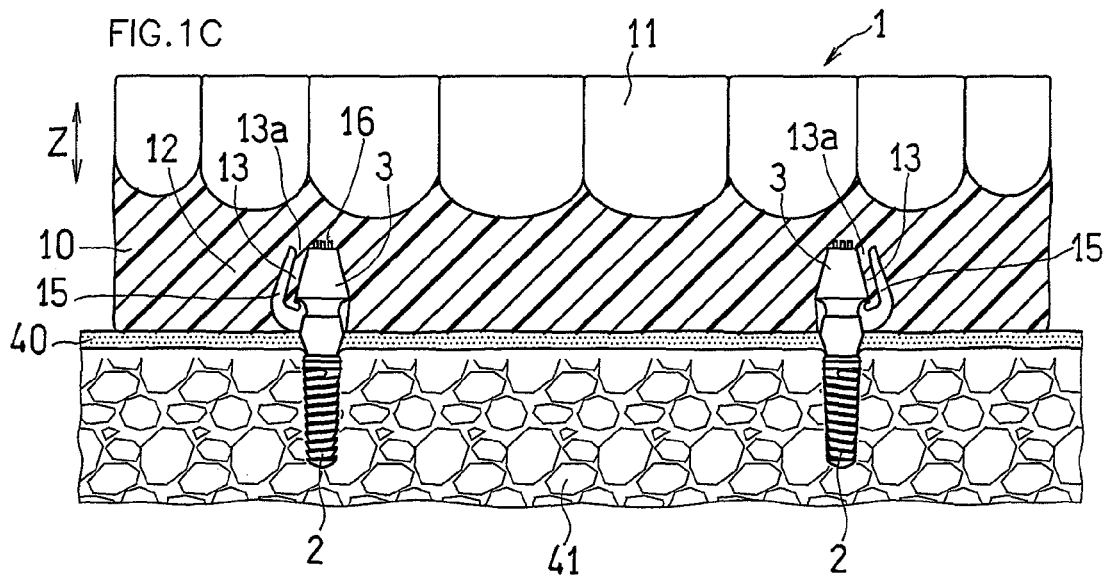
FIG. 1C is a plan view showing Embodiment 1 with the denture placed in the oral cavity.
Figure 2:
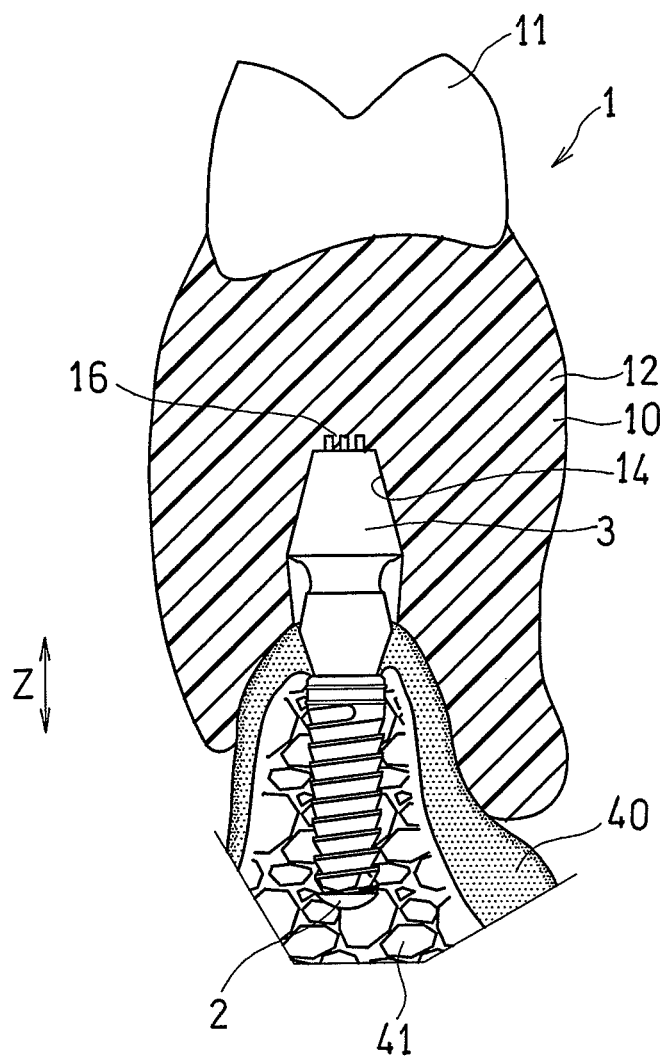
FIG. 2 is a lateral cross-sectional view of Embodiment 1.

FIGS. 1 to 3 show Embodiment 1.

As shown in FIGS. 1A and 1C, the present denture system includes the denture 1, the fixture 2, and the columnar abutment 3.

As shown in FIG. 2, the fixture 2 is a so-called "implant body", an artificial tooth root obtained by performing a surface process (surface finishing) on a biomaterial (a typical material being titanium, which is well compatible with a living body). The fixture 2 is buried in the oral tissue 4 such as an alveolar bone 41 of the jaw to be integrated with the bone.

The abutment 3 is coupled to the fixture 2 and exposed in the oral cavity. That is, the abutment 3 is fixed to the fixture 2 with a screw (not shown) and is coupled to the fixture 2 so that the artificial denture 1 can be attached thereto.

As shown in FIGS. 1A and 1C, the denture 1 is detachably attached to the abutment 3. The denture 1 includes the nylon-made denture base 10 to be in contact with the gum 40, and ceramic artificial teeth 11 integral with the denture base 10 and supported by the denture base 10.

For example, a pair of the fixtures 2 and the abutments 3 is provided in the oral cavity, and the present system is applied to the pair of the fixtures 2 and the abutments 3.

The artificial teeth 11 are secured to one end of the denture base 10 in the vertical direction Z. The other end surface of the denture base 10 in the vertical direction Z is softly in contact with the gum 40.

Figure 3A:
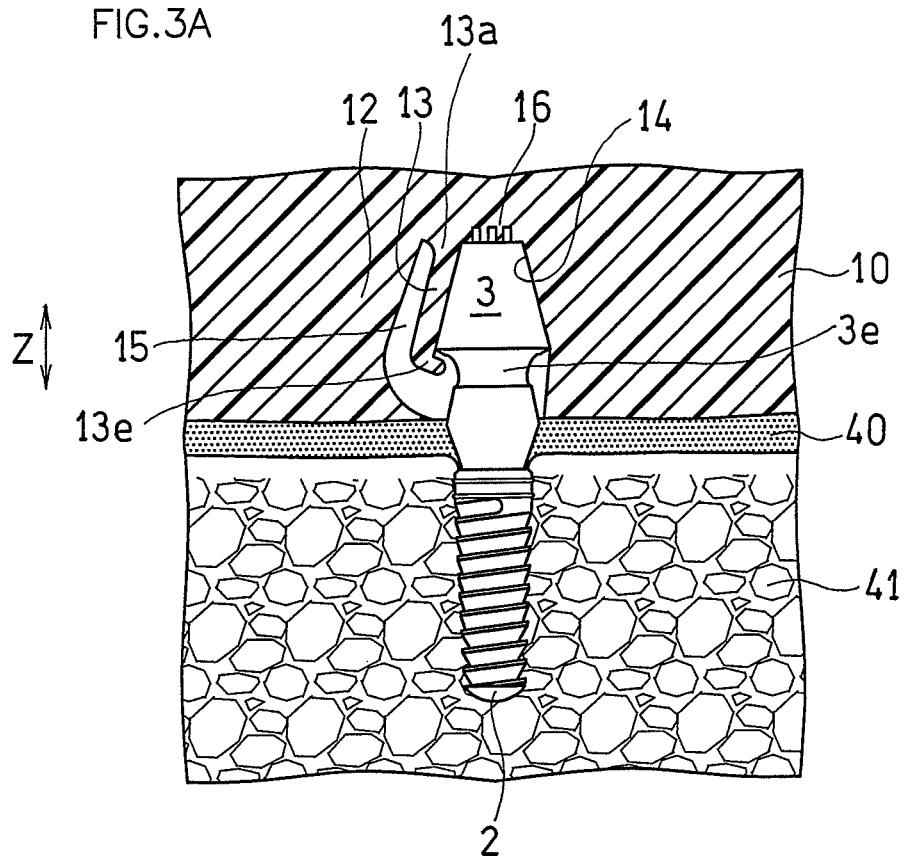
FIG. 3A is an enlarged longitudinal cross-sectional view of an important part of Embodiment 1.

As shown in the enlarged cross-sectional view of FIG. 3A, the denture base 10 includes a main body 12 and the engagement piece members 13 integrally continuous with each other, and defines the fitting holes 14 into which columnar abutments 3 are detachably fitted. The engagement piece members 13 and the denture base 10 are formed by a nylon-based thermoplastic resin, for example.

The fitting holes 14 are open toward the gum 40. That is, the fitting holes 14 of an upper denture 1 are open in the upward direction, and the fitting holes 14 of a lower denture 1 are open in the downward direction.

Figure 3B:
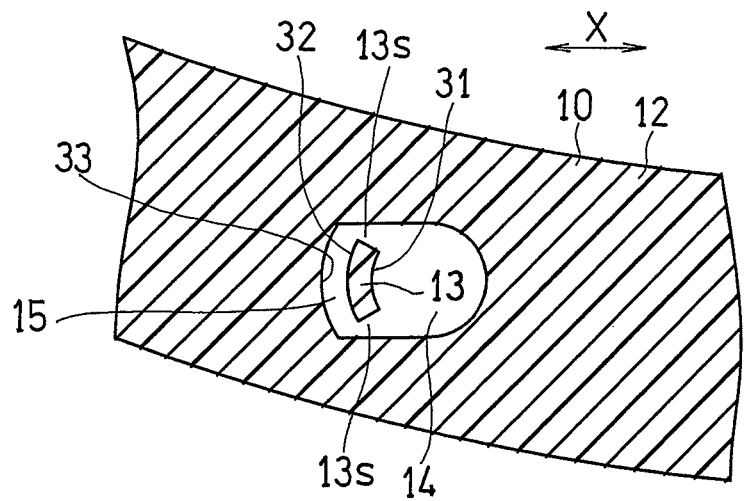
FIG. 3B is an enlarged cross-sectional plan view of an important part of Embodiment 1.

As shown in FIGS. 3A and 3B, in the present embodiment, the engagement piece member 13 forms a part of the fitting hole 14. That is, in the present embodiment, as clearly shown in FIG. 3B, the fitting hole 14 is defined by the main body 12 and the engagement piece member 13. The fitting hole 14 positions and fixes the denture base 10 with respect to the abutment 3. The engagement piece member 13 has a first surface 31 to be in contact with and engaging with the side surface of the abutment 3, and a second surface 32 opposite to the first surface 31.

In the present embodiment, where the denture 1 is placed in the lower jaw, the upper end portion 13a of the engagement piece member 13 of FIG. 3A is continuous with the denture base 10, and the engagement piece member 13 extends downwardly in the vertical direction Z from the end portion 13a of the engagement piece member 13.

Note that although not shown, in a case where the denture 1 is placed in the upper jaw, the lower end portion of the engagement piece member 13 is continuous with the main body 12, and the engagement piece member 13 extends upwardly in the vertical direction Z from the end portion of the engagement piece member 13.

In the present embodiment, an engagement element (engagement protrusion) 13e to be engaged with the narrowed engaged groove (engaged element) 3e of the abutment 3 is formed integrally with the engagement piece member 13 at the lower end of the engagement piece member 13. As the engagement element 13e is engaged with the engaged groove 3e, the denture 1 is prevented from inadvertently coming off the abutment 3.

The denture base 10 of FIG. 3B includes the allowance portion 15 formed between the second surface 32 and the third surface 33 of the main body 12, wherein the allowance portion 15 allows the engagement piece member 13 to move or deform in the horizontal direction X from the first surface 31 toward the second surface 32. The allowance portion 15 is provided as a groove 15 formed in the denture base 10. The third surface 33 is spaced apart from, and opposing, the second surface 32.

In the present embodiment, the groove 15 is continuous with the fitting hole 14 via the slit 13s, thereby facilitating the movement of the engagement piece member 13. When placing/removing the denture 1, the engagement piece member 13 retracts toward the groove 15, thereby allowing the denture 1 to be attached/detached to/from the abutment 3.

The denture base 10 may include a cushion portion 16 formed at the deep end in the vertical direction Z of the fitting hole 14 of FIG. 3A. The cushion portion 16 is formed by a plurality of small projections, and the projections will provide the denture 1 with cushioning in place of the natural periodontal membrane by elastically deforming when clenching the teeth.

The denture base 10 made of a nylon-based resin will unlikely deteriorate and will unlikely whiten over years of use. Moreover, the denture base 10 of such a material will unlikely lose the elasticity of the engagement piece member 13. Particularly, when the engagement piece member 13 deteriorates due to permanent deformation, lowering of elasticity, etc., it will be possible to restore the engagement piece member 13 while heating, with a hot air, the engagement piece member 13 and the denture base 10 around the fitting hole 14.

Figure 4A:
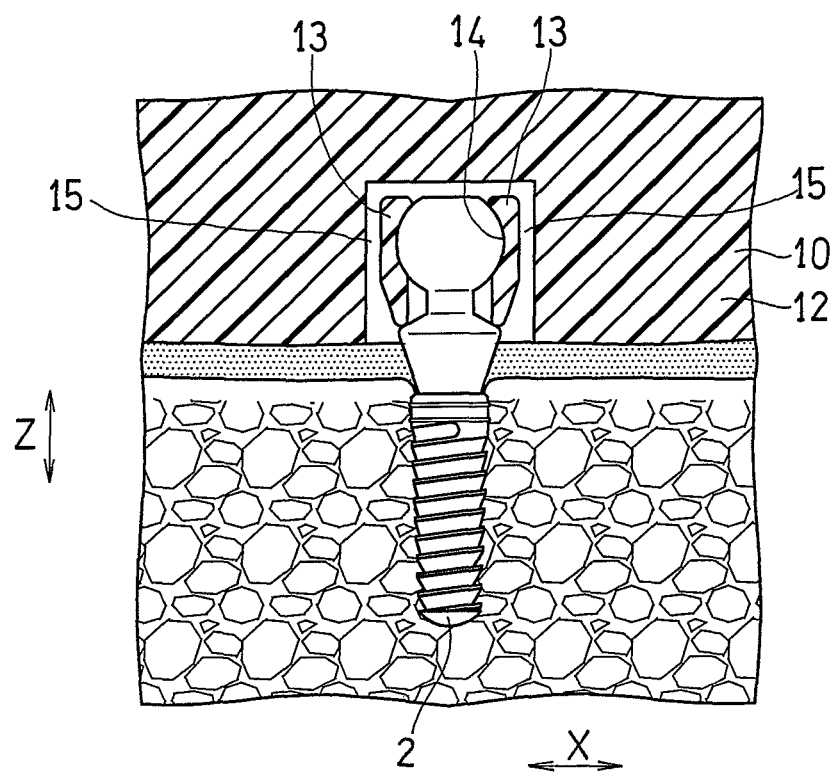
FIG. 4A is an enlarged longitudinal cross-sectional view of an important part of a reference embodiment as an aid to understanding the present invention.
Figure 4B:
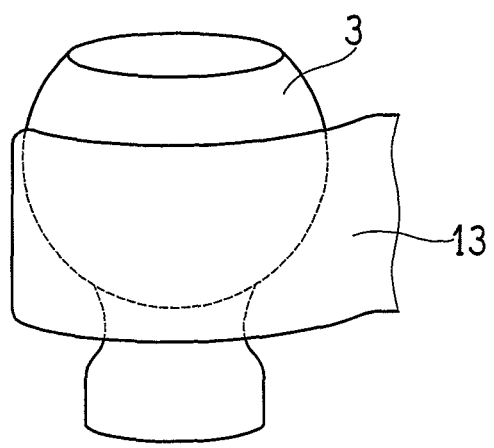
FIG. 4B is an enlarged perspective view of an important part of the reference embodiment.

FIGS. 4A and 4B show a reference embodiment as an aid to understanding the present invention.

In this example, a pair of engagement piece members 13 is provided. The pair of engagement piece members 13 extend in the horizontal direction X from the denture base 10. In this example, it will be difficult to release in the molding process.

Figure 5A:
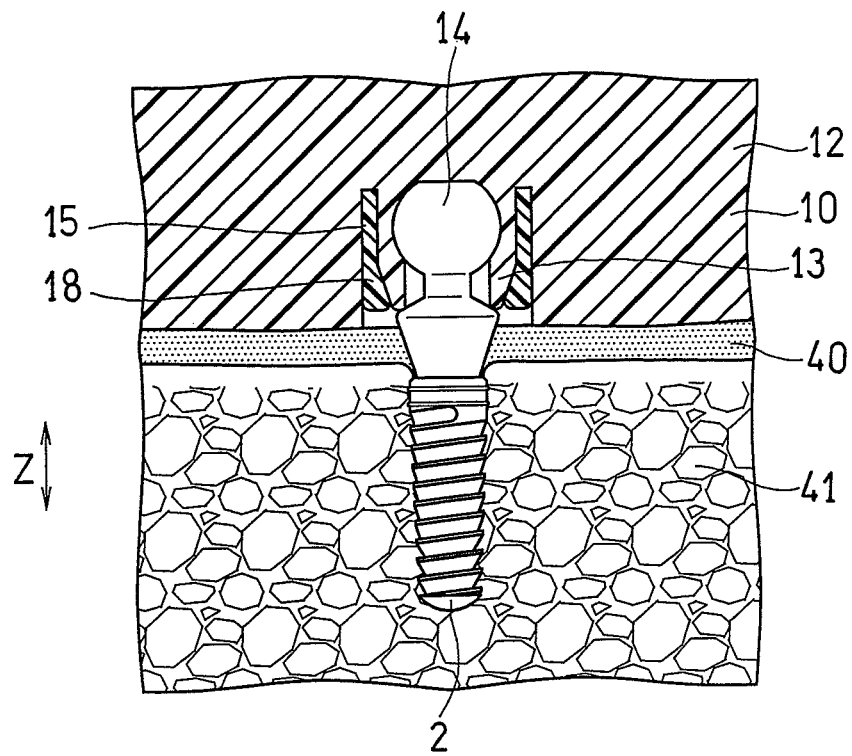
FIG. 5A is an enlarged longitudinal cross-sectional view of an important part of Embodiment 2.
Figure 5B:
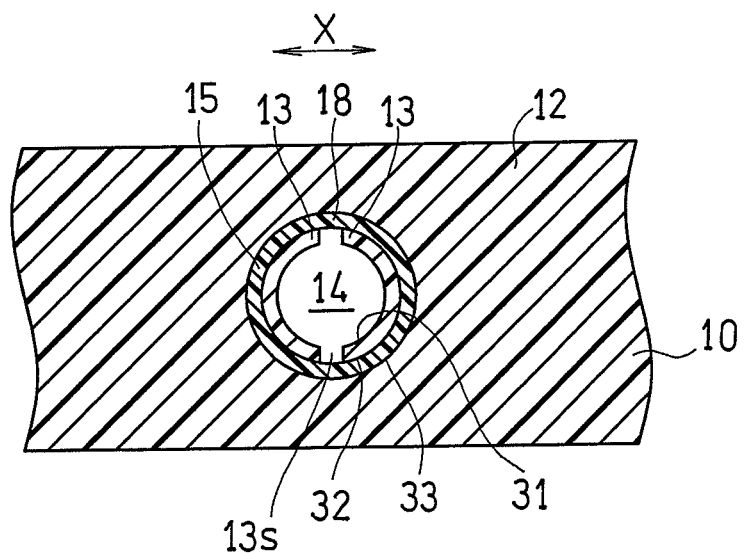
FIG. 5B is an enlarged cross-sectional plan view of an important part of Embodiment 2.

FIGS. 5A and 5B show Embodiment 2.

In Embodiment 2, a pair of semi-cylindrical engagement piece members 13 is provided. The pair of engagement piece members 13 extend in the vertical direction Z from the denture base 10. The groove 15 is filled with a buried material 18 such as silicone gel (i.e., the material 18 is buried in the groove 15). The buried material 18 compressively deforms to allow the movement of the engagement piece member 13.

Figure 6A:
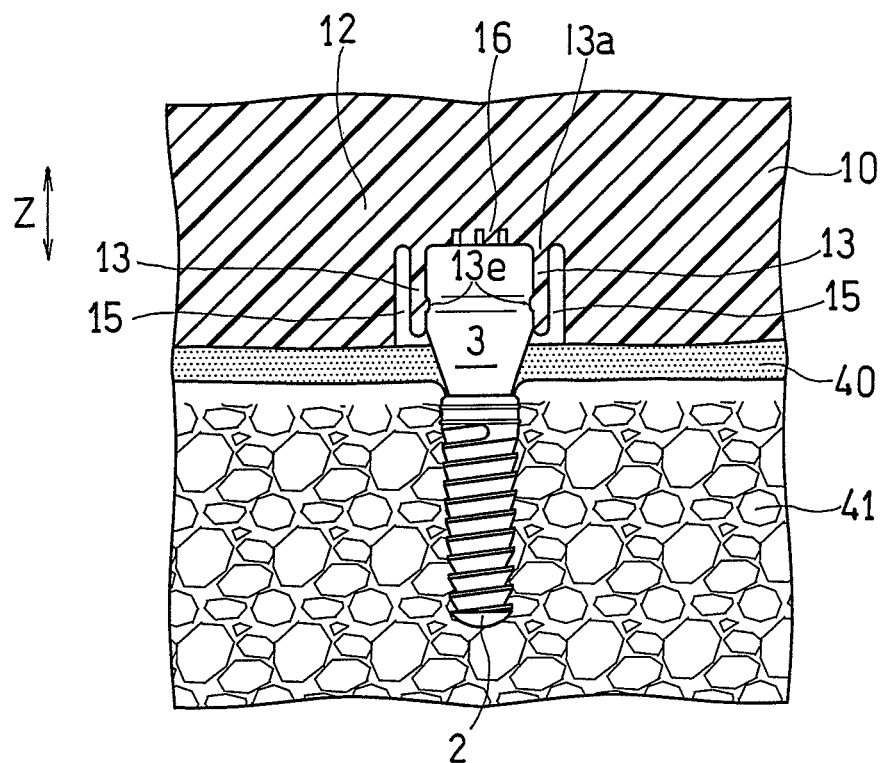
FIG. 6A is an enlarged longitudinal cross-sectional view of an important part of Embodiment 3.
Figure 6B:
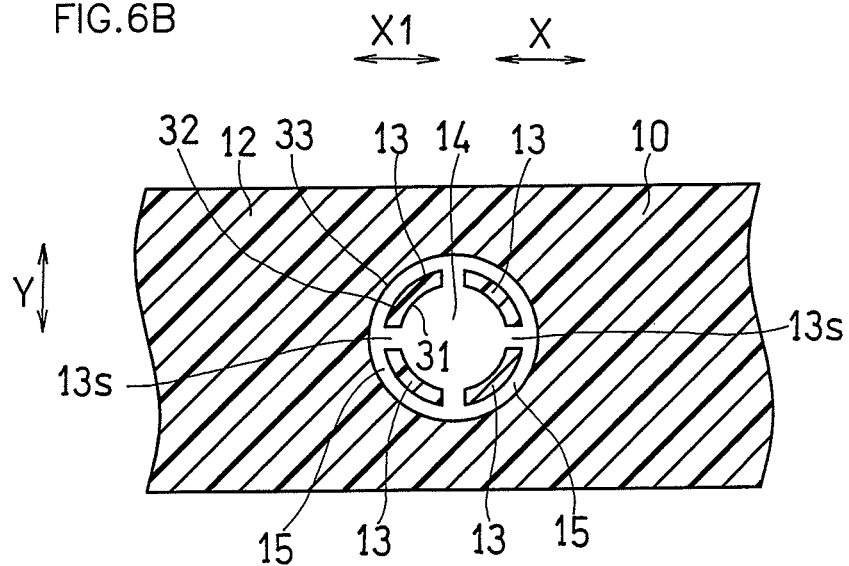
FIG. 6B is an enlarged cross-sectional plan view of an important part of Embodiment 3.

FIGS. 6A and 6B show Embodiment 3.

In Embodiment 3, the engagement piece member 13 is provided while being divided in four pieces. The four divided engagement piece members 13 form a generally cylindrical shape as a whole, and extend in the vertical direction Z from the denture base 10. Note that the engagement element 13e may be formed as a small hemispherical projection integral with the first surface 31 (see FIG. 20B).

In Embodiments 2 and 3, where the engagement piece member 13 and the allowance portion 15 are arranged on the left side and on the right side of the fitting hole 14, the position of each fitting hole 14 with respect to the corresponding abutment 3 is allowed to move slightly in the left-right direction X1 of the horizontal direction X.

Where the engagement piece member 13 and the allowance portion 15 are arranged in front of the fitting hole 14 and on the back of the fitting hole 14, the position of the fitting hole 14 with respect to the abutment 3 is allowed to move slightly in the front-back direction Y. Thus, where slight movement is allowed in the left-right direction X1 or the front-back direction Y, a shift between the position of the abutment 3 and the position of the fitting hole 14 will be absorbed in these directions.

Next, an example of a method for producing the denture base 10 according to the present invention will be described with reference to FIGS. 7A to 12B. Note that for the convenience of drafting figures, the protruding portion of the engagement piece member 13 is not shown in the embodiment of FIGS. 7A to 16B and in the embodiment of FIGS. 18 and 19.

First, as shown in step 1 of FIG. 7A, the dentist produces a female mold 50 of the oral cavity with the fixture 2 buried therein according to a well-known method.

That is, after attaching, by screwing, a guide pin 22 into a female screw of the fixture 2, the dentist places the impression material 23 made of a self-hardening resin in the oral cavity, and presses the surface of the impression material 23 against the surface of the oral cavity. The impression material 23 is more flexible than the nylon-based resin forming the denture base 10. Next, an open tray 21 is set so that the guide pin 22 projects through a window 20 of the open tray 21. Then, after turning the tip of the guide pin 22 to take out the guide pin 22 from the female screw of the fixture 2, the open tray 21 and the impression material 23 are removed from the oral cavity. Thus, the female mold 50 is produced.

Next, as shown in step 2 of FIG. 7B, after the impression material 23 is solidified, a replica 60 of the fixture 2 is screwed and fixed to the tip of the guide pin 22. The subsequent steps are performed by the dental technician rather than the dentist.

Figure 8A:
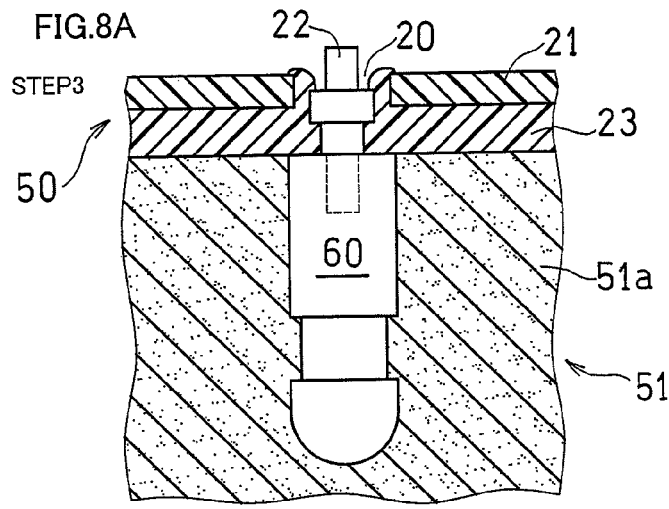
FIGS. 8A, 8B and 8C are cross-sectional views showing steps 3, 4 and 5, respectively.

As shown in step 3 of FIG. 8A, the technician pours a plaster 51a onto the surface of the impression material 23 in order to make a male mold 51 of the impression material 23. Thus, the male mold 51 of FIG. 8B, having the replica 60 of the fixture 2 is buried therein and having the shape of the oral cavity, is produced from the female mold 50.

Figure 8B:
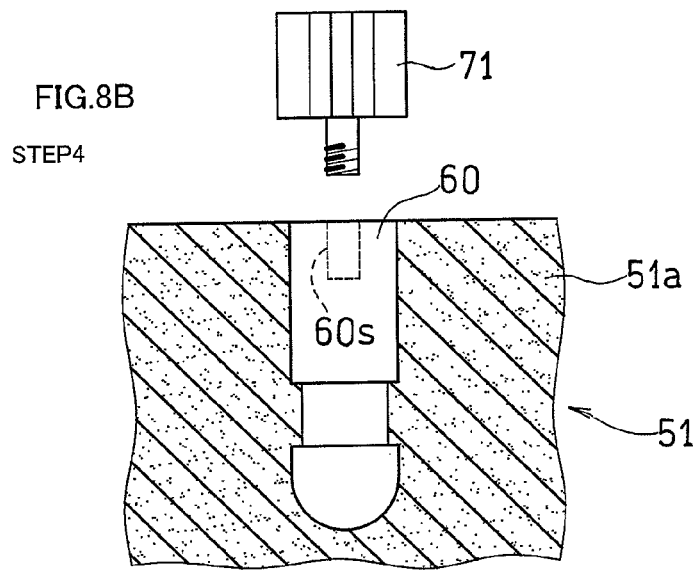
Figure 9A:
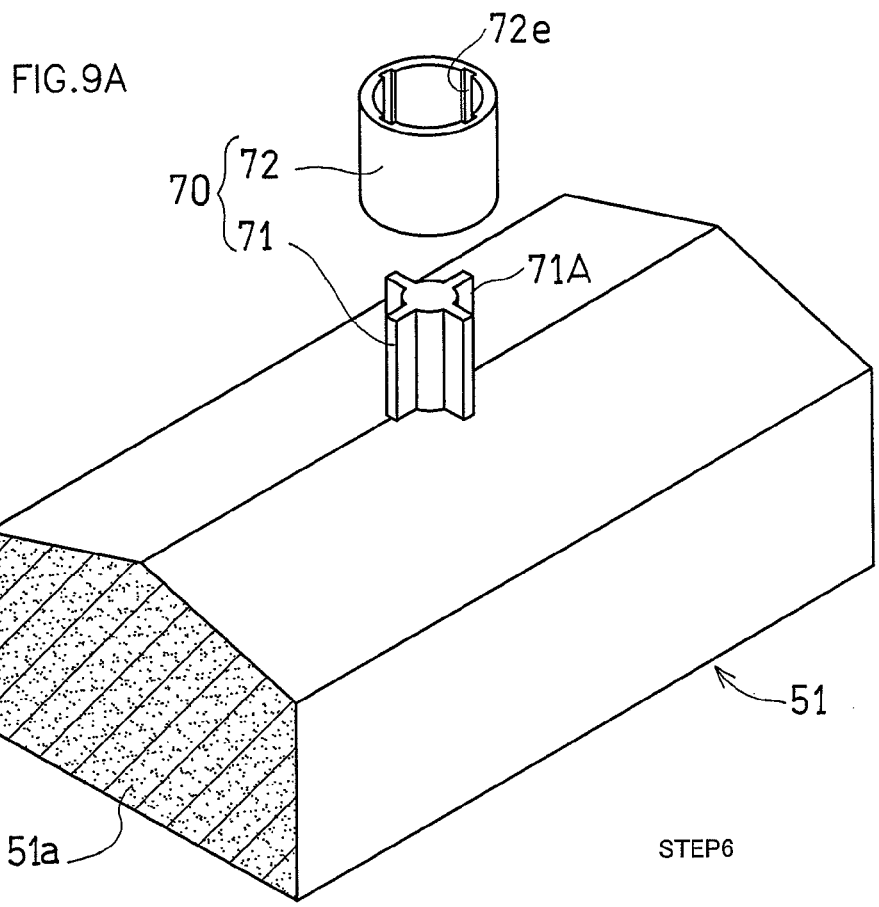
FIGS. 9A and 9B are perspective views showing step 6.
Figure 9B:
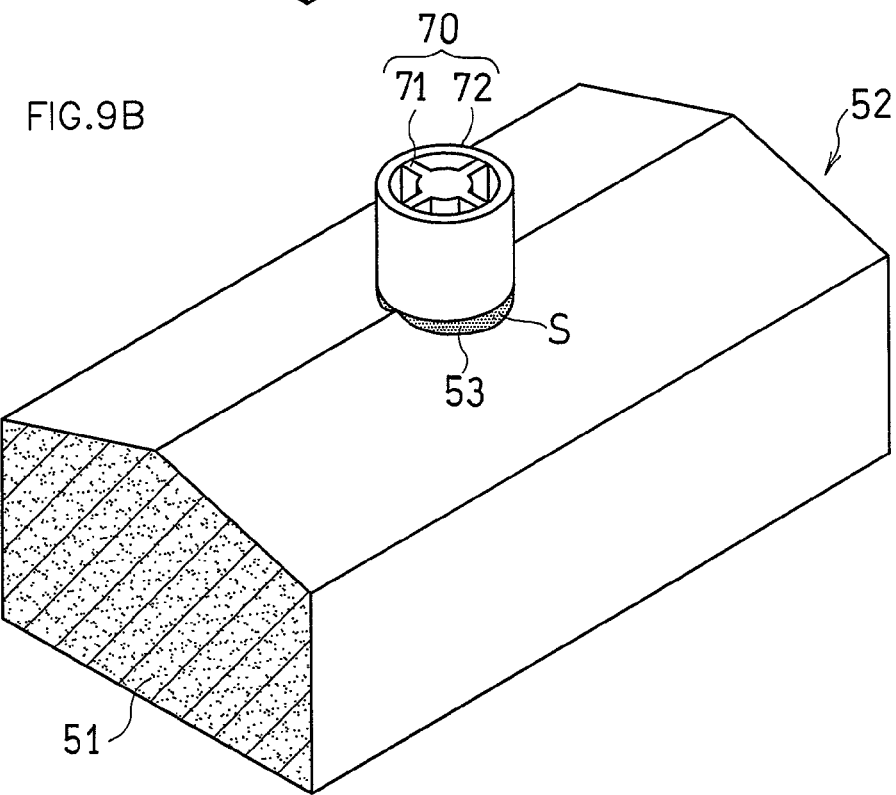

Then, in the order from step 4 of FIG. 8B to step 6 of FIG. 9B, a first core 70 having the shape of the fitting hole 14, the shape of the slit 13s and the shape of the groove 15 forming the allowance portion 15 as shown in FIG. 9B is attached to the replica 60 of FIG. 8B, thereby producing a matrix 52 of the denture base 10 of FIG. 9B.

Figure 8C:
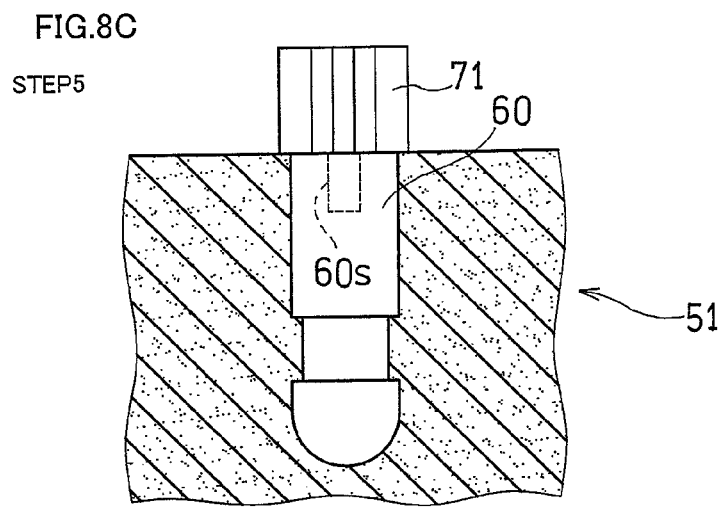

In order to produce the matrix 52 from the male mold 51 of FIG. 8B, a metal first part 71 having the shape of the fitting hole 14 and the slit 13s and forming a part of the first core 70 is first screwed and attached into a female screw 60s of the replica 60 as shown in step 5 of FIG. 8C. After the attachment of the first part 71, a second part 72 having the shape of the groove 15 and forming the other part of the first core 70 is attached over the first part 71 as shown in FIG. 9A.

Now, although a gap S to be an undercut in the molded product is formed between the end surface of the second part 72 and the surface of the male mold 51, as shown in FIG. 9B, the shape of the first core 70 of the matrix 52 is corrected by filling the gap S with the filler 53. Note that the filler 53 may be a resin such as a silicone resin or an epoxy resin, a plaster, a clay, etc., as well as a wax. Note that the second part 72 is preferably provided with a rotation preventing means, such as grooves 72e into which the blade portions 71A of the first part 71 fit. Such grooves 72e prevent the second part 72 from rotating, and prevents the portion formed by the filler 53 from positionally shifting with respect to the male mold 51.

Then, the matrix 52 is wrapped around by a self-hardening resin to produce, from the matrix 52, a resin mold 54 of a self-hardening resin having a groove 15A corresponding to the groove 15, as shown in FIG. 10. Note that the resin mold 54 has holes 14A and 17A corresponding to the fitting hole 14 and the slit 13s.

Figure 11:
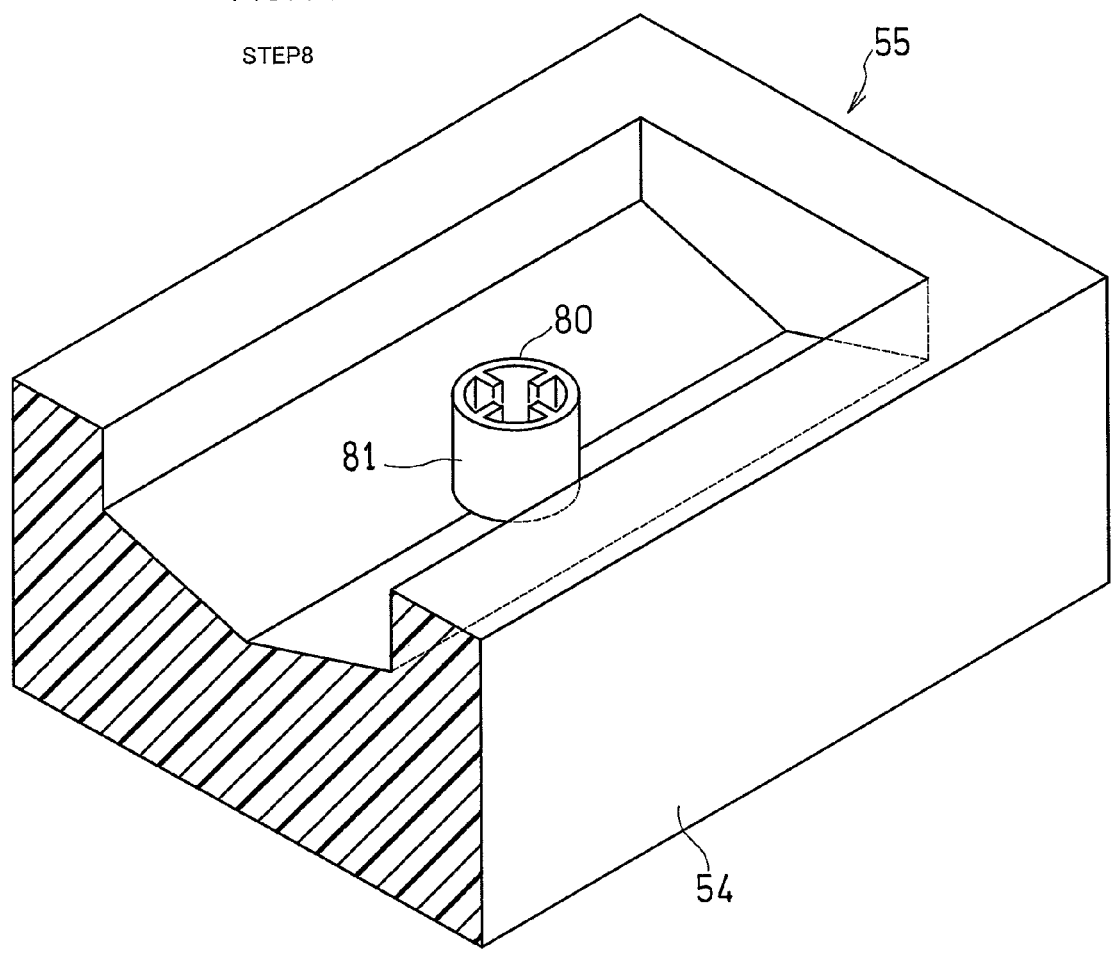
FIG. 11 is a perspective view showing step 8.

Then, a second core 80 is attached to the groove 15A of the resin mold 54 as shown in step 7 of FIG. 10 to produce a model 55 with a portion 81 of the second core 80 projecting from the resin mold 54 as shown in step 8 of FIG. 11. Note that the second core 80 has the shape corresponding to the groove 15 and the slit 13s.

Figure 12A:
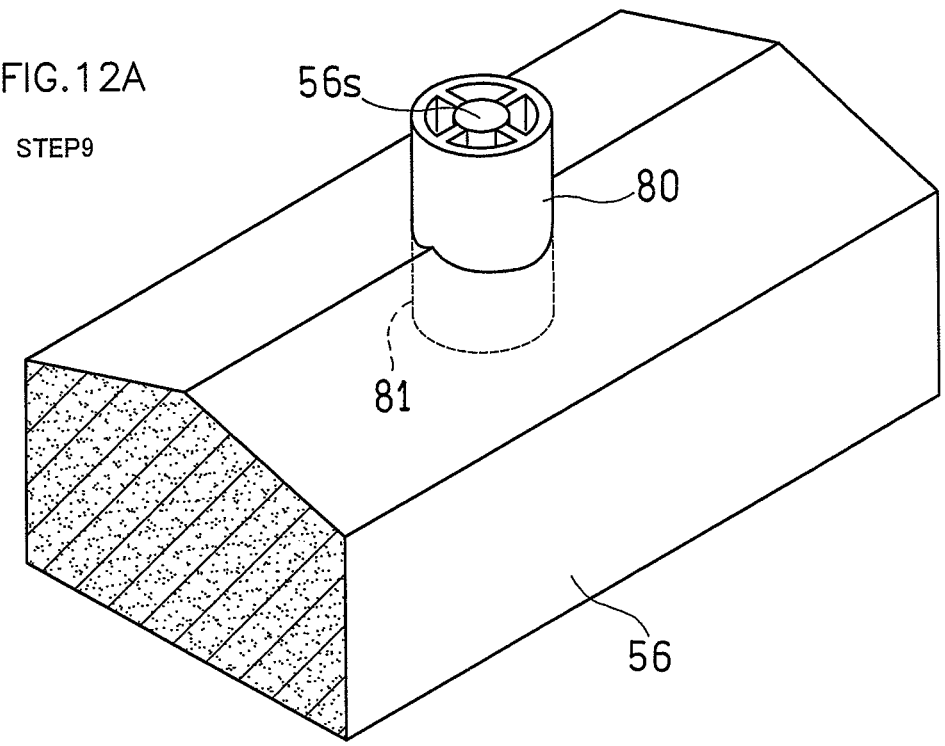
FIGS. 12A and 12B are perspective views showing steps 9 and 10, respectively.

Then, a plaster is poured into the depressed portion of the model 55 of FIG. 11 and then allowed to set, thereby producing a plaster mold 56 with the portion 81 of the second core 80 integrally buried in the plaster as shown in step 9 of FIG. 12A. Note that a generally columnar portion 56s corresponding to the hole 14A of FIG. 10 is integrally formed with the plaster mold 56.

Figure 12B:
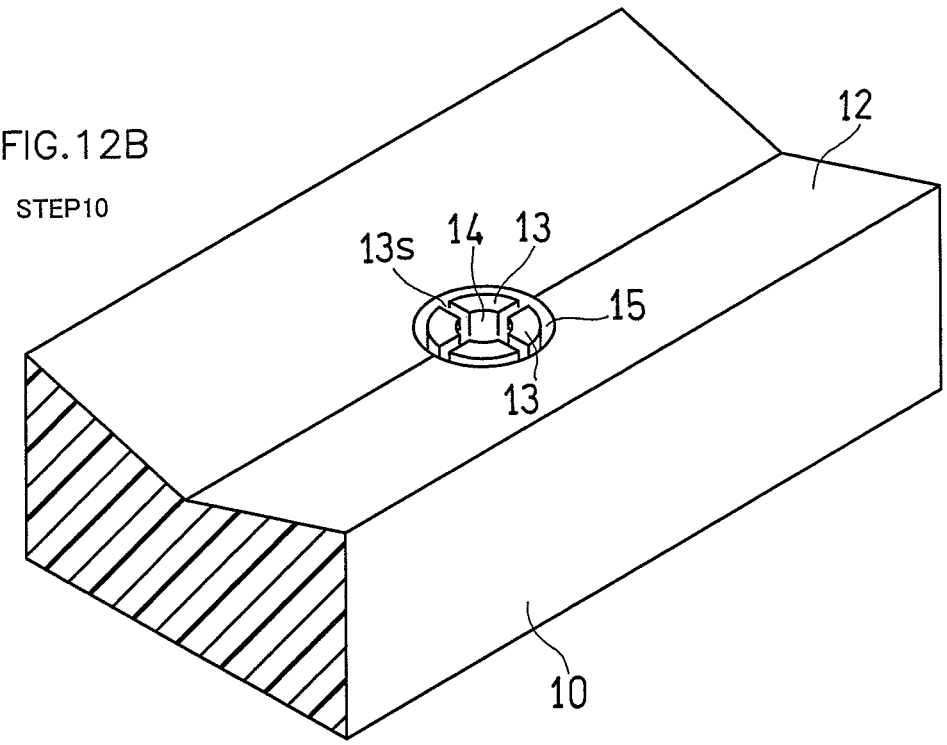

Then, the nylon denture base 10 is molded from the plaster mold 56 of FIG. 12A. Thus, the nylon denture base 10 of FIG. 12B is obtained from the matrix 52 of the denture base 10 of FIG. 9B. Thus, the burden on the dentist and the patient is reduced.

With the denture 1 thus produced, it is possible to correct or amend the fit of the engagement piece member 13 to the abutment 3 in order to enhance the wearability through a procedure as follows.

First, the denture 1 is worn and used by the patient over a short period of about 1 to 3 weeks or over a long period of some years. Then, the dentist asks the patient of the fit, and the denture 1 is taken out from the patient, after which the dentist heats the engagement piece members 13. With the fit taken into consideration, the heated engagement piece members 13 are deformed. The deformed engagement piece members 13 are cooled, after which the denture 1 is placed back in the patient.

The wearability is improved by repeating the correcting or amending operation.

The improvement of the wearability through the correcting operation is obtained also when only one engagement piece member 13 of FIG. 1 is provided, or the engagement piece member 13 is a completely continuous loop of FIG. 17B to be described below.

However, where the upper or lower end portion of the engagement piece member 13 is continuous with the main body 12, the engagement piece member 13 extends in the vertical direction Z from the end portion 13a of the engagement piece member 13, and the engagement piece member 13 is provided around the abutment 3 as a plurality of pieces separated from one another in the circumferential direction of the abutment 3, as shown in FIG. 6A, the engagement piece member 13 can easily be deformed, thereby facilitating the correcting operation and allowing for correction over a wide range.

With the method described above, step 6A of FIGS. 13A and 13B may be employed instead of step 6 of FIGS. 9A and 9B. That is, a cylindrical groove 15B may be formed in the plaster portion 51a of the male mold 51 of FIG. 13A, and the second part 72 having a cylindrical body may be inserted into the groove 15B.

Figure 14A:
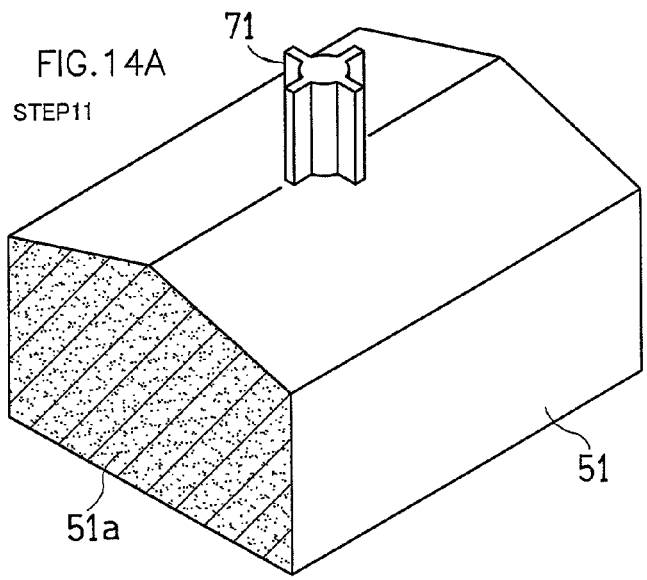
FIGS. 14A, 14B and 14C are perspective views showing different steps 11, 12 and 13, replacing the steps 6 to 10, in a third method.
Figure 14B:
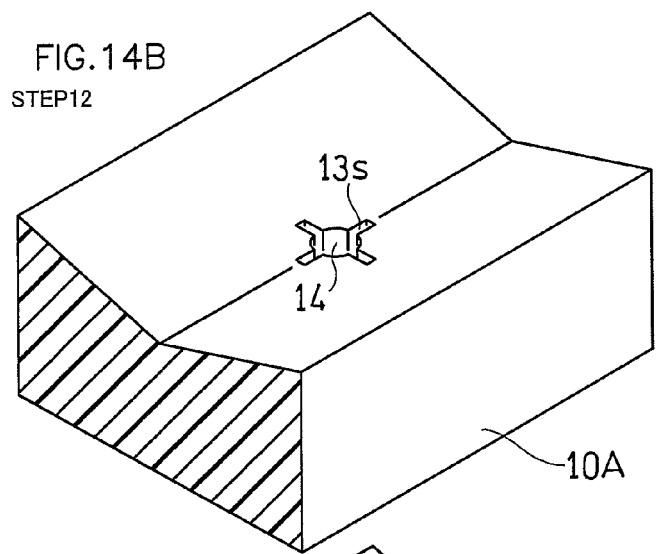
Figure 14C:
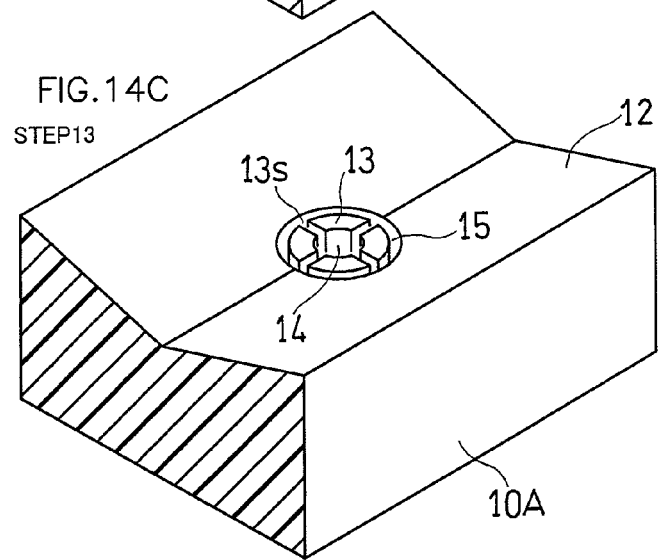
Figure 15A:
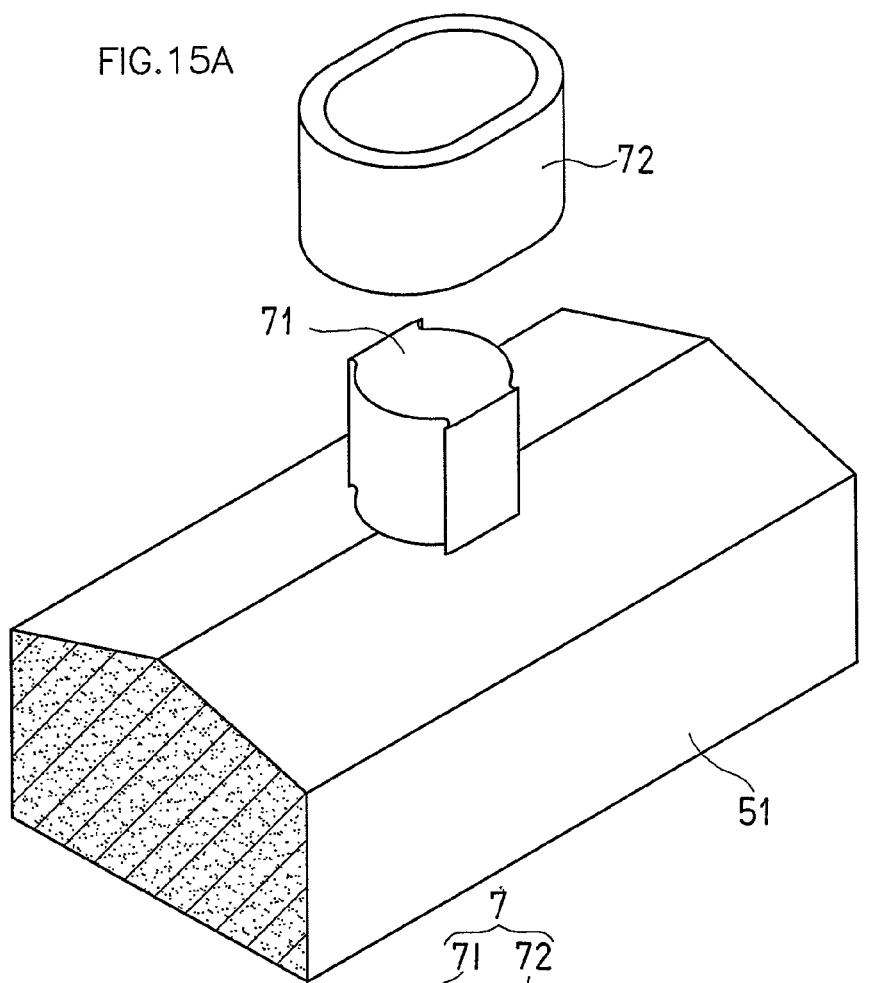
FIGS. 15A and 15B are perspective views showing step 6B, corresponding to the step 6, where there are two engagement piece members.
Figure 15B:
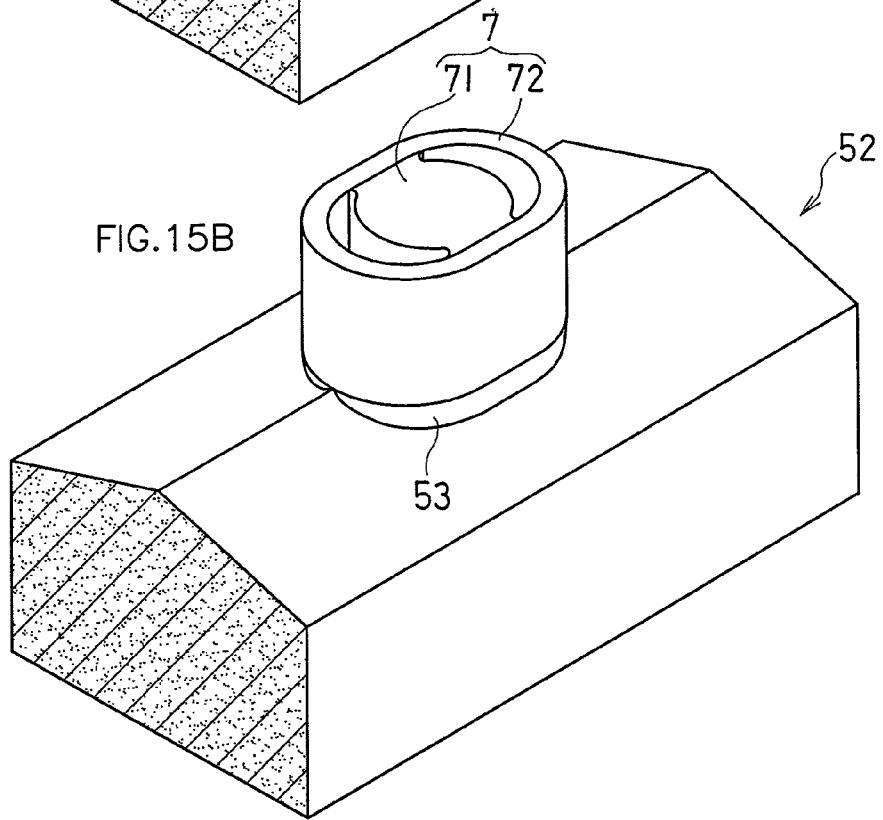
Figure 16A:
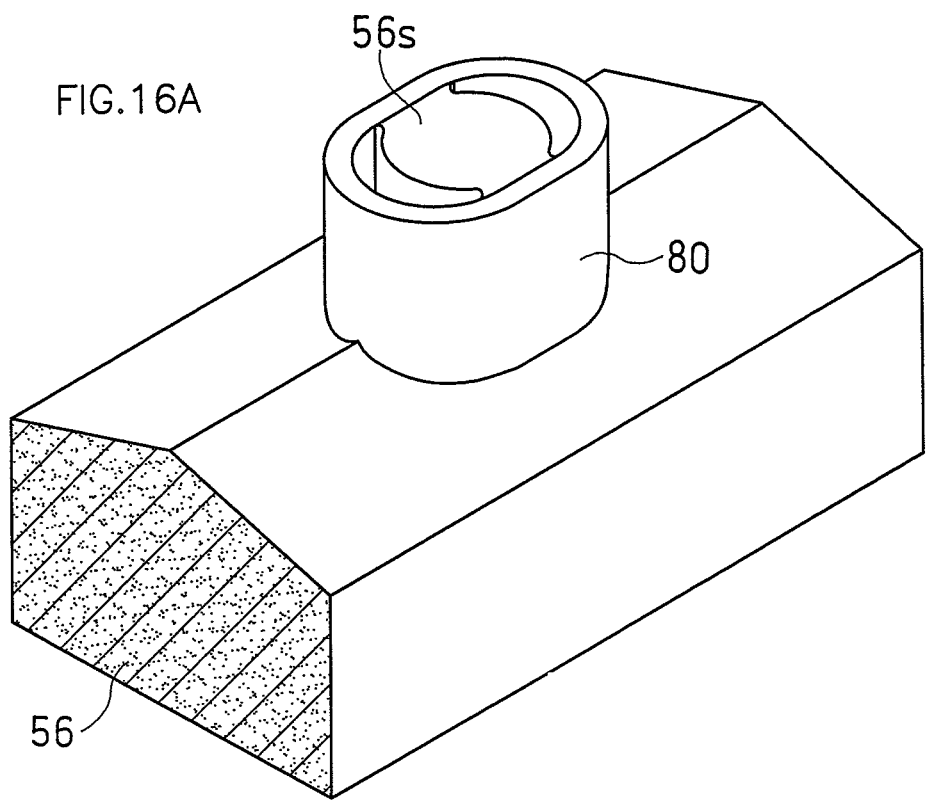
FIGS. 16A and 16B are perspective views showing step 9B and step 10B, respectively, corresponding to the steps 9 and 10.
Figure 16B:
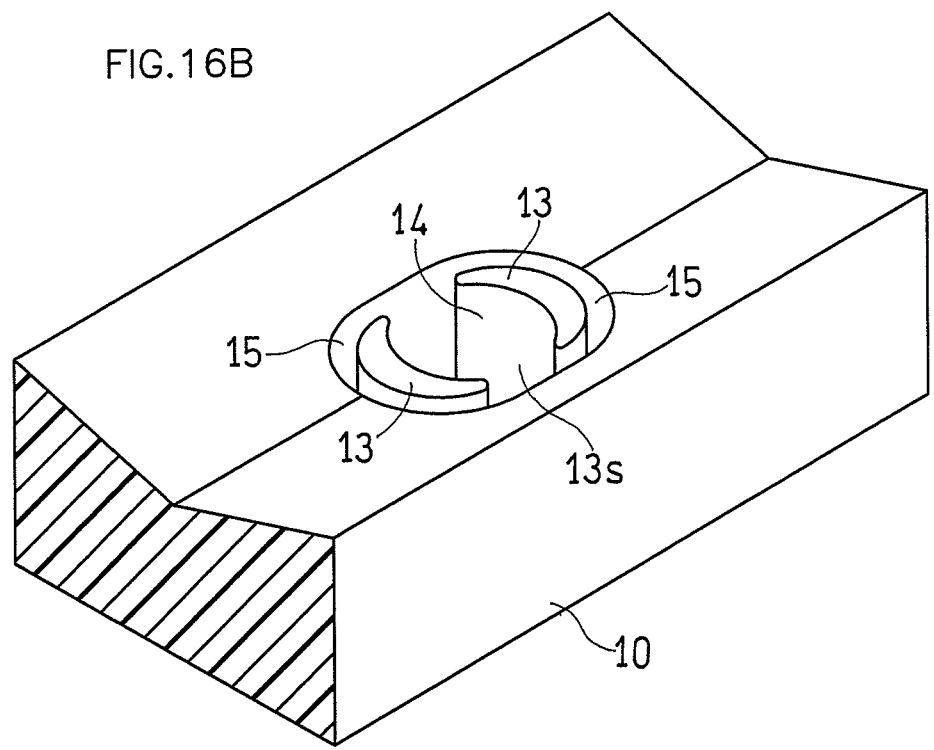

Steps 11 to 13 of FIGS. 14A to 14C may be employed instead of step 6 of FIG. 9A to step 10 of FIG. 12B. In such a case, a semi-finished product 10A made of a nylon resin of FIG. 14B is produced in a state where the first part 71 of the first core is attached to the male mold 51 of FIG. 14A, and the groove 15 is cut in the semi-finished product 10A.

Where a pair of grooves 15 and a pair of engagement piece members 13 are provided, a core or a mold shaped as shown in FIGS. 15A and 15B may be employed instead of the shape of FIGS. 9A and 9B. In such a case, the plaster mold 56 and the denture base 10 shaped as shown in FIGS. 16A and 16B are obtained instead of the shapes of the plaster mold 56 and the denture base 10 of FIGS. 12A and 12B.

FIGS. 17A to 19B show another embodiment of the production method.

Figure 17A:
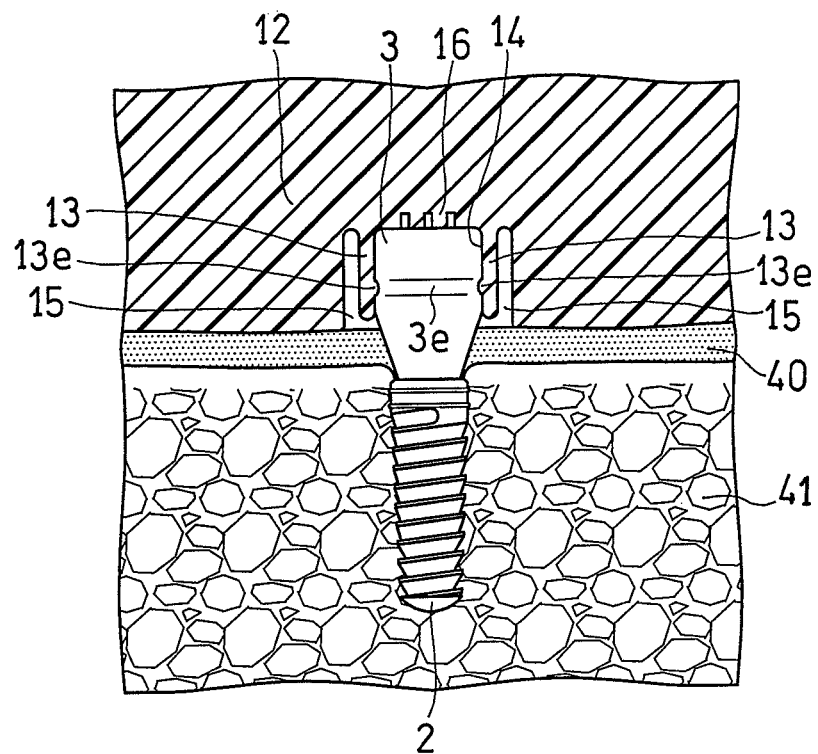
FIGS. 17A and 17B are an enlarged longitudinal cross-sectional view and a cross-sectional plan view, respectively, of an important part showing a fourth method for producing a denture of the present system according to Embodiment 3.
Figure 17B:
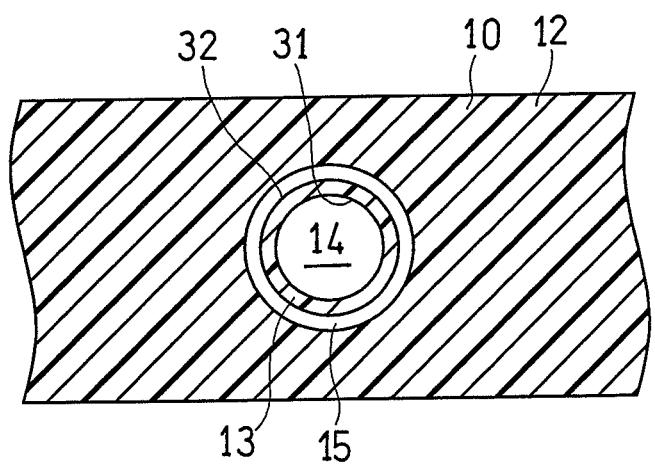

As shown in FIG. 17A, in the state of an intermediate product of the present embodiment, the engagement piece member 13 has an endlessly continuous cylindrical shape, and there are provided no slits 13s connecting together the circular fitting hole 14 and the cylindrical groove 15.

In the case of this embodiment, the second core 80 of FIG. 18 is used instead of the second core 80 of FIG. 10. The second core 80 includes a buried portion (portion) 81, a columnar portion 82 to be later buried in the plaster mold 56 (FIG. 19A) and fitted to the hole 14A, a cylindrical portion 83 to be fitted to the groove 15A, and a cover plate 84 formed integral with one another.

Figure 19A:
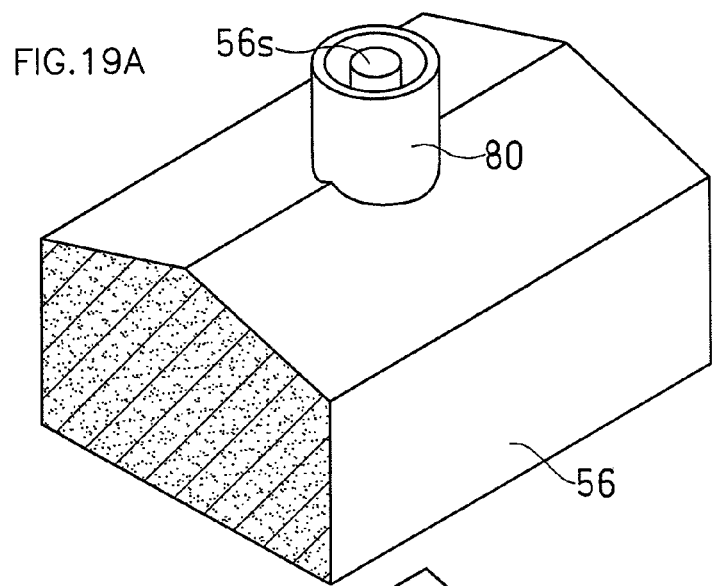
FIGS. 19A, 19B and 19C are perspective views showing steps 21, 22 and 23, respectively.
Figure 19B:
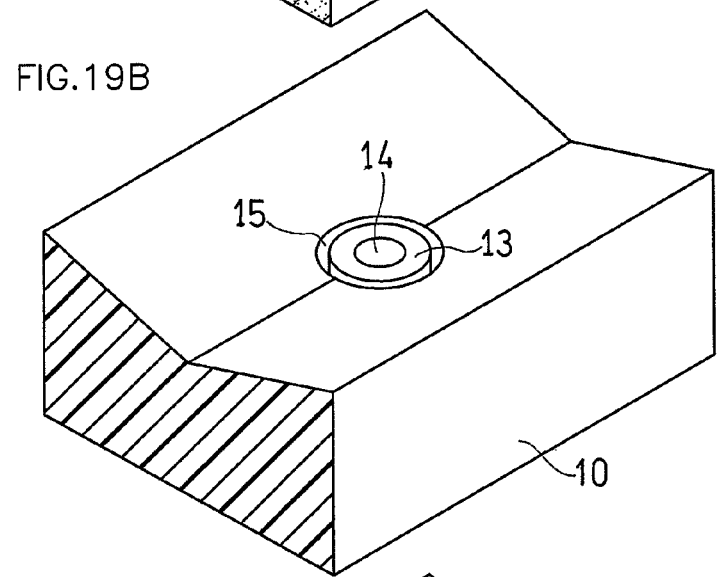
Figure 19C:
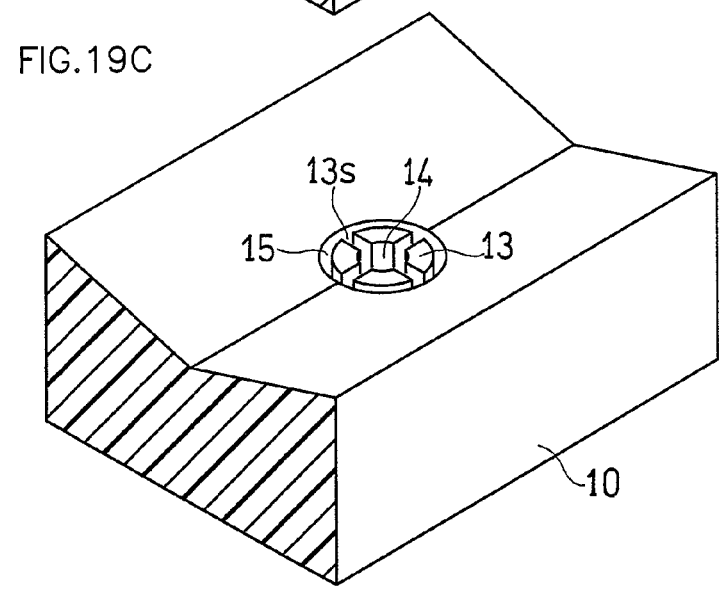

In the case of this embodiment, the plaster mold 56 and the denture base 10 shown in FIGS. 19A and 19B are obtained instead of the plaster mold 56 and the denture base 10 shown in step 9 of FIGS. 12A and 12B and FIG. 10. Then, as shown in FIG. 19C, the denture base 10 is processed to have areas to be the slits 13s, thereby obtaining the denture base 10 having the slits 13s.

Figure 20A:
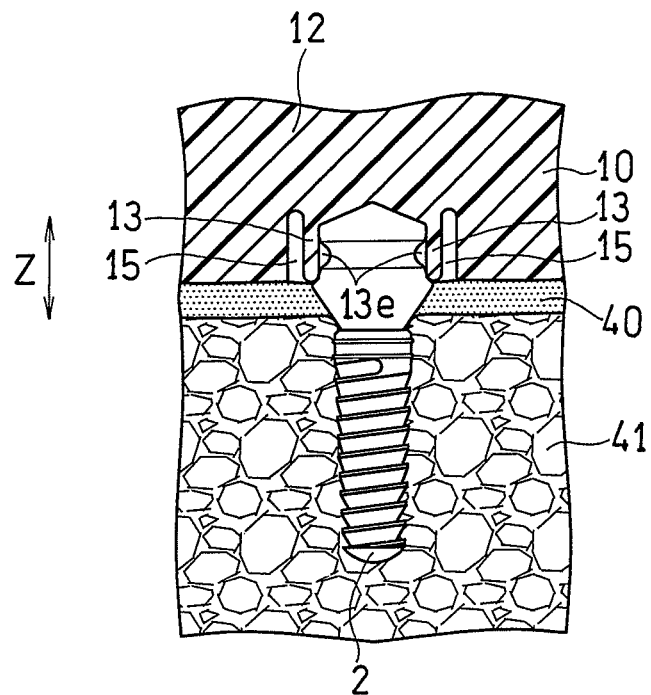
FIGS. 20A and 20B are an enlarged longitudinal cross-sectional view and a cross-sectional plan view, respectively, of an important part of the present system according to Embodiment 4.
Figure 20B:
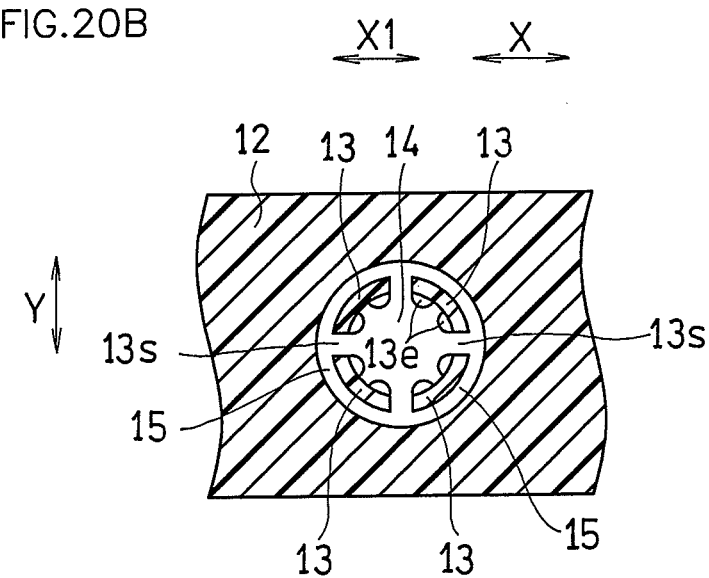

FIGS. 20A and 20B show still another embodiment.

As shown in these figures, the top surface of the abutment 3 may have a conic shape. On the other hand, the top surface or the bottom surface of the fitting hole 14 may have a shape that conforms with the top surface of the abutment 3.

FIGS. 21A to 27C show still another embodiment.

As shown in FIGS. 27A to 27C, in this embodiment, the engagement piece 13P is provided separately from the denture base 10. The denture base 10 and the engagement piece 13P are formed by a nylon-based thermoplastic resin of the same type or resins of different types. A coupling layer 19 of a two-component autopolymerizing resin is interposed between the denture base 10 and the engagement piece 13P, whereby the denture base 10 and the engagement piece 13P are coupled together and formed integral and continuous together.

In FIGS. 27A and 27B, the engagement piece 13P is formed in a generally cylindrical shape with a bottom, i.e., a cup shape, having a plurality of (e.g., four) slits 13s and engagement piece members 13, with a lid portion 13c for coupling together the plurality of engagement piece members 13. Note that each engagement piece member 13 has an engagement element 13e.

The lid portion 13c covers the top portion (top) 3t of the abutment 3. In FIG. 27A, anchor grooves 13g and 10g are formed in the lid portion 13c and an area of the denture base 10 opposing the lid portion 13c. The space between the lid portion 13c and the denture base 10 and the anchor grooves 13g and 10g are filled with the autopolymerizing resin of the coupling layer 19.

Note that the anchor grooves 13g of the denture base 10 are formed in the inner surface of an accommodating depressed portion 10c.

A deep hole 10h to be the gate for pouring the resin is formed in the denture base 10, and the deep hole 10h is also filled with the resin. Note that the deep hole 10h connects the outer surface of the denture base 10 with the deep end of the accommodating depressed portion 10c.

The accommodating depressed portion 10c having a columnar shape for accommodating the engagement piece 13P therein is formed in the denture base 10. The accommodating depressed portion 10c is defined by the third surface 33 of the denture base 10. The third surface 33 opposes the second surface 32.

Note that the slits 13s run through the engagement piece 13P in the radial direction from the first surface 31 to the second surface 32.

Next, a method for producing the denture 1 of the embodiment will be described.

Figure 21B:
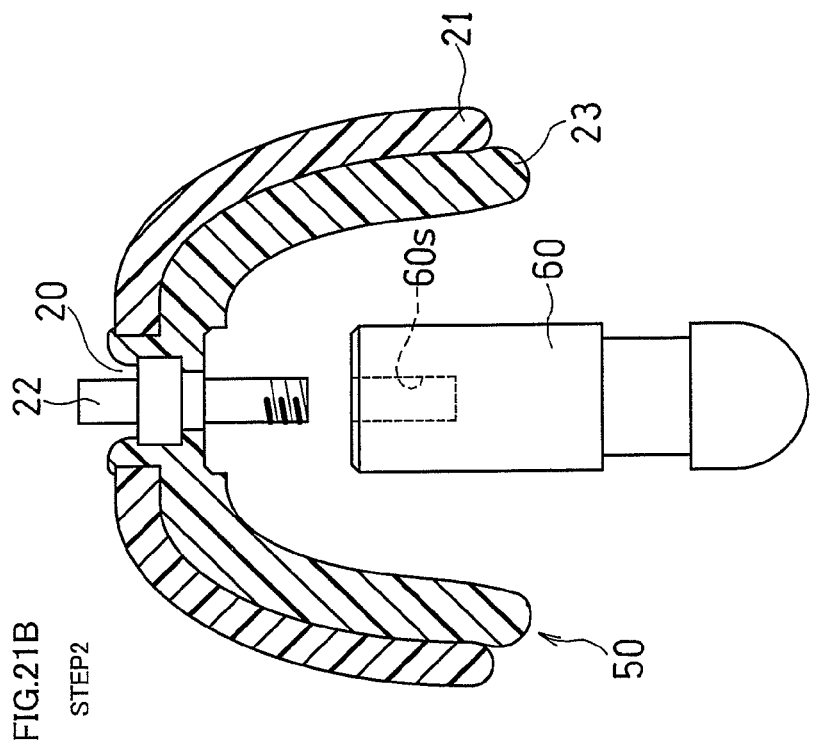
FIGS. 21A and 21B are cross-sectional views showing steps 1 and 2, respectively, of a method for producing a denture according to Embodiment 5.
Figure 21A:
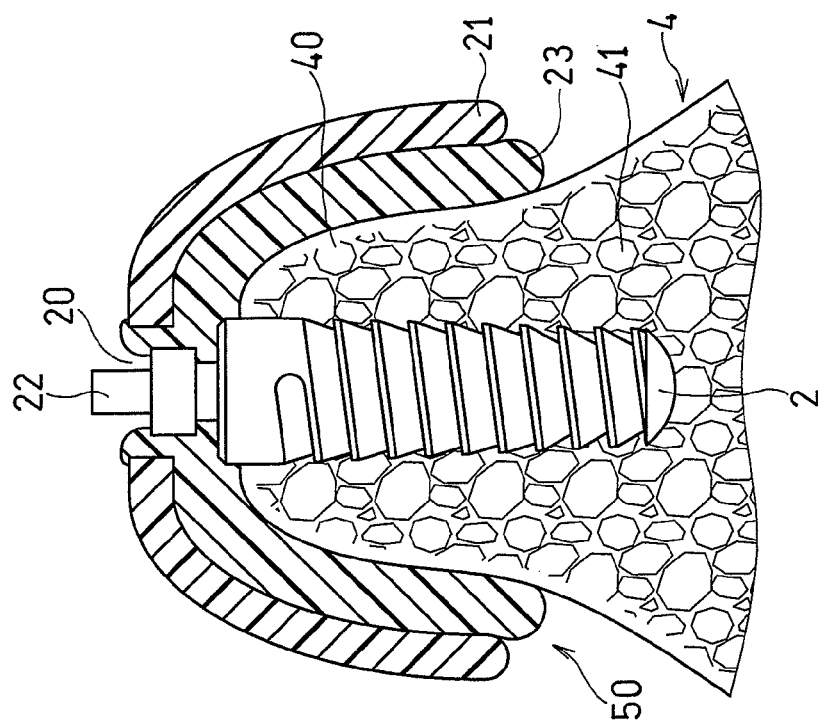
Figure 22B:
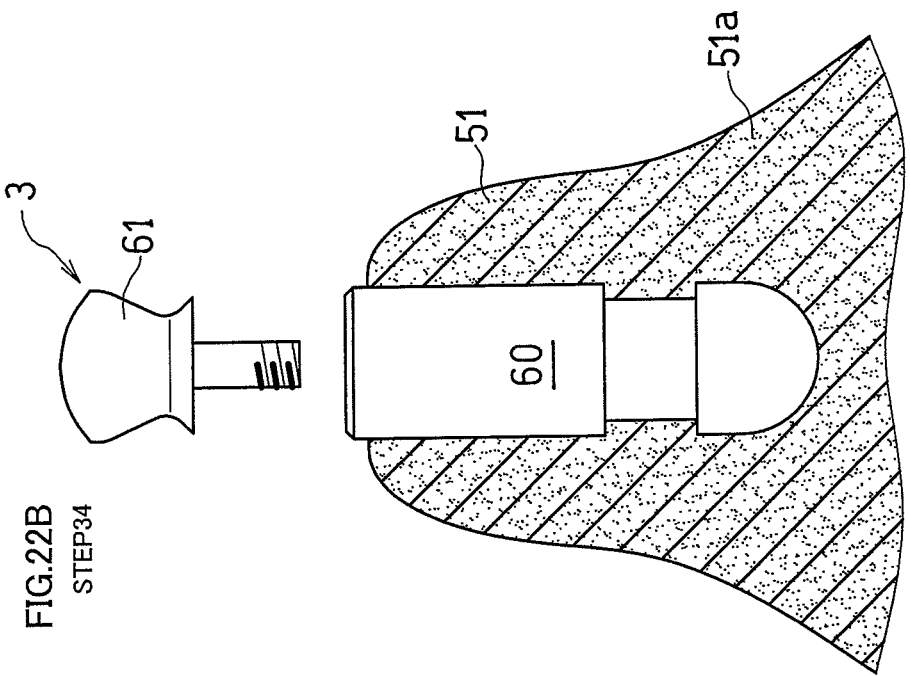
FIGS. 22A and 22B are cross-sectional views showing steps 3 and 34, respectively.
Figure 22A:
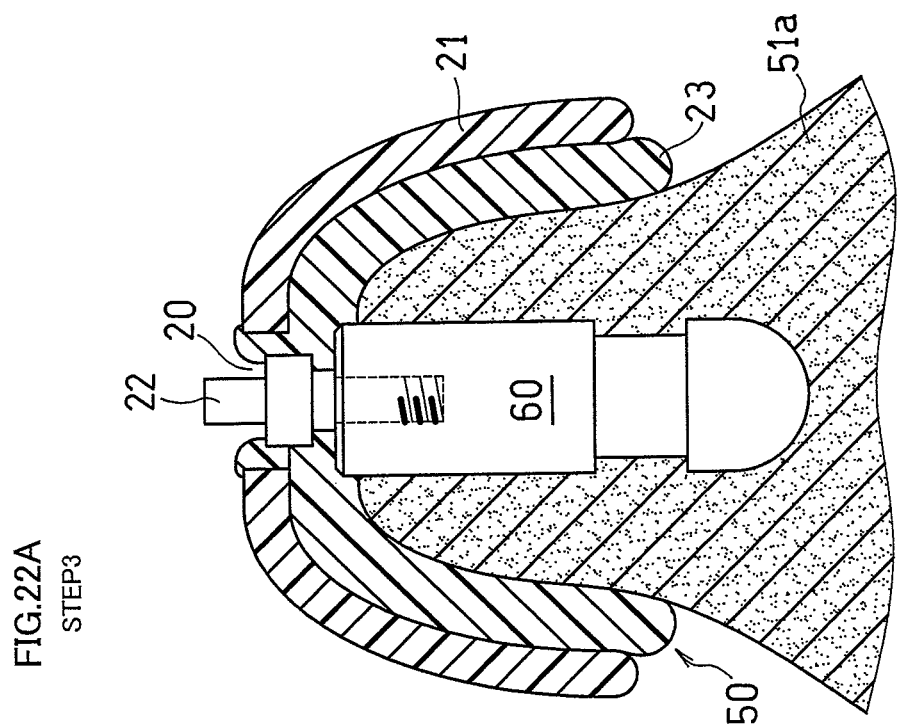

First, the female mold 50 of FIG. 22A is produced through step 1, step 2 and step 3 of FIGS. 21A, 21B and 22A. These steps 1 to 3 are similar to steps 1 to 3 of FIGS. 7A, 7B and 8A, and will not be described below.

Then, in the order from steps 34 to 40 of FIGS. 22B to 26A, the denture base 10 having the accommodating depressed portion 10c forming the allowance portion 15 of FIG. 27A is formed. The method for forming the denture base 10 will now be described.

Figure 23B:
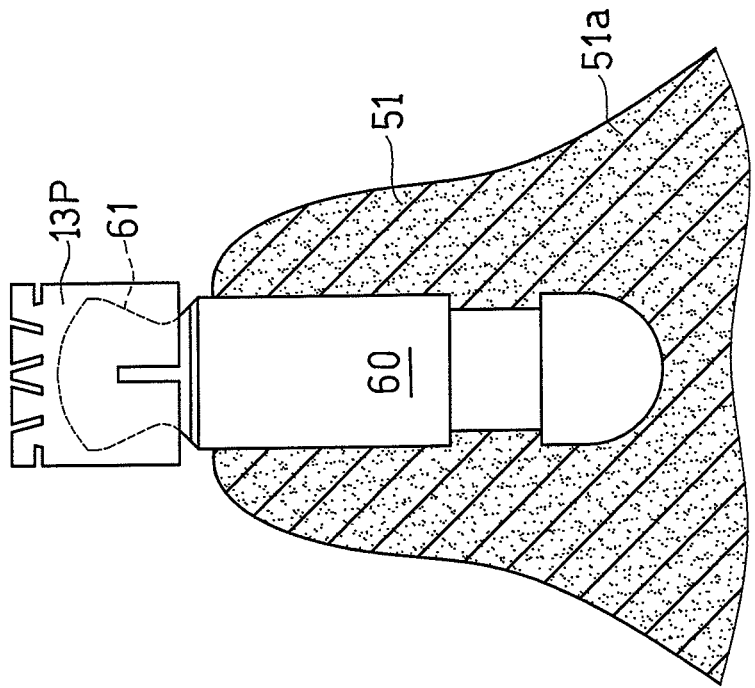
FIGS. 23A and 23B are cross-sectional views showing step 35, respectively.
Figure 23A:
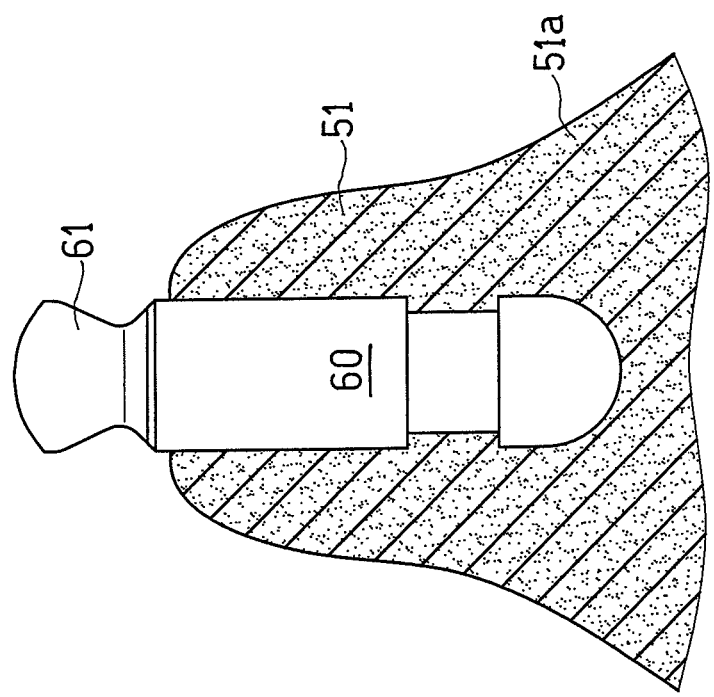

In order to form the denture base 10, a second replica 61 of the abutment 3 is attached to a first replica 60 buried in the male mold 51 as shown in FIG. 23A in step 34 shown in FIG. 22B following step 3. At the time of this attachment, the engagement piece members 13 of the engagement piece 13P are elastically deformed to engage with the engaged groove 3e of the abutment 3. Then, in step 35 of FIG. 23B, the engagement piece 13P is fitted to the second replica 61. In this state, the gap S to be an undercut is present between the engagement piece 13P and the male mold 51.

After the fitting, as shown in step 36 of FIG. 24A, a core 90 is arranged around the engagement piece 13P in order to form the allowance portion 15 (FIG. 27A) of the engagement piece member 13. In this example, the core 90 is formed by a wax covering the lid portion 13c and the circumference of the engagement piece 13P and filling the gap S. Thus, the male mold 51 having the shape of the projecting portion 15P corresponding to the allowance portion 15 and the shape of the oral cavity is produced from the female mold 50 of FIG. 22A.

Note that the core 90 may be formed by a cup-shaped metal or resin core covering the circumference of the engagement piece 13P and the lid portion 13c, and the filler (wax) 53 filling the gap S below the engagement piece 13P.

The wax forming the core 90 serves also as the filler 53 filling the gap (undercut) S formed on the surface between the engagement piece 13P and the male mold 51. The wax forming the core 90 fills the anchor groove 13g formed in the lid portion 13c of the engagement piece 13P.

The outer surface of the core 90 (the projecting portion 15P) thus formed has a generally columnar shape.

After the core 90 is formed, a plaster mold 56A shown in step 37 of FIG. 24B is obtained from the male mold 51 of FIG. 24A. The denture base 10 having the artificial tooth 11 is obtained by using the plaster mold 56A and a well-known female mold (not shown). That is, the denture base 10 having the shape of the hole 1511 forming the allowance portion 15 is obtained from the male mold 51.

Figure 25B:
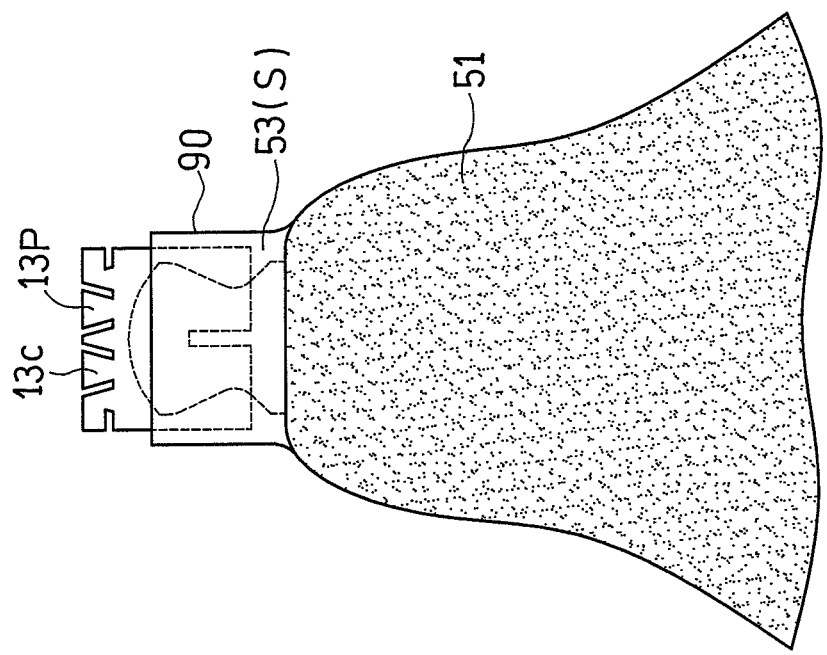
FIGS. 25A and 25B are cross-sectional views showing steps 38 and 39, respectively.
Figure 25A:
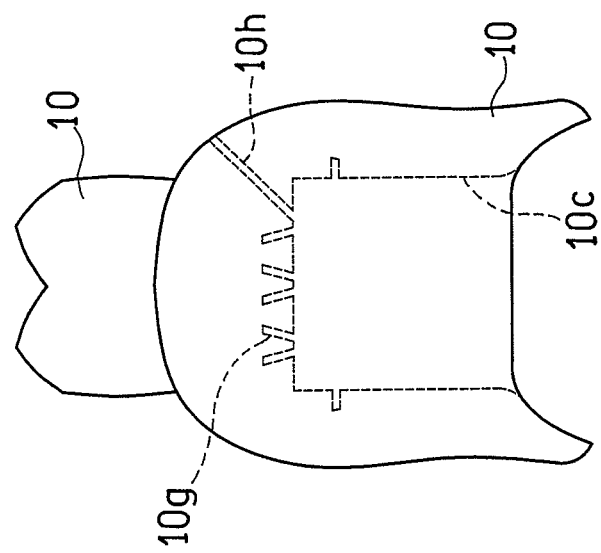

Then, the denture base 10 of FIG. 24B is removed from the plaster mold 56A, and the anchor grooves 10g and the deep hole 10h are formed in the denture base 10 as shown in step 38 of FIG. 25A.

On the other hand, an area of the wax corresponding to the lid portion of the male mold 51 obtained in step 36 of FIG. 24A is removed as shown in step 39 of FIG. 25B, thereby exposing the lid portion 13c of the engagement piece 13P. Then, as shown in step 40 of FIG. 26A, the denture base 10 obtained in 24B described above is attached to the engagement piece 13P, which has been exposed as some wax has been removed.

In the state shown in FIG. 26A, a gap 19s corresponding to the coupling layer 19 is formed between the engagement piece 13P and the denture base 10. Then, as shown in step 41 of FIG. 26B, a well-known two-component autopolymerizing resin is poured into the gap 19s and the anchor grooves 10g and 13g through the deep hole 10h.

As the polymerizing resin sets, the denture base 10 and the engagement piece 13P become integral with each other with the coupling layer 19 interposed therebetween while the engagement piece 13P and the denture base 10 are spaced apart from each other over the allowance portion 15. That is, the denture base 10 and the engagement piece 13P become integral with each other with the coupling layer 19 interposed therebetween while ensuring a moving range of the engagement piece member 13 by virtue of the remaining portion of the core 70. After the polymerizing resin sets, the denture base 10 integral with the engagement piece 13P is removed from the male mold 51, thus obtaining the denture 1 of FIG. 27A.

The denture 1 thus produced by the technician is placed in the oral cavity of the patient so that the fitting hole 14 of the engagement piece 13P fits over the abutment 3 while the denture base 10 is in contact with the gum 40 as shown in FIG. 27C.

At the time of this attachment, the engagement piece members 13 of the engagement piece 13P are elastically deformed to engage with the engaged groove 3e of the abutment 3.

FIGS. 28A to 29B show other examples of the denture 1.

In the examples of FIGS. 28A and 28B, the engagement piece member 13 and the denture base 10 are formed by a nylon-based thermoplastic resin, and the lid portion 13c of the engagement piece 13P and the denture base 10 are welded with each other in the accommodating depressed portion 10c. In these examples, the coupling step is performed by welding the engagement piece 13P and the denture base 10 with each other.

Such welding may be done by induction heating using a high frequency. In addition to the welding, the engagement piece 13P and the denture base 10 may be engaged with each other as shown in FIG. 28B.

Figure 29A:
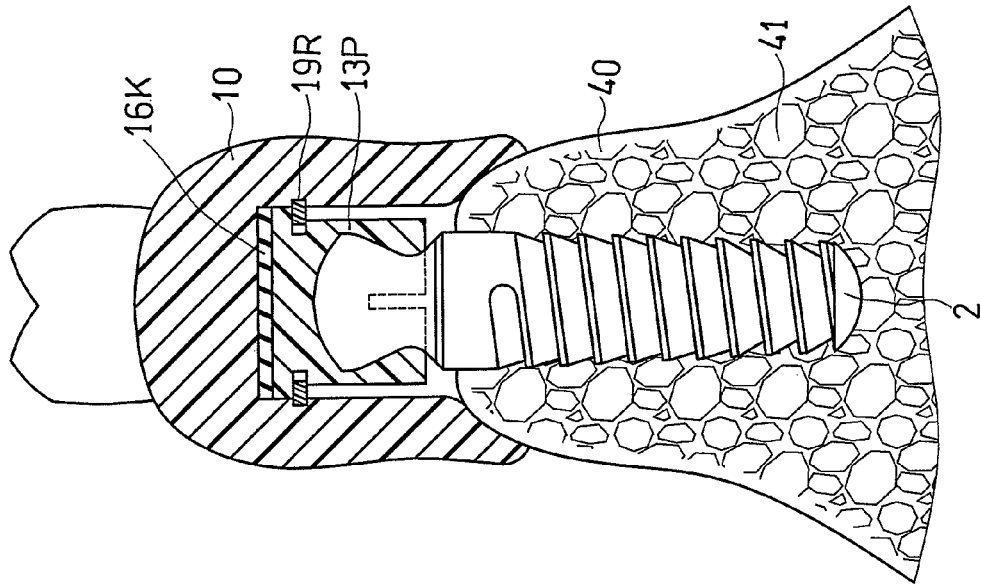
FIGS. 29A and 29B are cross-sectional views showing dentures according to Embodiments 8 and 9, respectively.
Figure 29B:
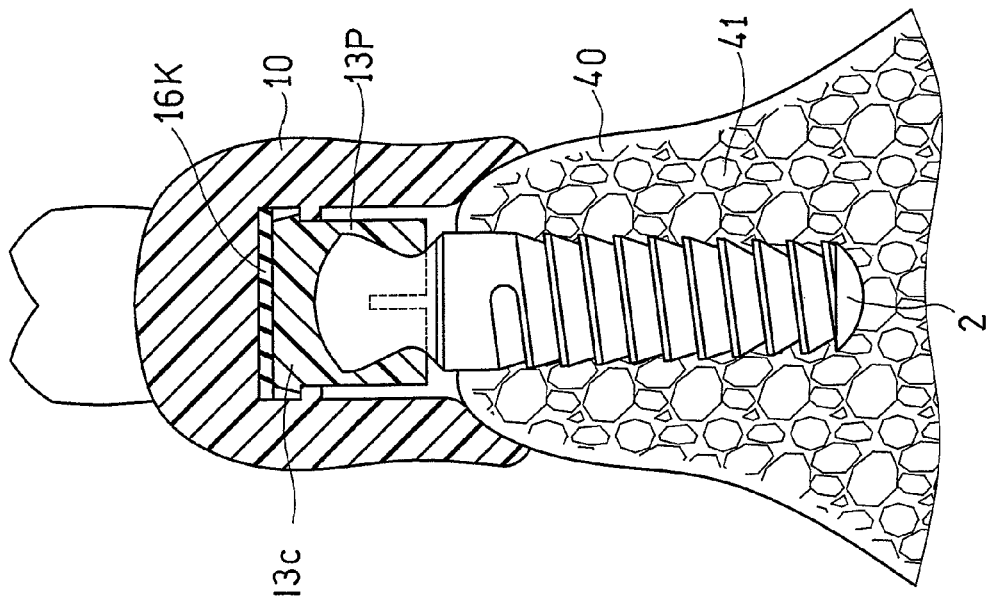

In the example of FIG. 29A or 29B, the engagement piece member 13 is held by being directly or indirectly engaged with the denture base 10. In these examples, the coupling step is performed by directly or indirectly engaging the engagement piece 13P and the denture base 10 with each other.

In the examples of FIGS. 29A and 29B, a cushion 16K such as a silicone gel may be inserted between the lid portion 13c of the engagement piece 13P and the denture base 10.

Note that in FIG. 29B, the engagement piece 13P and the denture base 10 are engaged with each other with a C-shaped engagement ring 19R therebetween.

Figure 30:
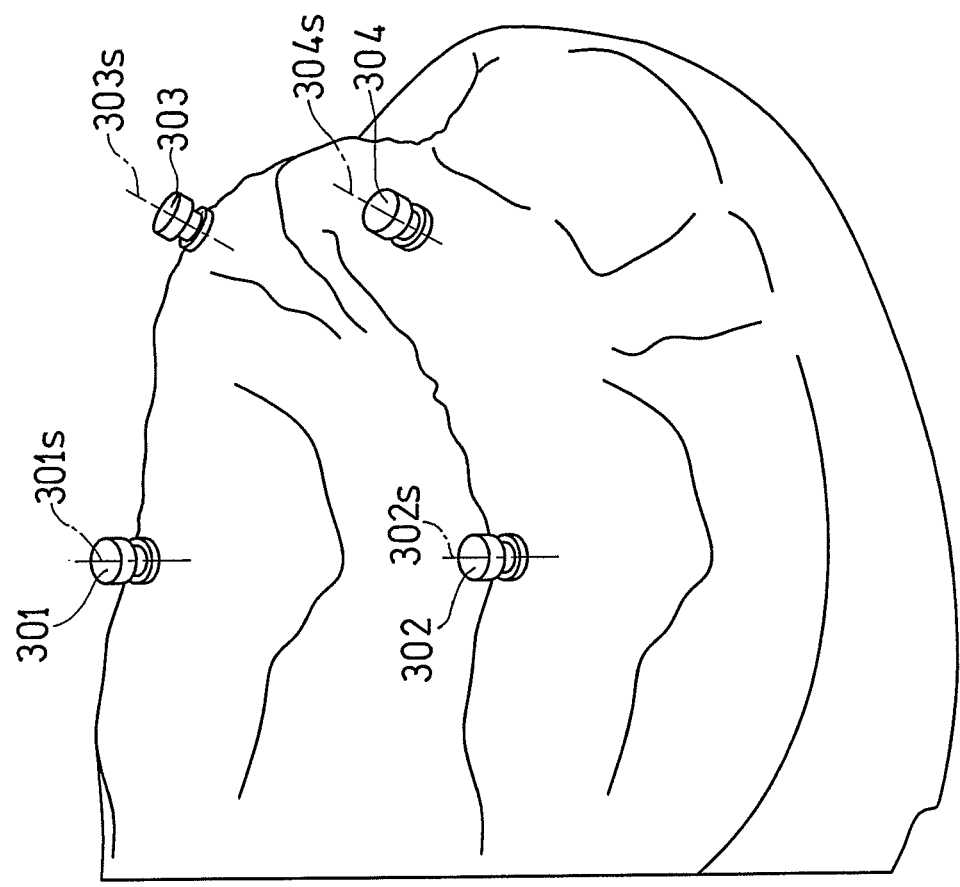
FIG. 30 is a perspective view showing an example of an arrangement of abutments.

FIG. 30 is a perspective view of a model showing an arrangement of the abutments 3 with respect to the oral cavity.

In this figure, a pair of abutments 301 and 302 arranged on the back side has their axial lines 301s and 302s parallel to each other. A pair of abutments 303 and 304 arranged on the front side has their axial lines 303s and 304s parallel to each other. However, the axial lines 301s and 302s of the abutments 301 and 302 and the axial lines 303s and 304s of the abutments 303 and 304 are not parallel to each other but are arranged in a skew relationship with respect to each other.

In such a case, the engagement piece members 13 of the present denture system elastically deform, thereby enabling the realization of the denture 1 which fits to the four abutments 301 to 304.

In such a case, the denture 1 having a plurality of engagement piece members 13 and the denture 1 having a structure shown in FIGS. 4A and 4B have high applicability.

In the example to follow, a closed tray 21A is used instead of the open tray 21 having a window.

FIGS. 31A to 33D show an example of the production method.

First, as shown in step 51 of FIG. 31A, the dentist produces the female mold 50 of the oral cavity, with the fixture 2 buried therein and the abutment 3 coupled to the fixture 2, by using the tray 21A and a flexible impression material 23 (self-hardening resin) according to a well-known method. As the impression material 23 cures, the tray 21A and the impression material 23 are removed from the oral cavity, thus obtaining the female mold 50.

A plaster is poured into the obtained female mold 50 and the plaster sets, thereby producing the male mold 51 having the shape of the abutment 3 shown in step 52 of FIG. 31B and the shape of the oral cavity.

Note that since the impression material 23 is flexible, the female mold 50 and the male mold 51 can be released from each other even with the engaged groove 3e in the abutment 3.

Next, as shown in FIG. 32B, the cylindrical core 70 is attached over an area 51b of the male mold 51 corresponding to the abutment. While the core 70 is formed by, for example, a metal such as stainless, Teflon or ceramic, it is preferred to use a material that has a good heat resistance in the molding process and that can easily be released from the denture base 10.

As shown in FIGS. 32A and 32B, the core 70 includes a cylindrical portion 72A having a cylindrical shape, and a plurality of blade portions 71A provided at positions corresponding to the slits 13s and extending from the inner circumferential surface of the cylindrical portion 72A toward the center of the cylindrical portion 72A. The blade portion 71A forms a part of the slit 13s in the step of obtaining the denture base 10 to be described later.

The end of each blade portion 71A on the inner circumference side is close to, or in contact with, the area 51b.

An end face 70e of the core 70 on one side (the lower side in the figure) in the vertical direction that opposes the male mold 51 is in contact with an area 51c corresponding to the ridge of the gum, thereby forming the gap S to be an undercut between the end face 70e of the core 70 and the surface of the male mold 51, but the gap S is filled with the filler 53 to produce the matrix 52 in the present embodiment. In the present embodiment, the filler 53 may preferably be, for example, a ceramic material, such as a plaster, which can be easily molded and broken, and which can withstand the heat during the process of molding the denture base 10.

Then, an intermediate product of the denture base 10 having the artificial tooth 11 shown in step 54 of FIG. 32C is molded by a well-known method from the matrix 52. After the nylon of the denture base 10 sets, the male mold 51 and the filler 53 are crushed, and moreover the core 70 is pulled out of the intermediate product of the denture base 10.

Thus, an intermediate product of the denture base 10 shown in FIGS. 33A and 33B is obtained. The intermediate product includes a groove 130 formed therein to be a part of the slit 13s.

Then, in the area of the groove 130, the slit 13s of FIG. 33C is formed so that the fitting hole 14 and the allowance portion 15 are connected with each other. The slit 13s serves to make it easier for the engagement piece members 13 and 13 to be deformed independently of each other.

Thus, the nylon denture base 10 of FIG. 33C is obtained from the female mold 50 of FIG. 31A. Thus, the burden on the dentist and the patient is reduced.

FIGS. 34A to 36C show the structure and the production method of Embodiment 11.

In this example, a plurality of longitudinal grooves 3g are included on the abutment 3.

Figure 34A:
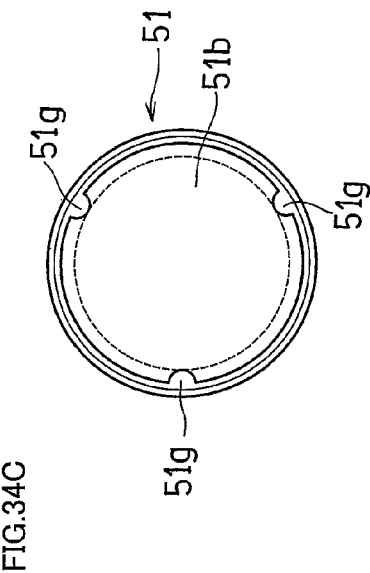
FIGS. 34A and 34B are a cross-sectional plan view and a longitudinal cross-sectional view, respectively, showing step 61 of a method for producing a denture according to Embodiment 11.
Figure 34C:
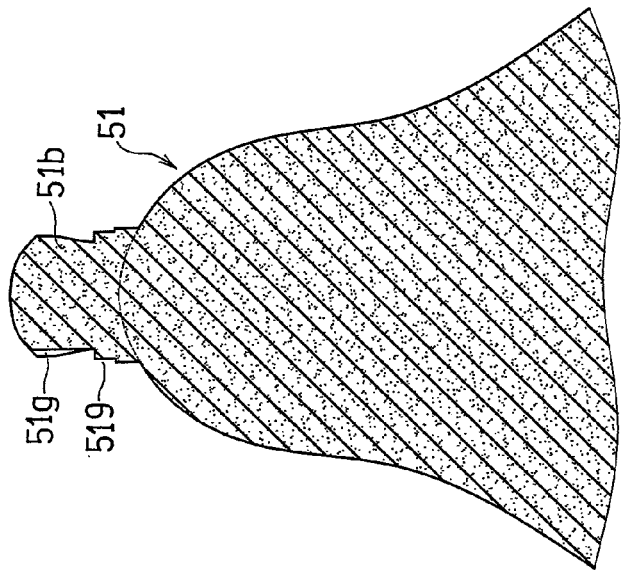
FIGS. 34C and 34D are a plan view and a longitudinal cross-sectional view, respectively, showing step 62.
Figure 34B:
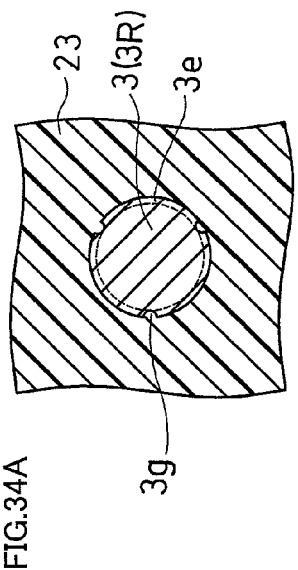

As shown in FIGS. 34A and 34B, the abutment 3 or a replica 3R thereof having a shape similar to that of the abutment 3 includes a male screw portion 3s to be screwed into a female screw 2s of the fixture 2, and a top 3t projecting from the fixture 2 over which the denture 1 is fitted through the fitting hole 14. Note that the top 3t is the upper end portion of the abutment 3 for the lower jaw, and the lower end portion of the abutment 3 for the upper jaw.

In FIG. 36C, the abutment 3 is provided with a cylindrical or spherical outer surface over which the denture base 10 and the engagement piece members 13 are fitted. Formed on the side surface of the abutment 3 are an engaged groove 3e and two, three or four longitudinal grooves 3g.

In FIG. 36C, the engaged groove 3e is formed in a circumferential shape between the top 3t and the male screw portion 3s. The engaged groove 3e is formed in a narrowed shape with which the engagement piece members 13 engage. The longitudinal grooves 3g are provided on the side surface of the abutment 3, and extending from the top 3t toward the male screw portion 3s, with the depth thereof being generally equal to or greater than that of the engaged groove 3e. The longitudinal grooves 3g are spaced apart from one another in the circumferential direction, and the number of longitudinal grooves 3g is the same as the number of slits 13s.

In FIG. 34B, the abutment 3 or the replica 3R is provided with the cylindrical outer circumferential surface 39 at a position closer to the fixture 2. The cylindrical outer circumferential surface 39 has an outer diameter that is greater than the outer diameter of the top 3t which projects from the fixture 2 and over which the denture 1 is fitted through the fitting hole 14 and that is smaller than the outer diameter of the fixture 2.

A C-shaped or ring-shaped positioning portion 79 is formed integral with a cylindrical portion 71A at the lower end portion of the cylindrical core 70 of FIGS. 35A and 35B. The positioning portion 79 is for positioning the core 70 with respect to the male mold 51 by being fitted over, while being in contact with, an area 519 of the male mold 51 corresponding to the cylindrical outer circumferential surface 39 (FIG. 34B).

In the present embodiment, steps 61 to 64 of FIGS. 34A to 35C are performed as are steps 51 to 54 of FIGS. 31A to 32C of the embodiment described above, thereby molding the denture base 10 of FIG. 35C.

Figure 34D:
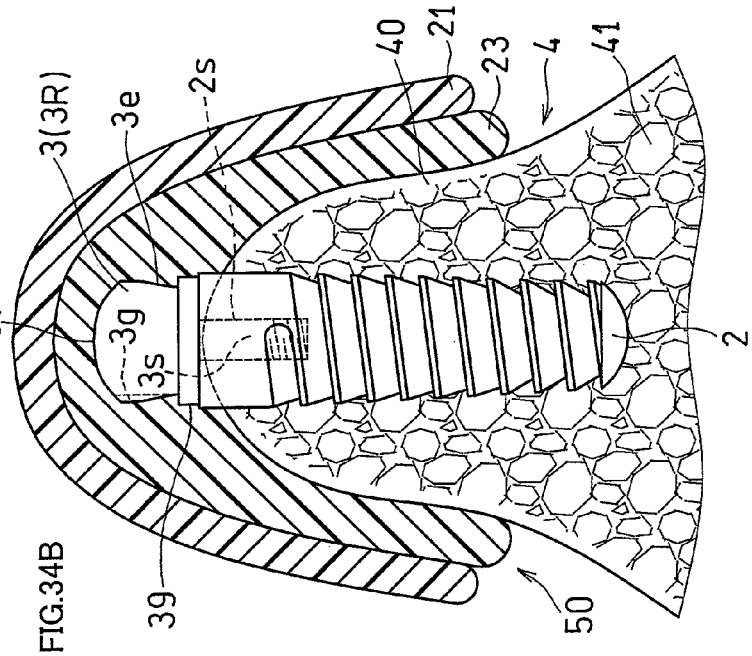

In step 62 of producing the male mold 51 of FIGS. 34C and 34D of the present embodiment, the longitudinal groove 51g, into which the projecting end of the blade portion 71A of FIG. 35A fits and which allows for up and down movement of the blade portion 71A when attaching the core 70, is formed in an area of the male mold 51 corresponding to the abutment, and in the attachment step shown in FIGS. 35A and 35B, the blade portion 71A of the core 70 is attached in the vertical direction Z along the longitudinal groove 51g. In this process, the core 70 is attached to the male mold 51 while the positioning portion 79 is fitted over the area 519 corresponding to the cylindrical outer circumferential surface 39 (FIG. 34B).

Thus, since the blade portion 71A of the core 70 is fitted into the longitudinal groove 51g and also the positioning portion 79 is fitted over the area 519, the core 70 and the male mold 51 are unlikely to be positionally shifted. Therefore, the area formed by the filler 53 is unlikely to be positionally shifted with respect to the male mold 51.

Note that the blade portion 71A of the core 70 of the present embodiment extends in the vertical direction Z and goes into the deepest portion of the engaged groove 3e of the abutment 3, forming the entire portion of the slit 13s (FIG. 36A).

In the present embodiment, after the nylon resin is cured in FIG. 35C, the male mold 51 and the filler 53 are crushed, and moreover the core 70 is pulled out of the denture base 10, thus producing the denture 1 shown in FIGS. 36A and 36B. Therefore, there is no need to produce, by processing, the slits 13s after the molding process.

As shown in FIG. 36A, in this embodiment, three slits 13s are provided. The slits 13s extend in the radial direction of the abutment 3 so as to separate the engagement piece members 13 from one another in the circumferential direction. With respect to the abutment 3, the engagement piece member 13 extends in the circumferential direction of the abutment 3 as shown in FIG. 36A along the side surface of the abutment 3 of FIG. 36C over a range of the center angle θ less than 180°.

Since the number of engagement piece members 13 is typically preferably two to four, the center angle θ is preferably greater than 60° and less than 180°.

While the engagement piece members 13 are deformed to flare out, as if by pivoting about the end portion 13a of FIG. 36B, when attaching/detaching the denture 1, if the center angle θ is greater than 180°, the flexural rigidity will be high and they will not easily be deformed.

On the other hand, if the center angle θ is less than 60°, the force of holding the abutment 3 by the engagement piece member 13 will likely be insufficient.

In the present embodiment, the abutment 3 of FIG. 36C does not always need to be provided with the longitudinal groove 3g and/or the positioning portion 79, and the replica 3R of the abutment 3 of FIG. 34B may be provided with the longitudinal groove 3g and/or the positioning portion 79. For example, without providing the abutment 3 with the longitudinal groove 3g and the positioning portion 79, the dentist attaches, by screwing, the replica 3R having the longitudinal groove 3g and/or the positioning portion 79, instead of the abutment 3, to the fixture 2, and produces the female mold 50 of FIG. 34B with the replica 3R attached.

Figure 38A:
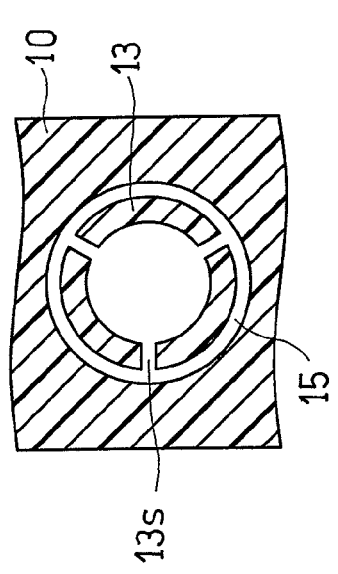
FIGS. 38A and 38B are a cross-sectional plan view and a longitudinal cross-sectional view, respectively, showing step 73.
Figure 38B:
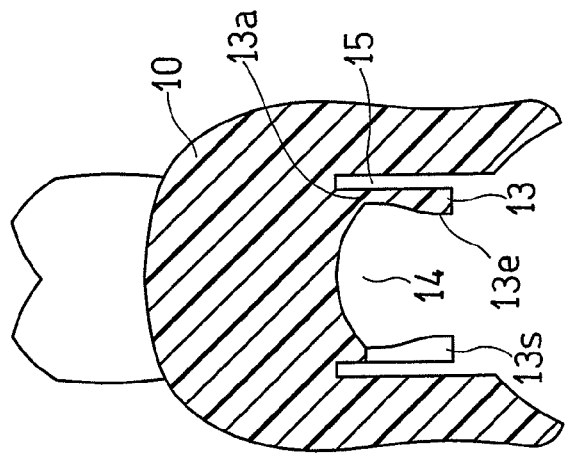
Figure 38C:
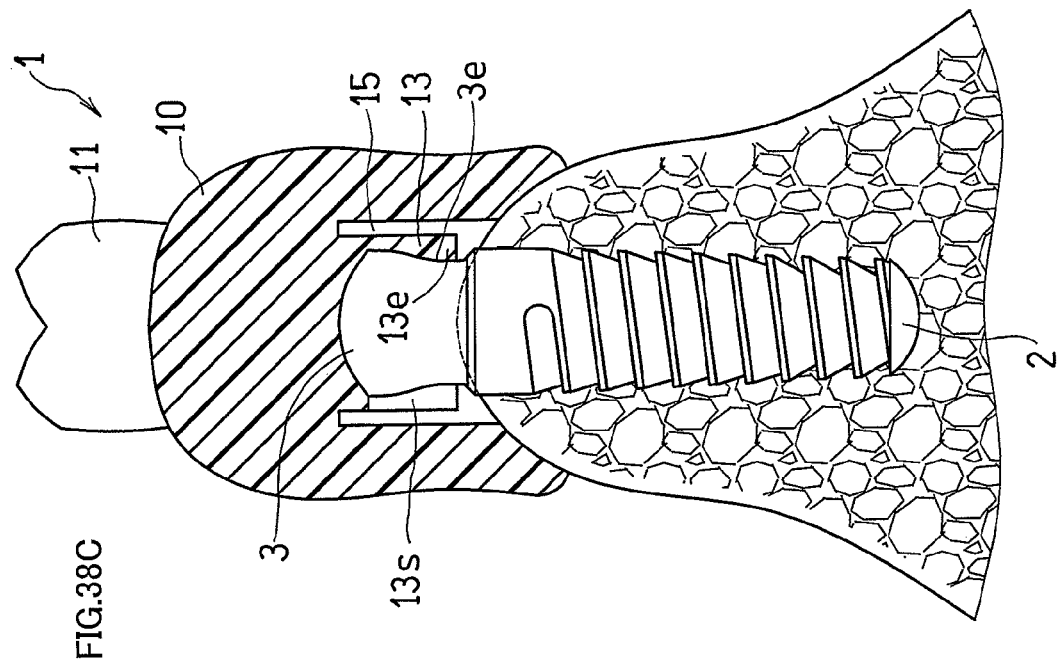
FIG. 38C is a longitudinal cross-sectional view showing step 74.

Thus, where the artificial tooth 11 is produced by using the replica 3R having the longitudinal groove 3g, the longitudinal groove 3g does not need to be formed on the abutment 3 as shown in FIG. 38C, and an existing abutment 3 having a hole on the top 3t, which engages with a tool, can be used.

On the other hand, where the abutment 3 having the longitudinal groove 3g is used, the longitudinal groove 3g of the abutment 3 serves as a groove to be engaged with a tool when screwing the abutment 3 into the fixture 2. Therefore, there is no need for the engaging hole of the existing abutment 3, resulting in a large surface area on the top 3t over which the abutment 3 is in contact with the denture base 10.

FIGS. 37A to 38C show still another embodiment. In this embodiment, the core 70 of FIG. 37A is divided in the radial direction into a plurality of pieces. The divided cores 70D can be brought closer in the radial direction toward and attached to the area 51b of the male mold 51 of FIG. 37B corresponding to the abutment.

Note that after the attachment, the divided cores 70D and 70D may be put together by a bond or an adhesive.

FIGS. 39A to 40D show a general-purpose embodiment. While the height of the core 70 may be lower than, or higher than, the abutment 3 in the embodiments of FIGS. 1A to 38C described above, the height of the cylinder to be the core 70 is set to be high in advance in the embodiment of FIG. 39A.

Figure 39A:
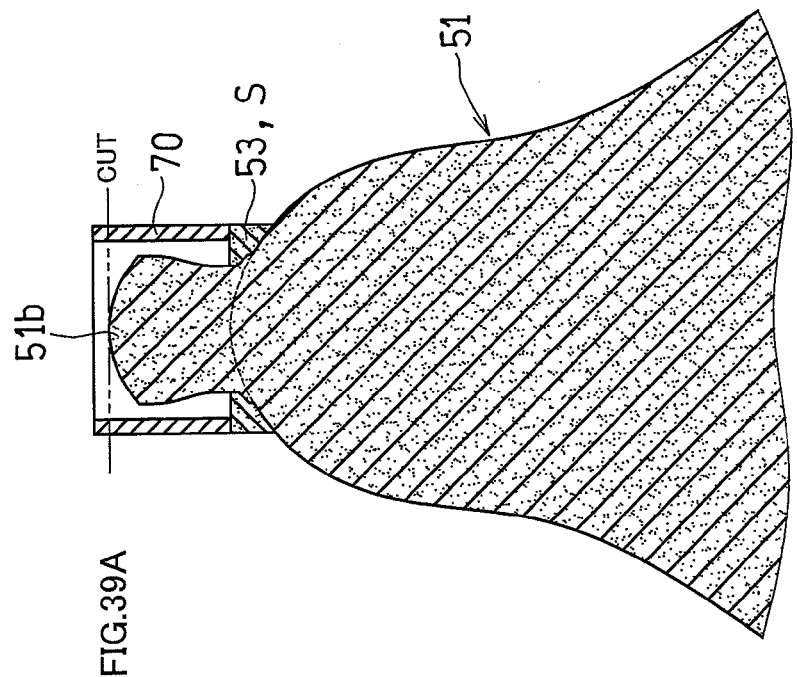
FIGS. 39A and 39B are cross-sectional views showing steps 81 and 82, respectively, of a method for producing a denture according to Embodiment 13.
Figure 39B:
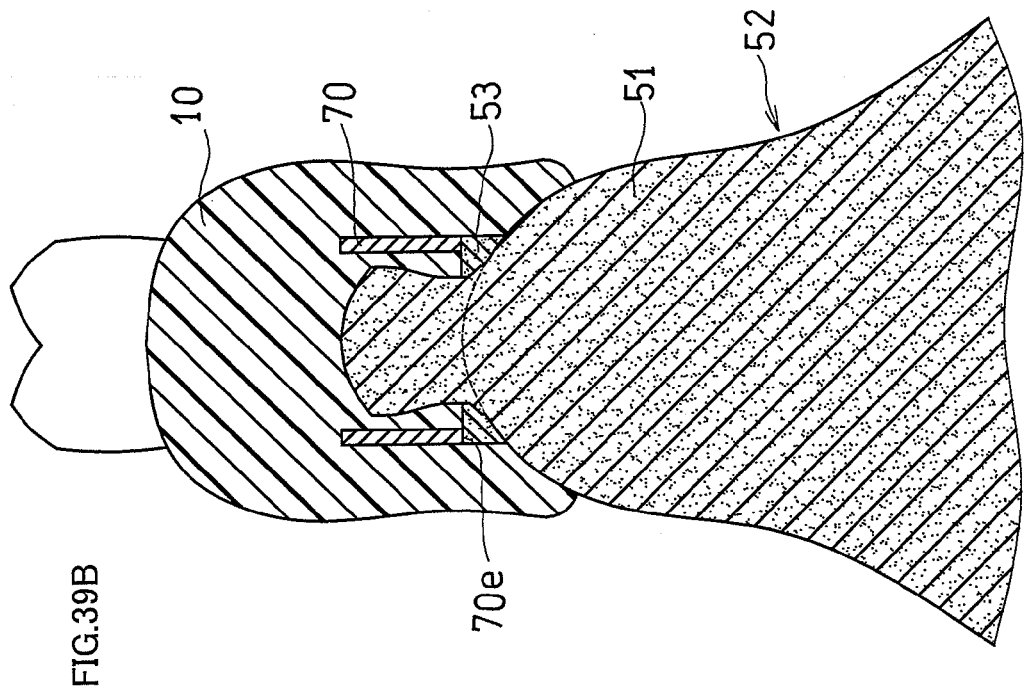
Figure 40A:
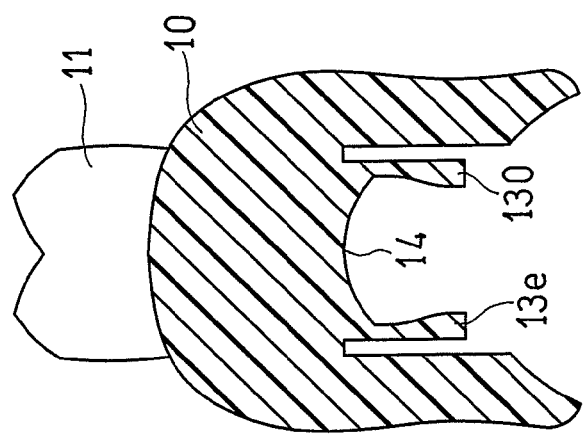
FIGS. 40A and 40B are a longitudinal cross-sectional view and a cross-sectional plan view, respectively, showing step 83.
Figure 40B:
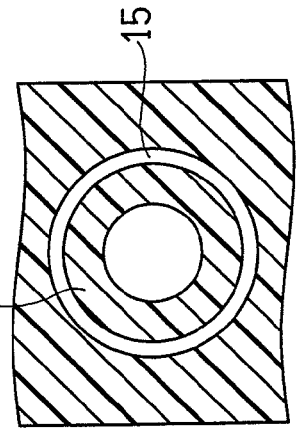
Figure 40C:
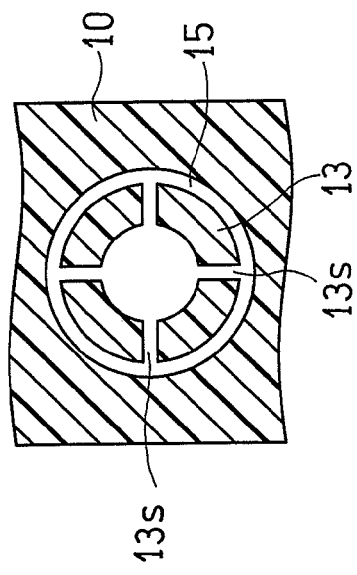
FIGS. 40C and 40D are a cross-sectional plan view and a longitudinal cross-sectional view showing step 84.
Figure 40D:
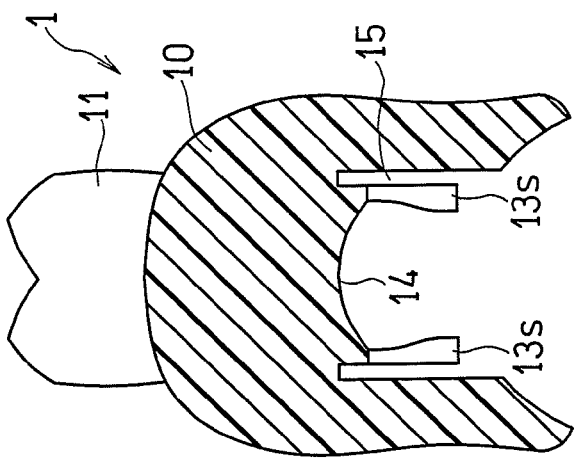

In FIG. 39A, the core 70 is cut off along a phantom line denoted by a two-dot-chain line so as to remove an upper portion thereof in advance. The core 70 of the present embodiment has no blade portion 71A, and therefore the slits 13s of FIGS. 40C and 40D are formed by processing after the molding process in a cylindrical area 130 of FIGS. 40A and 40B.

FIGS. 41A to 41D show still another embodiment.

In this example, a plurality of projections 3p are formed integrally on the side surface of the abutment 3 or the replica 3R thereof. The projections 3p extend from the top 3t toward the male screw portion 3s (FIG. 34B), and have a greater height than the depth of the engaged groove 3e, and a number of projections 3p equal to the number of the slits 13s (FIG. 40C) are provided while being spaced apart from one another in the circumferential direction.

In this example, the male mold 51 of FIGS. 41C and 41D is produced by removing the female mold 50 as shown in FIG. 41B. Projections 51p corresponding to the projections 3p are formed integrally on the male mold 51. The cylindrical core 70 is attached to the male mold 51, and then the denture 1 is produced through steps 63 to 65 of FIGS. 35B to 36B.

In this example, the core 70 needs no blade portion 71A.

FIGS. 42A and 42B show still another example.

In this example, the positioning portion 79 is formed integrally on the lower end portion of the core 70. The positioning portion 79 is in contact with, or close to, the circumference of the area 51b of the male mold 51 corresponding to the abutment so as to position the core 70 in the radial direction. The positioning portion 79 will also facilitate the filling with the filler 53.

FIGS. 43 to 46C show a fabrication method in a case where there is one engagement piece member 13.

Figure 43:
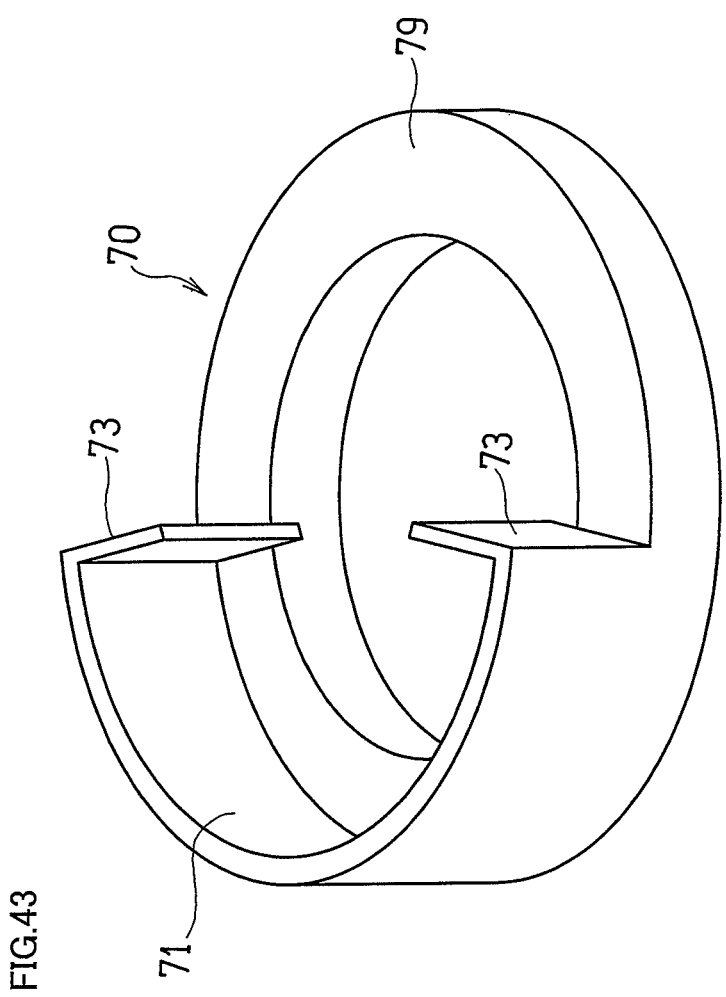
FIG. 43 is a perspective view of a core used in producing a denture according to Embodiment 16.
Figure 44A:
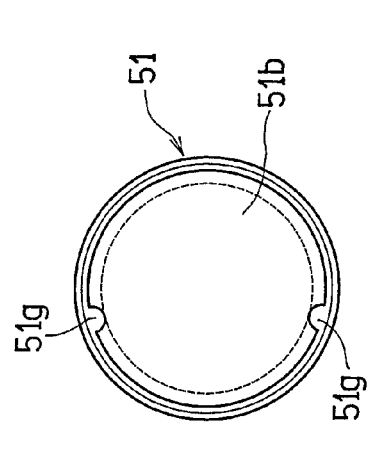
FIGS. 44A and 44B are a cross-sectional plan view and a longitudinal cross-sectional view, respectively, showing step 111 of a method for producing a denture according to Embodiment 16.
Figure 44C:
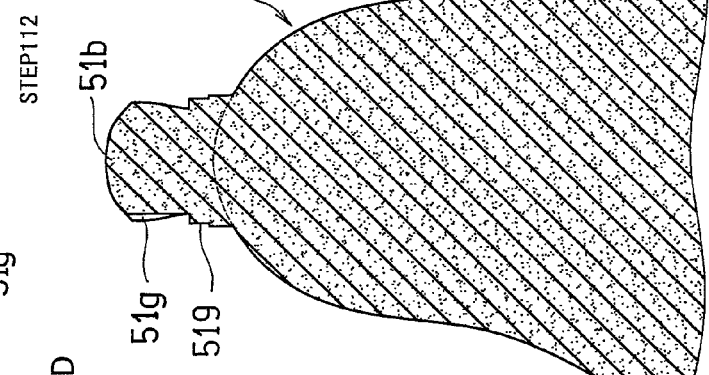
FIGS. 44C and 44D are a plan view and a longitudinal cross-sectional view, respectively, showing step 112.
Figure 44B:
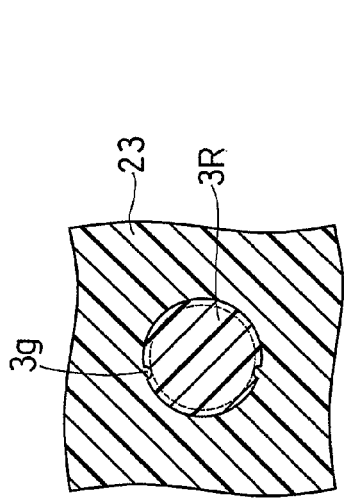
Figure 44D:
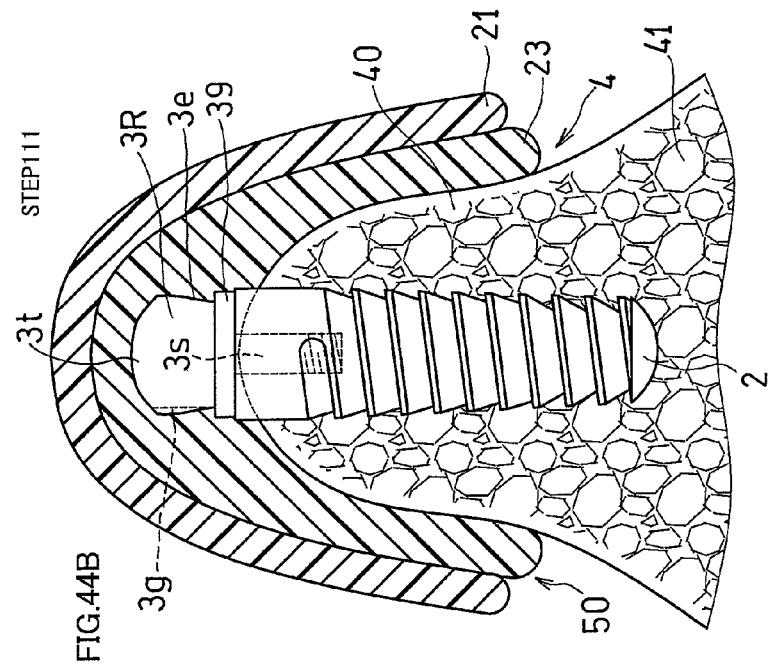

In FIG. 43, the core 70 includes the positioning portion 79, the first part 71 having a curved plate shape, and a pair of blades 73. The ring-shaped positioning portion 79 has the function of holding the core 70 attached to the male mold 51 as shown in FIG. 45A.

In the present embodiment, a denture is produced as will be described below by using the replica 3R of an abutment having a pair of longitudinal grooves 3g corresponding to a pair of blades 73.

Figure 46A:
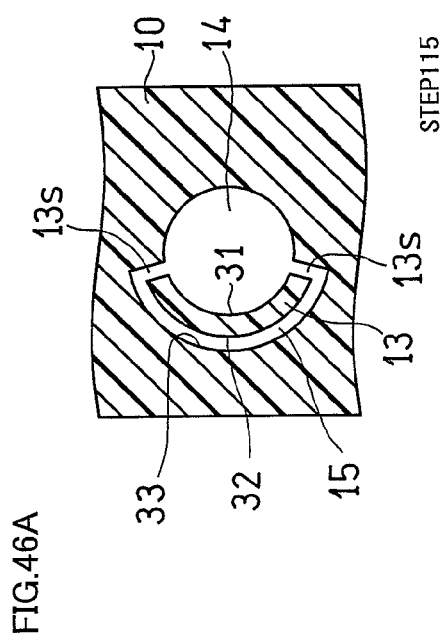
FIGS. 46A and 46B are a cross-sectional plan view and a longitudinal cross-sectional view, respectively showing step 115.
Figure 46B:
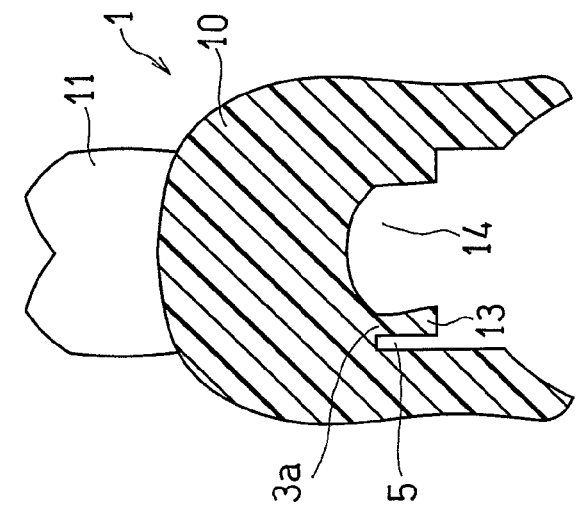
Figure 46C:
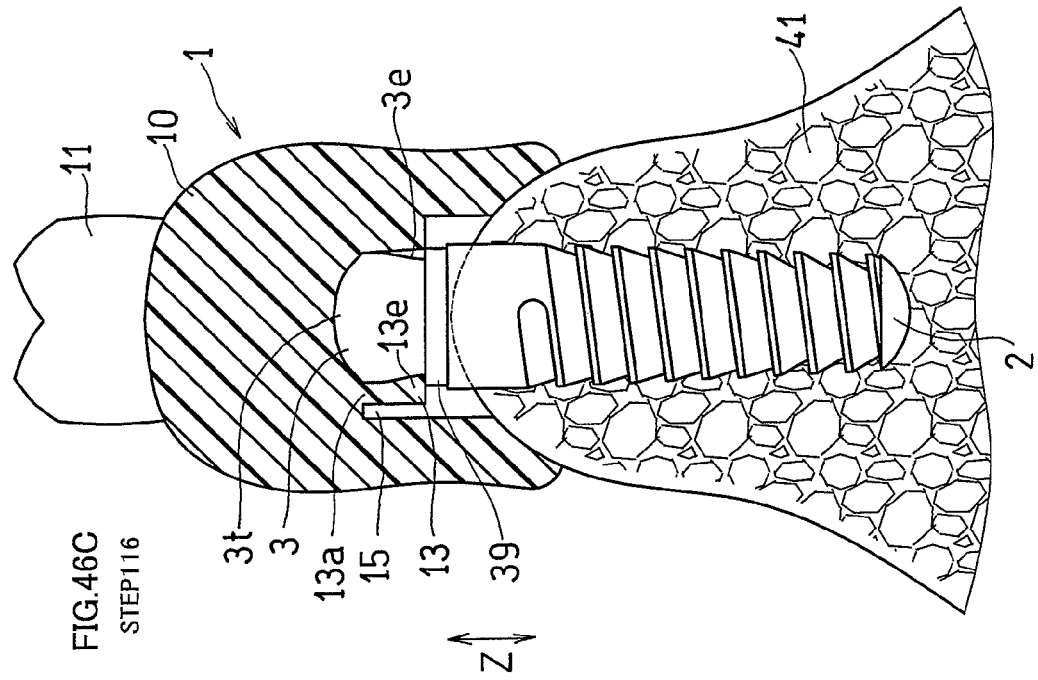
FIG. 46C is a longitudinal cross-sectional view showing step 116.

In the present embodiment, steps 111 to 116 of FIGS. 44A to 46C are performed as are steps 61 to 66 of FIGS. 34A to 35C of the embodiment described above, thereby molding the denture base 10 of FIG. 46C.

Now, in the present embodiment, an area of the male mold 51 corresponding to the engaged groove 3e of the abutment is filled with a ceramic filler 300 such as a plaster as shown in FIG. 45A. This makes it possible to attach/detach the denture base 10 to the abutment 3 in such a manner that the denture base 10 of FIG. 46C does not engage with the engaged groove 3e.

Figure 47:
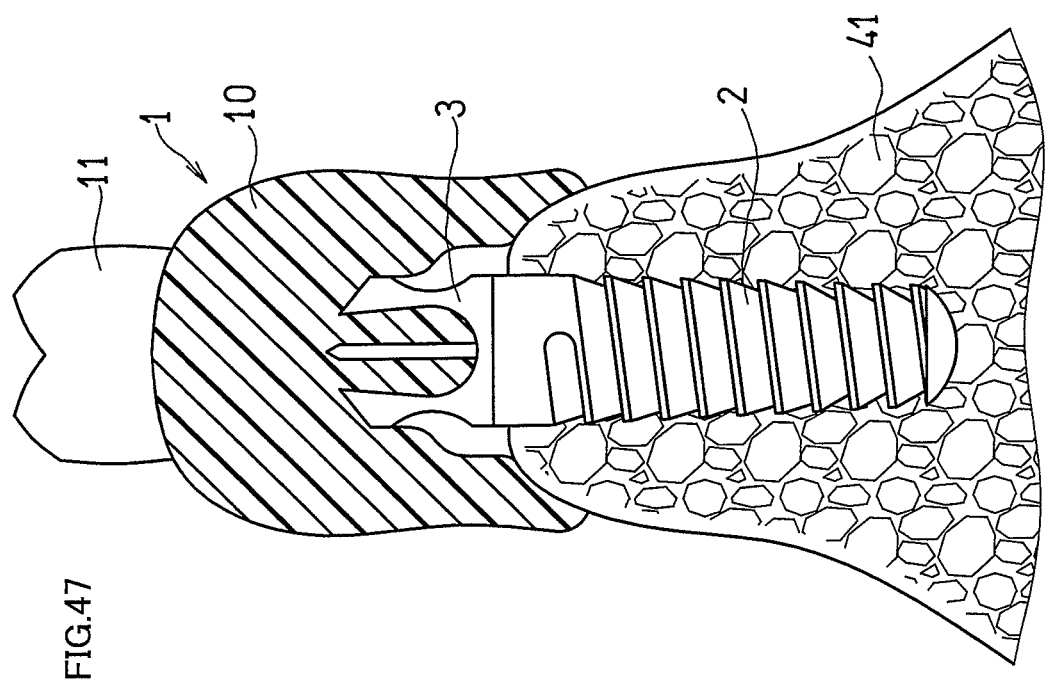
FIG. 47 is a cross-sectional view showing a denture according to a reference embodiment as an aid to understanding the present invention.

In a reference embodiment of FIG. 47, a plurality of (preferably, three or four) engagement piece members 13 formed integrally with the denture base 10 are fitted into an engaged depressed portion 3c formed inside the abutment 3. As compared with the reference embodiment, the present invention is advantageous in that a stable fit is likely to be obtained since the engagement piece members 13 engage with the outer circumferential surface of the abutment 3.

FIGS. 48A to 57B show another Embodiment.

Figure 48A:
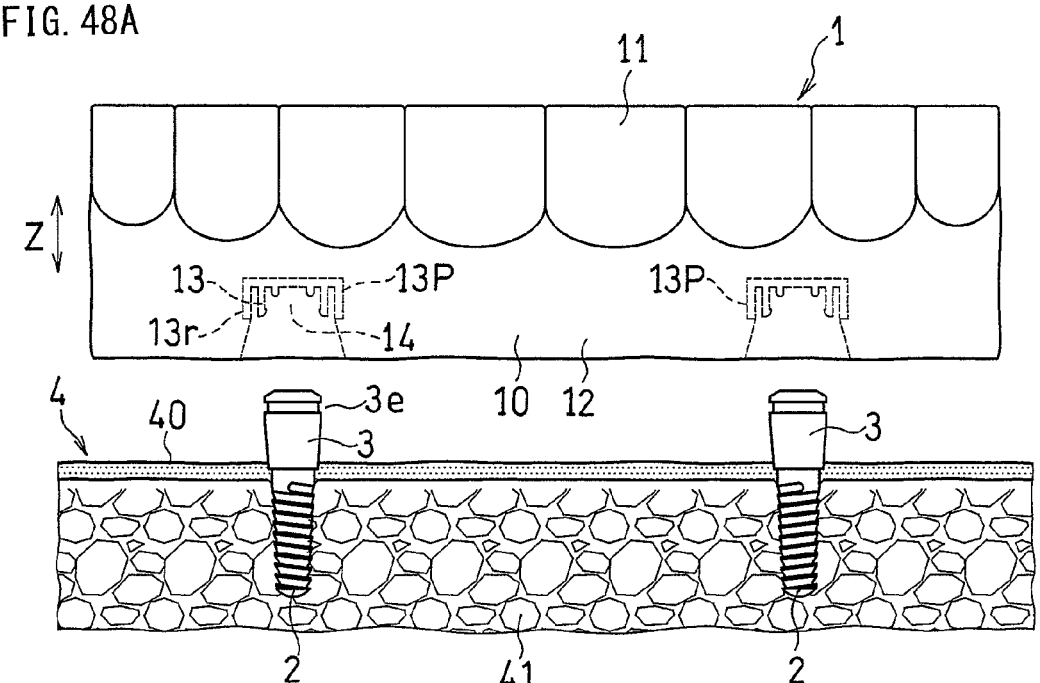
FIG. 48A is a front view showing one embodiment of the present system with the denture removed from the oral cavity.
Figure 48B:
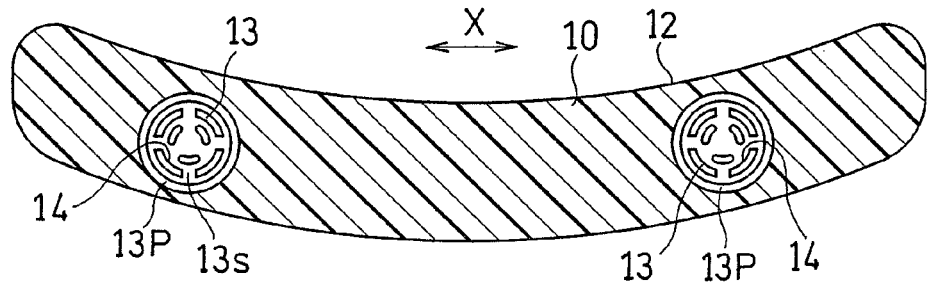
FIG. 48B is a cross-sectional plan view of the denture base.
Figure 48C:
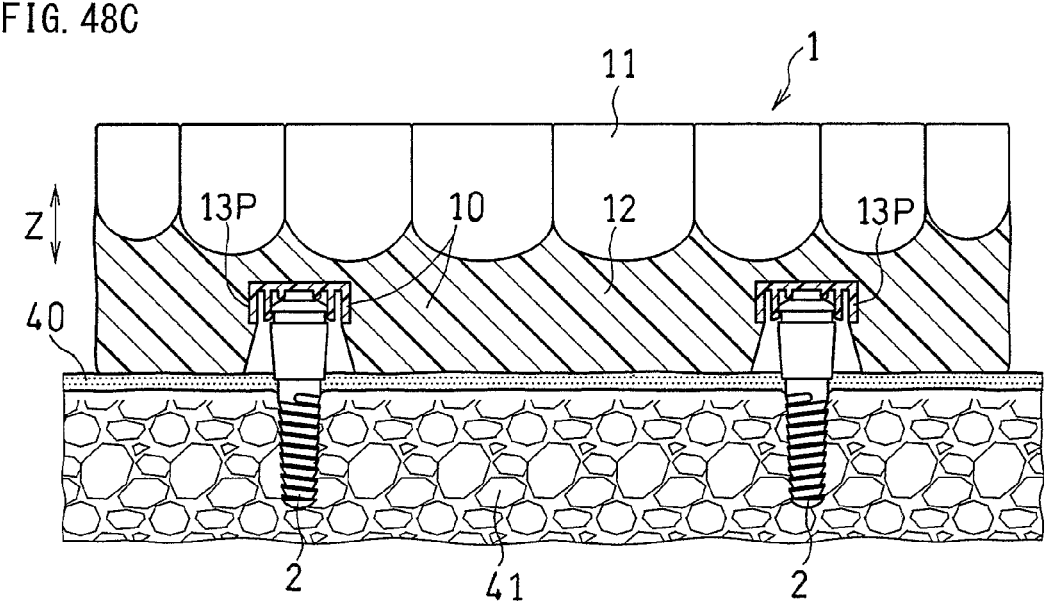
FIG. 48C is a plan view showing the one embodiment with the denture placed in the oral cavity.

As shown in FIGS. 48A and 48C, the present denture system includes the denture 1, the fixture 2, and the columnar abutment 3.

Figure 50:
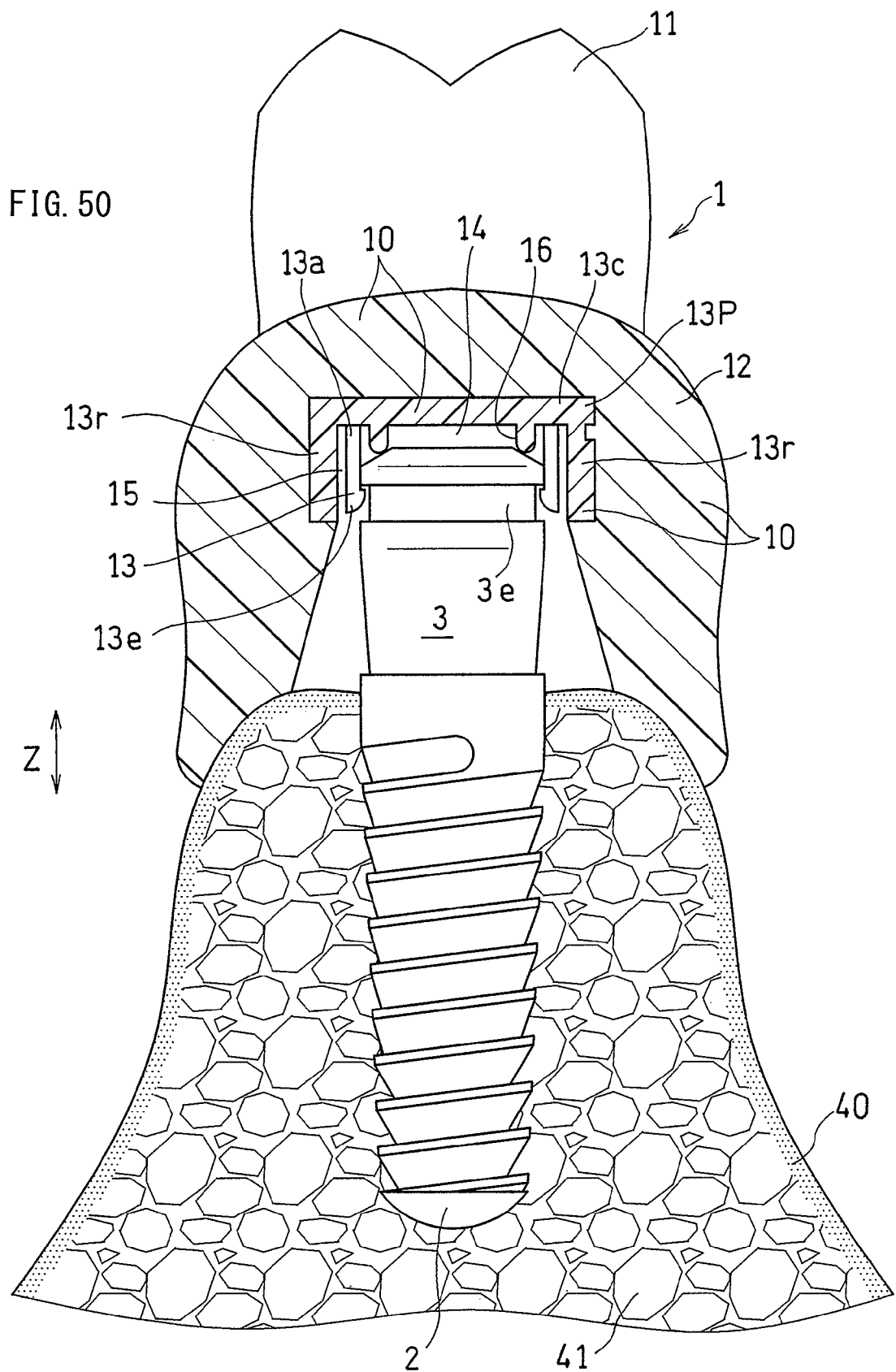
FIG. 50 is a cross-sectional view showing a state in which a denture of the embodiment is worn.

As shown in FIG. 50, the fixture 2 is a so-called "implant body", an artificial tooth root obtained by performing a surface process (surface finishing) on a biomaterial (a typical material being titanium, which is well compatible with a living body). The fixture 2 is buried in the oral tissue 4 such as an alveolar bone 41 of the jaw to be integrated with the bone.

The abutment 3 is coupled to the fixture 2 and exposed in the oral cavity. That is, the abutment 3 is fixed to the fixture 2 of FIG. 50 with a screw of FIG. 51C and is coupled to the fixture 2 so that the artificial denture 1 can be attached thereto.

As shown in FIGS. 48A and 48C, the denture 1 is detachably attached to the abutment 3. The denture 1 includes the nylon-made denture base 10 to be in contact with the gum 40, and ceramic artificial teeth 11 integral with the denture base 10 and supported by the denture base 10.

For example, a pair of the fixtures 2 and the abutments 3 is provided in the oral cavity and the present system is applied to the pair of the fixtures 2 and the abutments 3.

The artificial teeth 11 are secured to one end of the denture base 10 in the vertical direction Z. The other end surface of the denture base 10 in the vertical direction Z is softly in contact with the gum 40.

As shown in the enlarged cross-sectional view of FIG. 50, the denture base 10 includes a main body 12 and the engagement piece members 13 integrally continuous with each other, and defines the fitting holes 14 into which columnar abutments 3 are detachably fitted. The engagement piece members 13 and the denture base 10 are formed by a nylon-based thermoplastic resin, for example.

The fitting holes 14 are open toward the gum 40. That is, the fitting holes 14 of an upper denture 1 are open in the upward direction, and the fitting holes 14 of a lower denture 1 are open in the downward direction.

As shown in FIG. 50, the engagement piece members 13 form the fitting hole 14. That is, as clearly shown in FIG. 51B, the fitting hole 14 is defined by a plurality of the engagement piece members 13. The fitting hole 14 positions and fixes the denture base 10 with respect to the abutment 3. The engagement piece member 13 has a first surface 31 to be in contact with and engaging with the side surface of the abutment 3, and a second surface 32 opposite to the first surface 31.

In the present embodiment, where the denture 1 is placed in the lower jaw, the upper end portion 13a of the engagement piece member 13 of FIG. 50 is continuous with the denture base 10, and the engagement piece member 13 extends downwardly in the vertical direction Z from the end portion 13a of the engagement piece member 13.

Note that although not shown, in a case where the denture 1 is placed in the upper jaw, the lower end portion of the engagement piece member 13 is continuous with the main body 12, and the engagement piece member 13 extends upwardly in the vertical direction Z from the end portion of the engagement piece member 13.

In the present embodiment, an engagement element (engagement protrusion) 13e to be engaged with the narrowed engaged groove (engaged element) 3e of the abutment 3 is formed integrally with the engagement piece member 13 at the lower end of the engagement piece member 13. As the engagement element 13e is engaged with the engaged groove 3e, the denture 1 is prevented from inadvertently coming off the abutment 3.

Figure 51A:
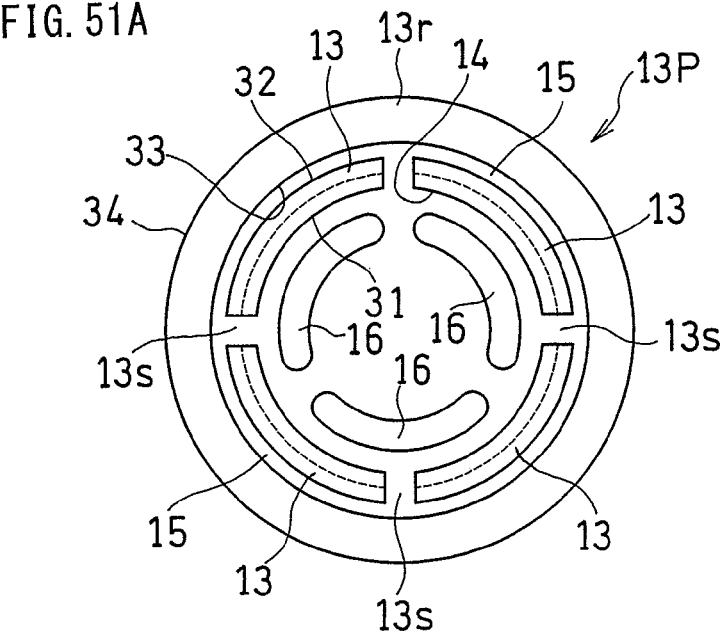
FIG. 51A is a plan view of an engagement piece.
Figure 51B:
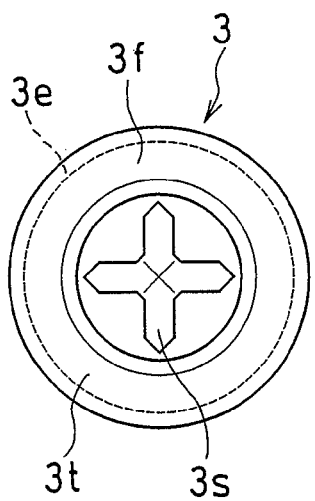
FIG. 51B is a plan view of an abutment.
Figure 51C:
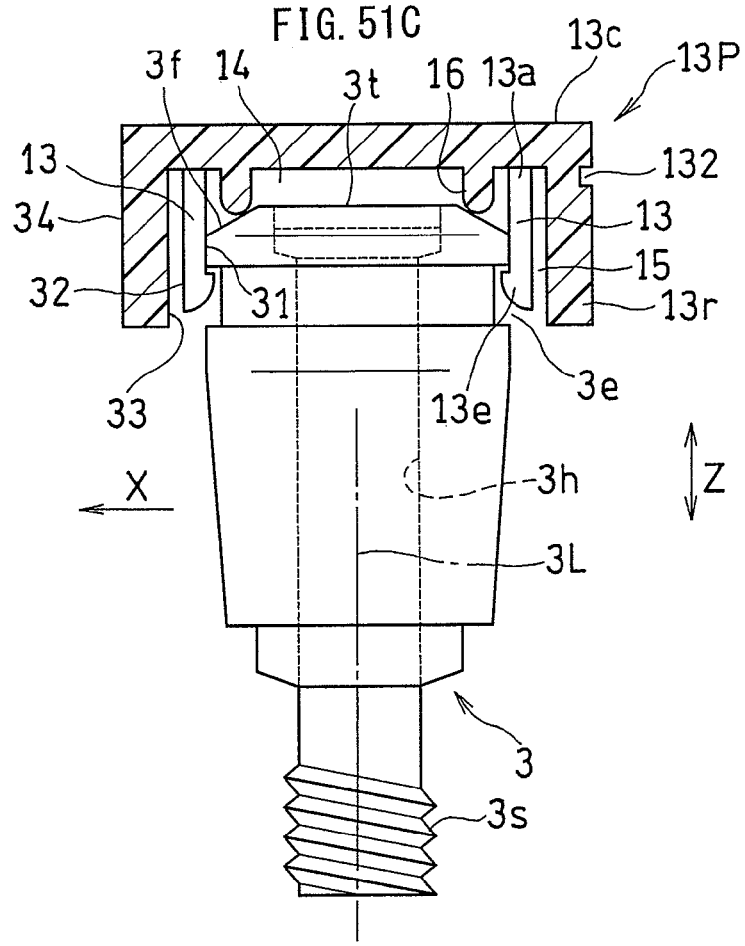
FIG. 51C is a partially sectioned front view showing the engagement piece and the abutment.

The denture base 10 of FIG. 51C includes the allowance portion 15 formed between the second surface 32 and the third surface 33, wherein the allowance portion 15 allows the engagement piece member 13 to move or deform in the horizontal direction X from the first surface 31 toward the second surface 32. The allowance portion 15 is provided as a groove 15 formed in the denture base 10. The third surface 33 is spaced apart from, and opposing, the second surface 32.

The groove 15 of FIG. 51A is continuous with the fitting hole 14 via the slit 13s, thereby facilitating the movement of the engagement piece member 13. When placing/removing the denture 1, the engagement piece member 13 retracts toward the groove 15, thereby allowing the denture 1 to be attached/detached to/from the abutment 3.

The denture base 10 may include a cushion portion 16 formed at the deep end in the vertical direction Z of the fitting hole 14 of FIG. 50. The cushion portion 16 is formed by a plurality of small projections or ridges, and the projections or the ridges will provide the denture 1 with cushioning in place of the natural periodontal membrane by elastically deforming when clenching the teeth.

The denture base 10 made of a nylon-based resin will unlikely deteriorate and will unlikely whiten over years of use. Moreover, the denture base 10 of such a material will unlikely lose the elasticity of the engagement piece member 13. Particularly, when the engagement piece member 13 deteriorates due to permanent deformation, lowering of elasticity, etc., it will be possible to restore the engagement piece member 13 while heating, with a hot air, the engagement piece member 13 and the denture base 10 around the fitting hole 14.

In this case, the engagement piece members 13 of FIG. 51A are provided in a state in which the engagement piece member 13 is divided into four parts. The four divided engagement piece members 13 are almost cylindrical shape as a whole and extend from the denture base 10 in the up-down direction Z.

Note: the engagement element 13e may be formed by a small protrusion integral with the first surface 31.

The abutment 3 of FIG. 51C defines, between the top 3t and the male screw portion 3s, a narrowed circumferential engaged groove 3e with which the engagement piece members 13 engage. The abutment 3 comprises the male screw portion 3s to be screwed into the fixture 2 (FIG. 48) and the through hole 3h into which the male screw portion 3s.

Figure 49:
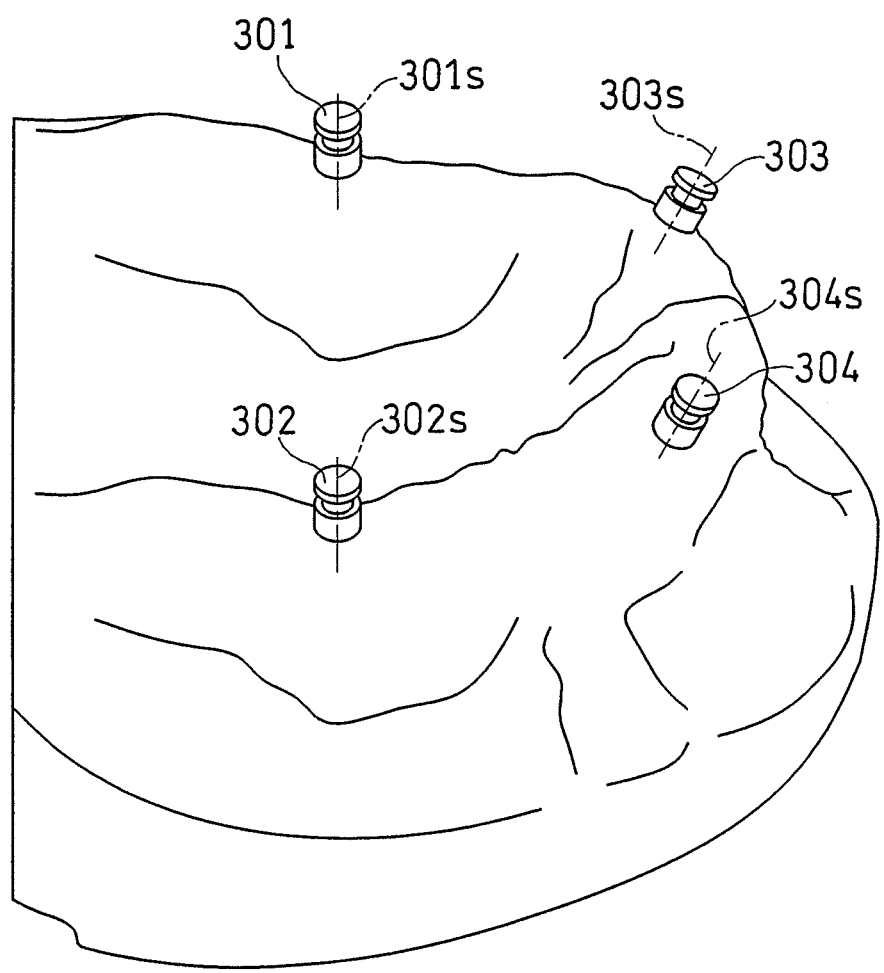
FIG. 49 is a perspective view showing the lower jaw model without teeth in which four abutments are attached.

FIG. 49 is a perspective view of a model showing an arrangement of the abutments 3 with respect to the oral cavity.

In this figure, a pair of abutments 301 and 302 arranged on the back side has their axial lines 301s and 302s parallel to each other. A pair of abutments 303 and 304 arranged on the front side has their axial lines 303s and 304s parallel to each other. However, the axial lines 301s and 302s of the abutments 301 and 302 and the axial lines 303s and 304s of the abutments 303 and 304 are not parallel to each other but are arranged in a skew relationship with respect to each other.

In such a case, the engagement piece members 13 of the present denture system elastically deform, thereby enabling the realization of the denture 1 which fits to the four abutments 301 to 304. In this case, the denture 1 of FIG. 48 having a plurality of engagement piece members 13 has high applicability.

The engagement element 13e of the engagement piece member 13 rubs against the abutment 3 every time the denture 1 of FIG. 50 is attached or detached. Therefore, it is preferred that the engaged groove 3e is formed in a smooth shape.

Next, the nylon-based engagement piece 13P of FIG. 51A and FIG. 51C that is principal part of the present invention will be described in detail.

The engagement piece 13P is integrally formed by a lid portion 13c, engagement piece portions 13, an outer portion 13r, and cushion portions 16, and defines an allowance portion 15.

The number of the engagement piece members 13 is three or four, for example. The engagement piece members 13 extend from the lid portion 13c in an up-down direction Z. The engagement piece members 13 elastically deform to spread around an end portion 13a in the up-down direction Z when attaching and detaching the denture 1, and engage with the abutment 3 when worn. The engagement piece members 13 are spaced apart from one another via slits 13s in a circumferential direction.

The outer portion 13r is a cylindrical shape, for example. The outer portion 13r has a third surface 33 extending in the up-down direction Z from a circumference of the lid portion 13c and being further from an axis 3L of the abutment 3 than the second surfaces 32 of the engagement piece members 13. As shown in FIG. 50, the outer portion 13r is joined to the body part 12 of the denture base 10 after molding the denture base 10. The outer portion 13r sandwiches a tubular member between the outer portion 13r and the engagement piece member 13, thereby securing the allowance portion 15 between the second surface 32 and the third surface 33.

The allowance portion 15 of FIG. 51C allows the engagement piece members 13 to be elastically deformed to spread in a direction from the first surface 31 toward the second surface 32. The allowance portion 15 is defined between the second surface 32 and the third surface 33 of the outer portion 13r.

Note: an engagement concave 132 or a small through hole that is used for ensuring the engagement between the outer portion 13r and the body portion 12 may be provided on the fourth surface 34 of the outer portion 13r.

The lid portion 13c covers an entire surface of the top 3t of the abutment 3 and is covered by the body part 12 (FIG. 50) of the denture base 10. The lid portion 13c closes one end, in the up-down direction Z, of the fitting hole 14 defined by the engagement piece members 13 and closes one end, in the up-down direction Z, of the allowance portion 15.

As shown in FIG. 50, the lid portion 13c and the outer portion 13r are integrated with the body portion 12, forming a part of the denture base 10.

The cushion portion 16 of FIG. 51C projects toward the abutment 3 at an area of the lid portion 13c corresponding to the outer circumferential edge of the top 3t of the abutment 3 and inside the engagement piece members 13. The cushion portion 16 may be formed by a plurality of arc-shaped cushion portions 16 of FIG. 51A or a circular shape cushion portion 16.

That is, the cushion portion 16 projects toward the abutment 3 of FIG. 51C inside the engagement piece members 13 and contacts with the outer circumferential edge of the top 3t outside the through hole 3h.

The outer circumferential edge of the top 3t has a conic tapered surface 3f in which the edge is closer to the fixture 2 (FIG. 48) as the edge is closer to the outer end of the top 3t. The cushion portion 16 contacts with the abutment 3 on the tapered surface 3f.

The engaged groove 3e is formed so as to be longer than the engagement element 13e in the direction of the axis 3L. Thereby, the engagement piece 13P slightly moves up and down with respect to the abutment 3 in accordance with the deformation of the cushion portion 16 when clenching teeth.

A ratio of pigment to resin forming the engagement piece 13P is set to be from 0 weight percent to 0.07 weight percent. Therefore, a ratio of the pigment contained in the resin forming the engagement piece 13P is smaller than a ratio of pigment contained in resin forming the body part 12 of the denture base 10 (0.1 weight percent to 0.20 weight percent).

Next, a method for producing the denture 1 (FIG. 50) will be described.

FIG. 52A to 57B shows an example of the method.

First, as shown in FIG. 52A, a dentist produces, according to a well-known method, a female mold 50 of the oral cavity by using a tray 21A and a soft impression material 23 (silicon resin (including silicon rubber)). The fixture 2 is buried in the mold 50 and the abutment 3 is connected with the fixture 2. After the impression material 23 is solidified, the tray 21A and the impression material 23 are removed from the oral cavity, thereby obtaining the female mold 50. The subsequent steps are performed by a dental technician rather than a dentist.

As shown in FIG. 52B, a replica 3R of the abutment 3 (not abutment 3 itself) is installed to the female mold 50.

Figure 53B:
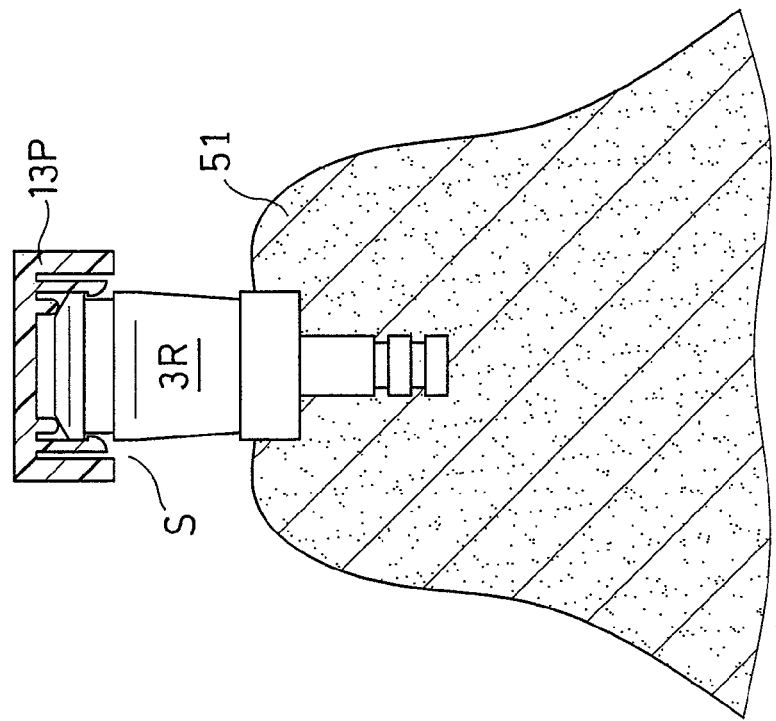
FIG. 53A and FIG. 53B are cross sectional views each showing a process for producing a denture.
Figure 53A:
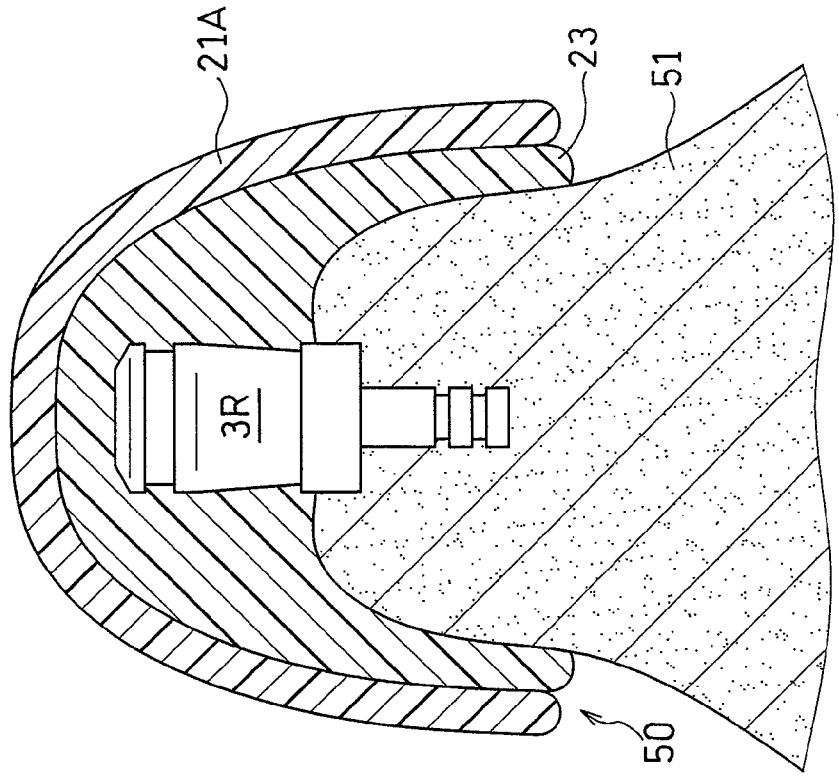

As shown FIG. 53A, the dental technician pours a plaster 51a into the concave portion of the impression material 23 in order to make a male mold 51 of the impression material 23. Thus, the male mold 51, having the replica 3R of the abutment 2 projected therefrom and having the shape of the oral cavity, is produced from the female mold 50. Then, as shown in FIG. 53B, the engagement piece 13P made by a nylon is fitted to the replica 3R of the male mold 51. The engagement piece 13P contains no pigment.

Figure 54A:
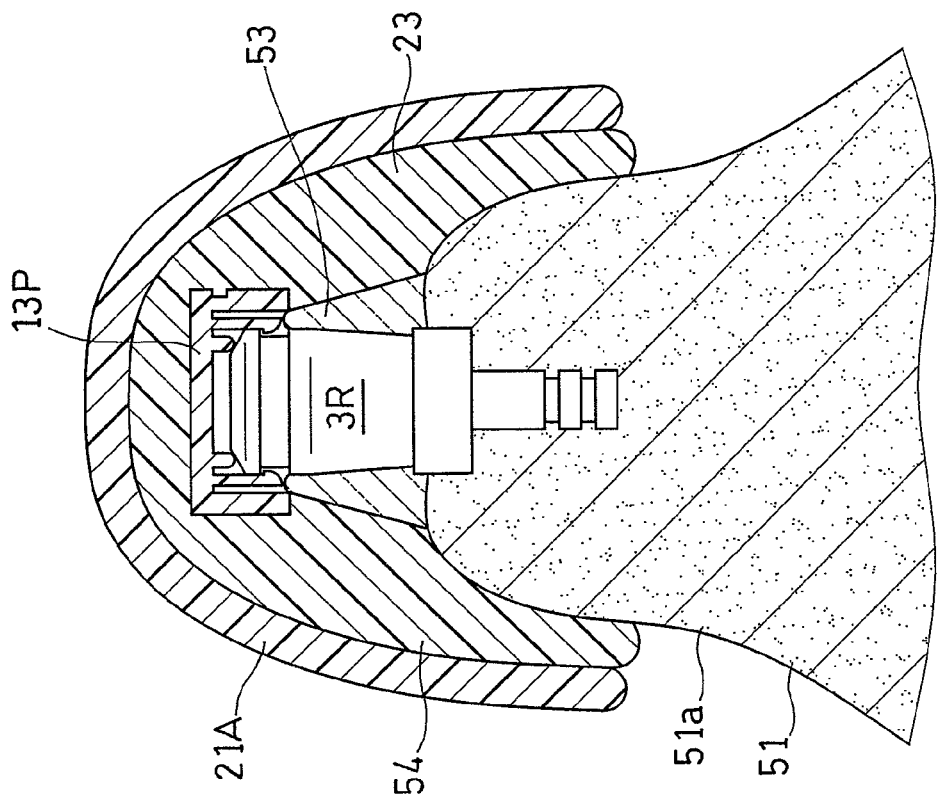
FIG. 54A and FIG. 54B are cross sectional views each showing a process for producing a denture.

Now, although a gap S to be an undercut in the molded product is formed between the lower end of the engagement piece 13P and the surface of the male mold 51, as shown in FIG. 54A, the shape of the male mold 51 is corrected by filling the gap S with the filler 53. Note that a wax may be employed as the filler 53, for example.

Figure 54B:
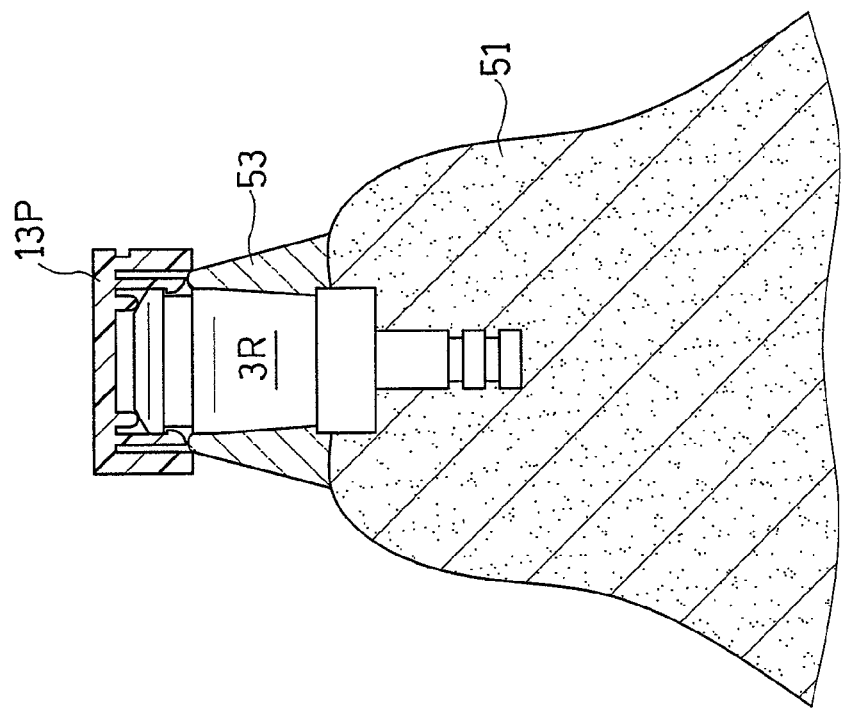

Then, as shown in FIG. 54B, the replica 3R, the filler 53 and the plaster 51a are removed from the female resin form 54 after wrapping the male mold 51 with a self-hardening resin (impression material like silicon resin). Thus, as shown in FIG. 55A, the female resin mold 54 that the engagement piece 13P is buried in is produced. The mold 54 has the depressed portion 500 corresponding to the shape of the oral cavity 4.

Thereafter, the restraint member R formed of a metallic pipe is inserted into the allowance portion 15 of the engagement piece 13P of the female resin mold 54 shown in FIG. 55B. The restraint member R is inserted into the allowance portion 15 and works as a core when molding the body part 12 of the denture base 10. Therefore, the outer portion 13r is prevented from deforming (moving) toward the engagement piece members 13 when molding the body part 12 of the denture base 10.

Figure 56B:
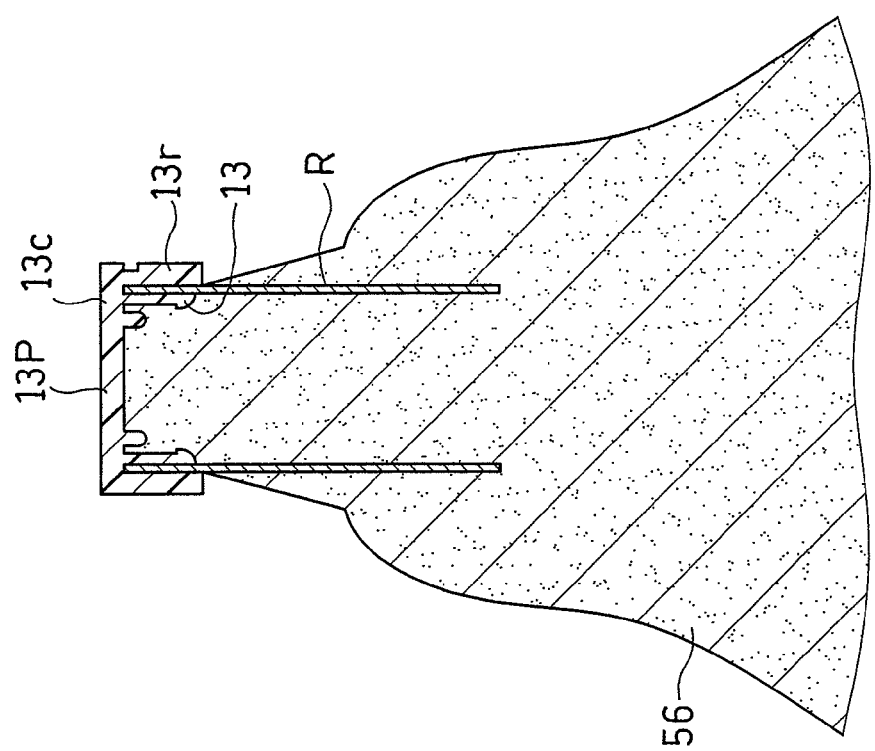
FIG. 56A and FIG. 56B are cross sectional views each showing a process for producing a denture.
Figure 56A:
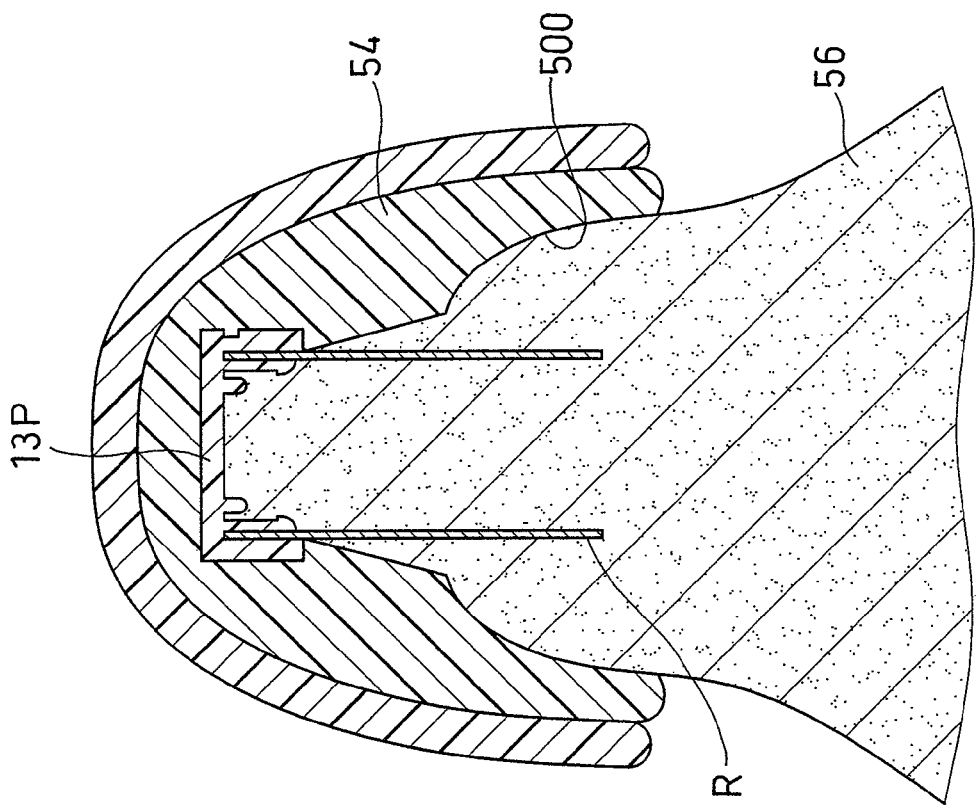

After the insertion of the restraint member R, as shown in FIG. 56A, plaster is poured into the depressed portion 500 of the female resin mold 54. Thereby, the male plaster mold 56 is produced. The restraint member R is buried in the plaster of the mold 56, and the engagement piece 13P is integral with the mold 56.

Figure 57B:
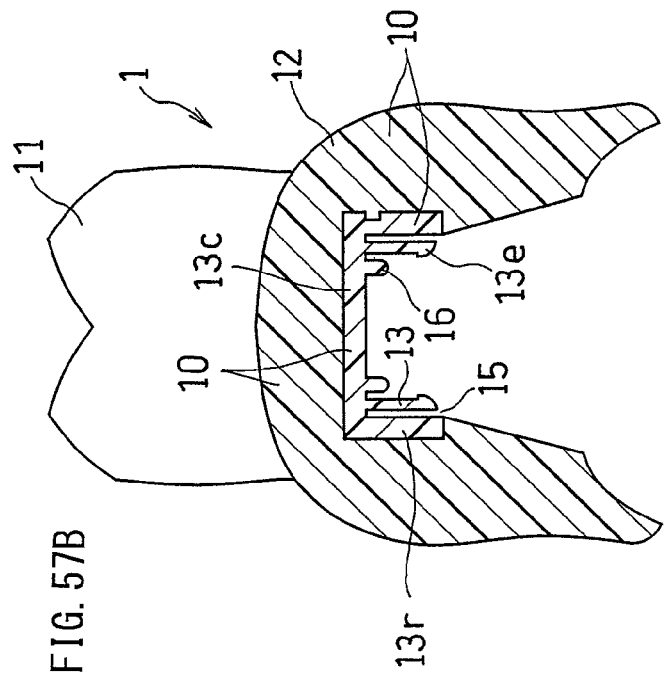
FIG. 57A and FIG. 57B are cross sectional views each showing a process for producing a denture.
Figure 57A:
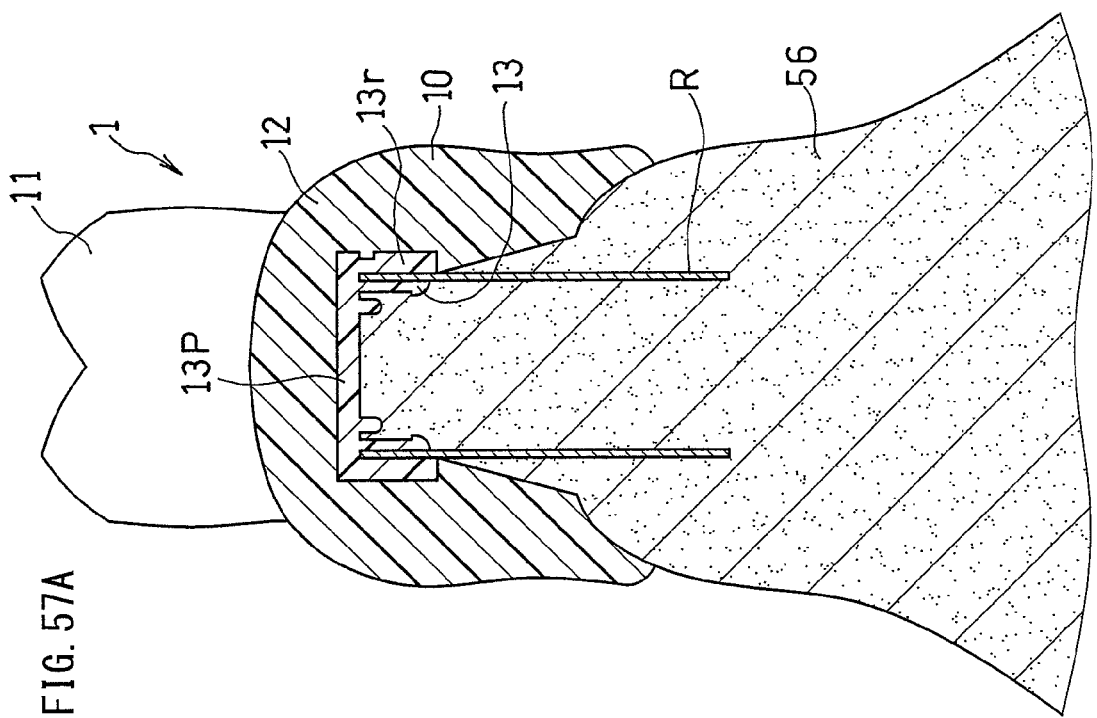

The molten resin made of nylon containing 0.10 to 0.20 weight percent of pigment is injected between the male plaster mold 56 and a well-known female mold of a denture 1 (not shown), thereby molding the body part 12 of the resin denture base 10 of FIG. 57A as well as producing the denture base 10 in which the body part 12 of the denture base 10 is integral with the engagement piece 13P. After the body part 12 is solidified, the plaster of the male plaster mold 56 and the restraint member R is removed.

Thus, the denture 1, shown in FIG. 57B, having the allowance portion 15 is produced.

Therefore, not only a dentist's and a patient's burden will be reduced, but also work of forming the allowance portion 15 by a dental technician will remarkably be simple and easy.

In this embodiment, the restraint member R may be a cup-like resin having a cylindrical portion to be inserted into the allowance 15 or may be a piece of rubber, instead of a metallic pipe.

FIG. 58A shows another embodiment.

As shown in FIG. 58A, in this embodiment, the body part 12 of the denture base 10 is formed by resin, such as polycarbonate, acryl resin, or polyester, different from the resin of the engagement piece 13P. A coupling layer 19 of a two-component autopolymerizing resin is interposed between the body part 12 of the denture base 10 and the engagement piece 13P, whereby the denture base 10 and the engagement piece 13P are coupled together and formed integral and continuous together.

In FIG. 58A, the engagement piece 13P is formed in a generally cylindrical shape with a bottom, i.e., a cup shape, having a plurality of (e.g., four) slits 13s and engagement piece members 13 inside the outer portion 13r, with a lid portion 13c. The lid portion 13c couples together the plurality of engagement piece members 13. Note that each engagement piece member 13 has an engagement element 13e.

The lid portion 13c covers the top portion (top) 3t of the abutment 3. The anchor grooves 13g and 10g are formed in the lid portion 13c and an area of the body portion 12 of the denture base 10 opposing the lid portion 13c. The space between the lid portion 13c and the body part 12 of the denture base 10 and the anchor grooves 13g and 10g are filled with the autopolymerizing resin of the coupling layer 19.

Note that the anchor grooves 13g of the body part 12 of the denture base 10 are formed in the inner surface of an accommodating depressed portion 10c.

A deep hole 10h to be the gate for pouring the resin is formed in the denture base 10, and the deep hole 10h is also filled with the resin. Note that the deep hole 10h connects the outer surface of the denture base 10 with the deep end of the accommodating depressed portion 10c.

The accommodating depressed portion 10c having a columnar shape for accommodating the engagement piece 13P therein is formed in the body part 12 of the denture base 10.

Note that, as shown in FIG. 51A, the slits 13s run through the engagement piece 13P in the radial direction from the first surface 31 to the second surface 32.

The method of this embodiment for producing a denture 1 is disclosed in the paragraphs 0087 to 0098 and FIG. 21A to FIG. 27C of WO 2012/132819A1, and the entire contents of these disclosures and descriptions are hereby incorporated herein.

FIG. 58B and FIG. 58C show another embodiment.

In FIG. 58B, the outer portion 13r of the present embodiment has the third surface 33 that is a part of the recessed cylindrical surface (not a complete cylindrical shape), and is divided into the plural. On the other hand, the engagement piece members 13 do not oppose to the outer portions 13r, and the engagement piece members 13 and the outer portions 13r are alternately placed in the circumferential direction. In this case, the restraint member R is still supported by being sandwiched between the outer portions 13r and the engagement piece member 13. Therefore, the allowance portion 15 (FIG. 50) is able to be formed toward which the engagement piece members 13 deform.

Note that the outer portions 13r may be formed by a plurality of pins (round bars) integral with the lid portion 13c. In this case, a surface of the pin forms the third surface 33.

FIG. 58D and FIG. 58E show still another embodiment.

In the embodiment of FIG. 58D, there are no the outer portions 13r. In this embodiment, the second surface 32 of the plurality of the engagement piece members 13 of FIG. 58E is formed so as to be slightly widened from the lid portion 13c toward the tip. On the other hand, the tip portion of the engagement piece member 13 is formed so as to be slightly tapered toward the tip. Therefore, when the cylindrical restraint member R is externally fitted to the outer circumference of the second surface 32 of the engagement piece members 13, the restraint member R is held around the engagement piece members 13 because of elasticity of resin of the engagement piece members 13.

In order to position the restraint member R in the direction of axis 3L, it is preferred that a flange 139 is provided with the lid portion 13c. The flange 139 protrudes more outward than the second surface 32 of the engagement piece members 13.

Note that in the embodiments of FIG. 58B to FIG. 58E, if release agent is applied over the outer surface of the metallic restraint member R, the restraint member R will easily be removed from the body part 12 of the denture base 10 when producing the denture 1.

Now, in the embodiments of FIG. 58B to FIG. 58E, the allowance portion 15 is not formed in the process of FIG. 54B because the impression material 23 contacts with the engagement piece members 13. Therefore, the denture 1 is produced in accordance with the following process.

In this case, after the process of FIG. 52A to FIG. 53B, a circular tube restraint member R is externally fitted over the engagement piece members 13. Therefore, the allowance portion 15 is secured.

That is, in these embodiments, after the process of FIG. 52A to FIG. 53B, a tubular member R1 is externally fitted to the outer circumference of the engagement piece members 13 of the engagement piece in FIG. 54A. The tubular member R1 is provided in order to form the allowance portion 15 that allows the engagement piece member 13 to elastically deform. Thereafter, after the similar process of FIG. 54A to FIG. 55B, a female resin mold 54 is produced. The mold 54 has a depressed portion 500 that the engagement piece 13P and the tubular member R1 are buried in and corresponds to the shape of the oral tissue 4.

Thereafter, as with the process of FIG. 56A and FIG. 56B, plaster is poured into the depressed portion 500 of the female resin mold 54, producing a male plaster mold 56 in which the tubular member R1 and the engagement piece 13P are integral with the plaster. Thereafter, as with the process of FIG. 57A, molten resin containing pigment is injected around the male plaster mold 56, producing the denture base 10 in which the engagement piece 13P is integral with the body portion 12 of the denture base 10. After the production, as with the process of FIG. 57B, the plaster of the male plaster model 56 and the tubular member R1 are removed, and the denture 1 is produced.

FIG. 59A to FIG. 61C show still another embodiments.

In the engagement piece 13P of these embodiments, the outer portion 13r further comprises at least one restraint portion. The outer portion 13r is prevented from deforming toward the engagement piece members 13 when molding the body part 12 of the denture base 10, thereby restraining the allowance portion 15 from being compressed by pressure when molding the body part 12 (FIG. 50) of the denture base 10.

Figure 59A:
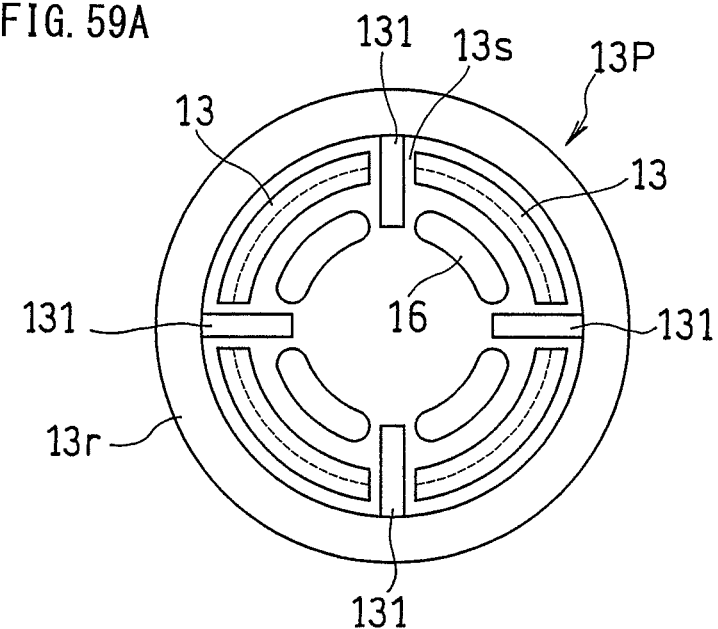
FIG. 59A is a plan view showing another example of an engagement piece.
Figure 59B:
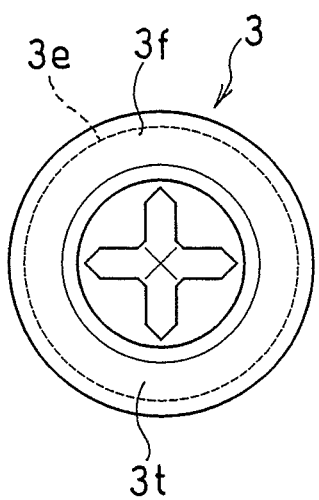
FIG. 59B is a plan view showing an abutment.
Figure 59C:
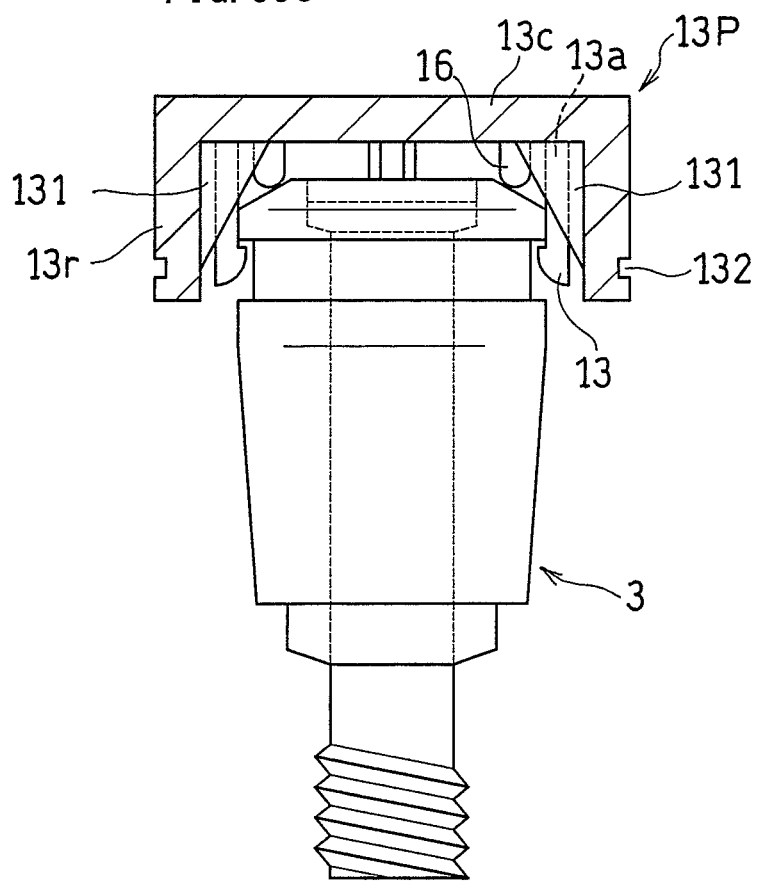
FIG. 59C is a partially sectioned front view showing the engagement piece and the abutment.

In the embodiments of FIG. 59A to FIG. 59C, the restraint portion is formed by the rib 131 restraining the outer portion 13r from falling (coming) toward the engagement piece member 13. The rib 131 is provided at a corner formed by the lid portion 13c and the outer portion 13r in the slit 13s.

Figure 60A:
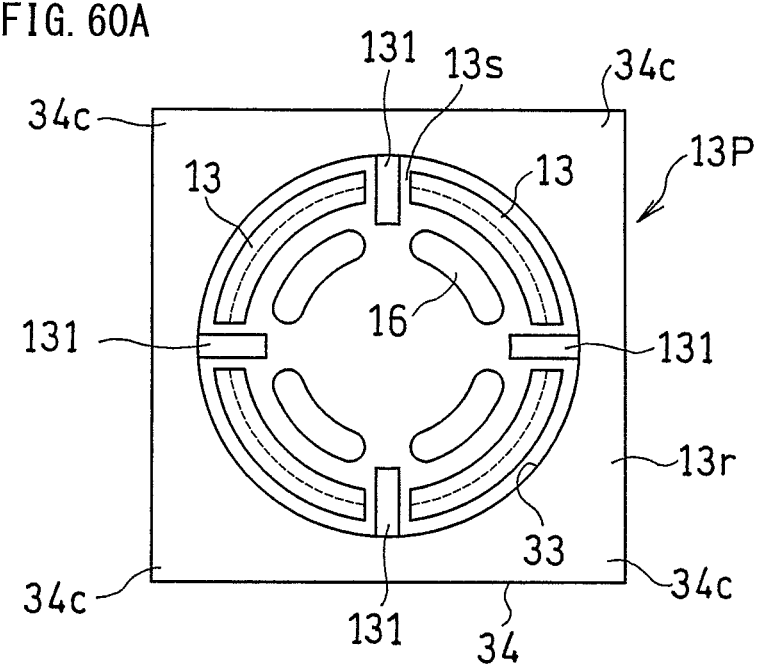
FIG. 60A is a plan view showing further another example of an engagement piece.
Figure 60B:
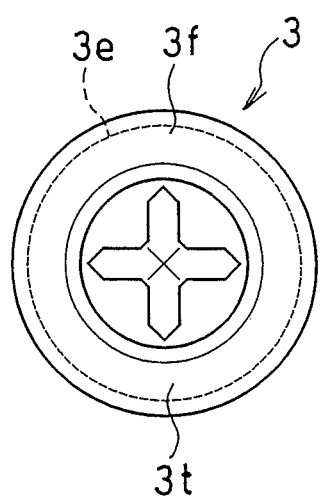
FIG. 60B is a plan view showing an abutment, FIG. 60C showing a partially sectioned front view showing the engagement piece and the abutment.
Figure 60C:
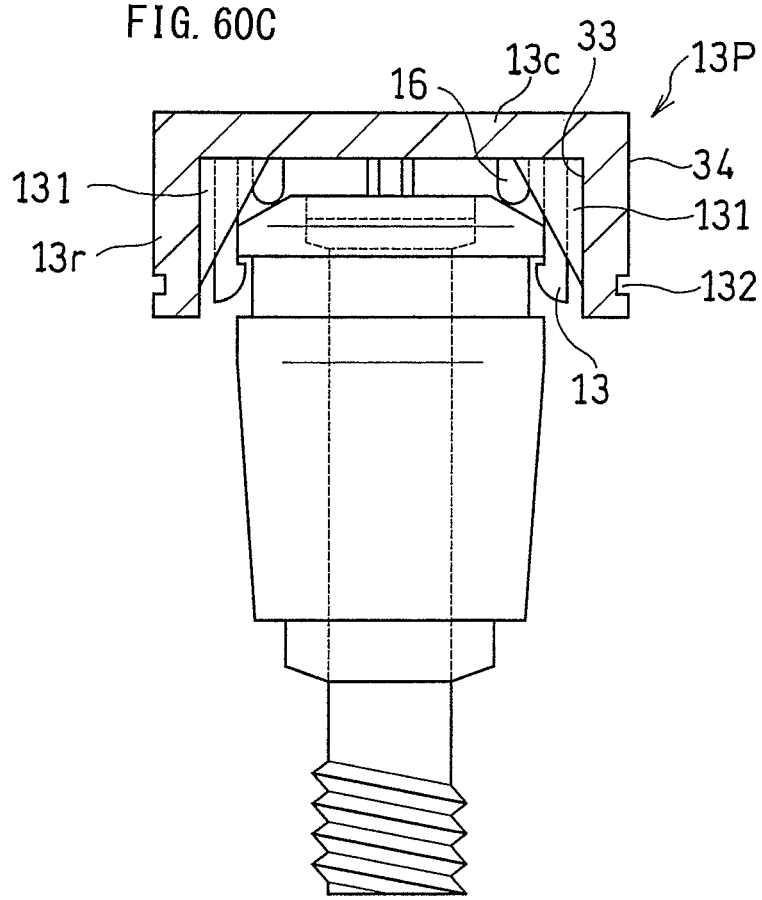
Figure 61A:
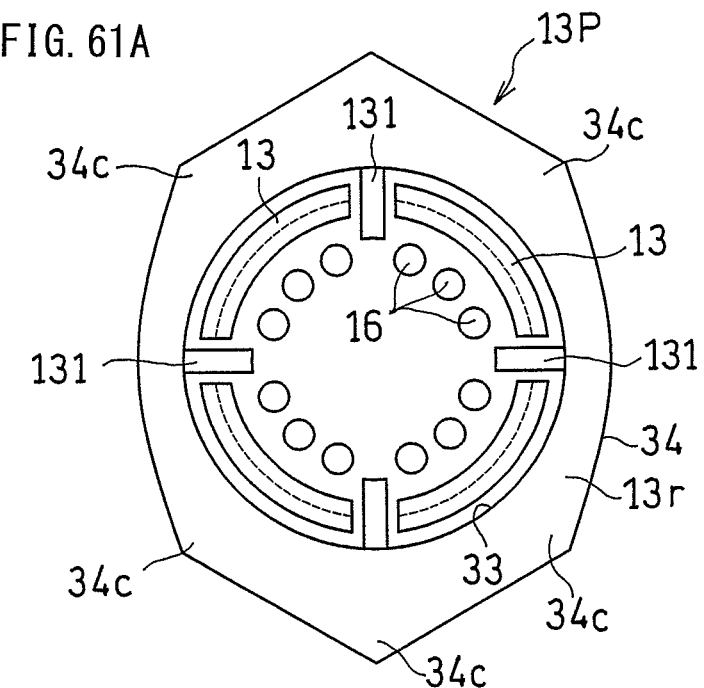
FIG. 61A is a plan view showing another example of an engagement piece.
Figure 61B:
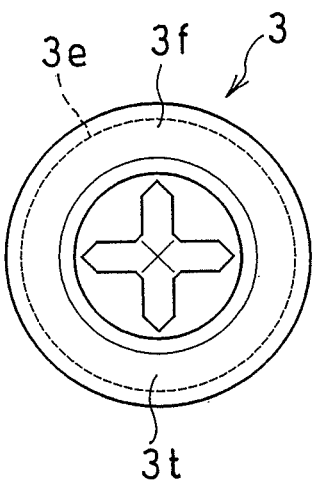
FIG. 61B is a plan view showing an abutment, FIG. 61C showing a partially sectioned front view showing the engagement piece and the abutment.
Figure 61C:
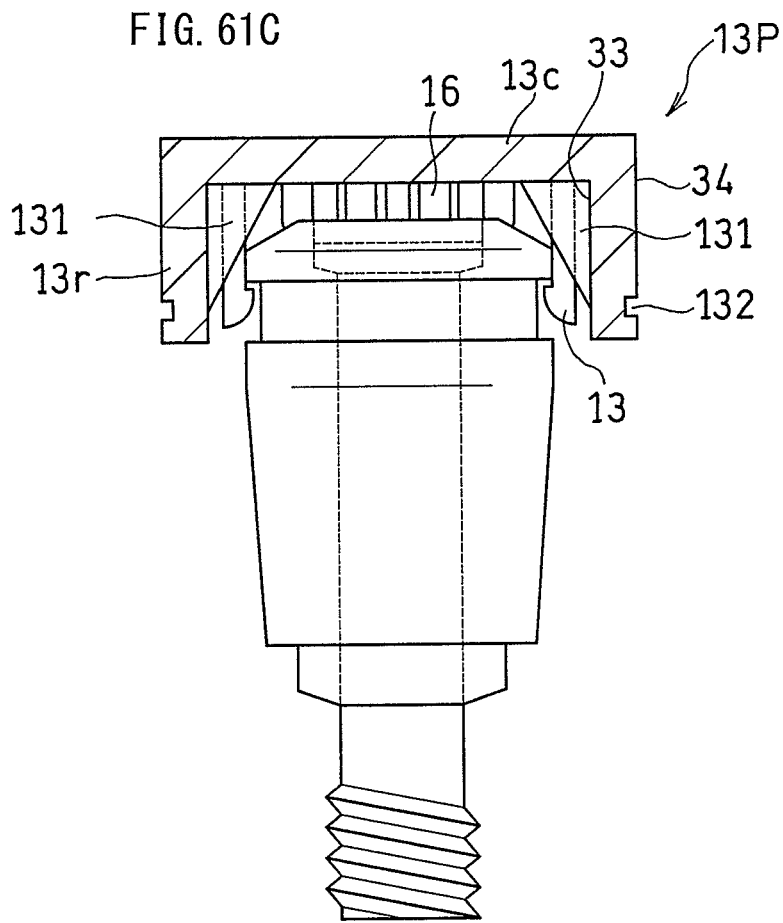

In the engagement piece 13P of FIG. 60A and FIG. 61A, the shape of the third surface 33 of the outer portion 13r is round shape in a plane section, and the shape of the fourth surface 34, opposite to the third surface 33, of the outer portion 13r is quadrangle shape or hexagonal shape in a plane section. Each corner 34c of the quadrangle shape or hexagonal shape forms the restraint portion.

Note that, in FIG. 61A, a plurality of pins are provided in a circumference as the cushion portions 16.

FIG. 62A to FIG. 64B is still another embodiment.

FIG. 62B shows the engagement piece 13P and the tubular member R1. The tubular member R1 comprises: the base 101 that covers the circumference of the engagement piece member 13 and is to be the allowance portion; and the skirt 102 protruding from the base 101 in the axis direction of the tubular member R1. The engagement piece 13P of this embodiment has a similar structure to the engagement piece 13P of FIG. 58D and FIG. 58E. The difference between the structure of the engagement piece 13P of FIG. 62C to FIG. 62D and that of FIG. 58D to FIG. 58E is that the engagement piece 13P of FIG. 62C to FIG. 62D is provided with the continuous portion 13P1 in which the upper parts of the engagement piece members 13 are cylindrically continuous with each other. Note that the tubular member R1 does not melt by molding heat as well as has the strength enabling the member R1 not to be depressed by pressure when molding.

In this embodiment, the denture 1 is produced in accordance with the following process.

As with the description above, after the process of FIG. 52A, FIG. 52B and FIG. 53A, as shown in FIG. 62A, the male mold 51 in which the replica 3R protrudes from the plaster is produced. Exposed part of the replica 3R has the same shape as the abutment 3 of FIG. 50.

On the other hand, the tubular member R1 is externally inserted into around the engagement piece members 13 of the engagement piece 13P. On this occasion, the state that the tubular member R1 is held on the engagement piece members 13 is maintained because of elasticity of resin of the engagement piece members 13.

Figure 63A:
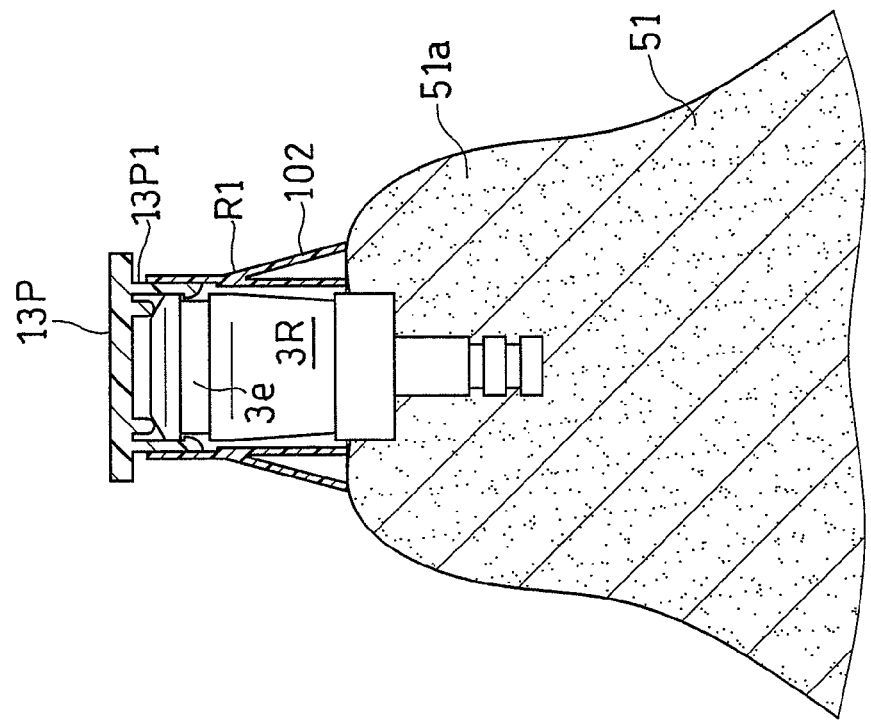
FIG. 63A and FIG. 63B are cross sectional views each showing another example of process in a method for producing a denture.
Figure 63B:
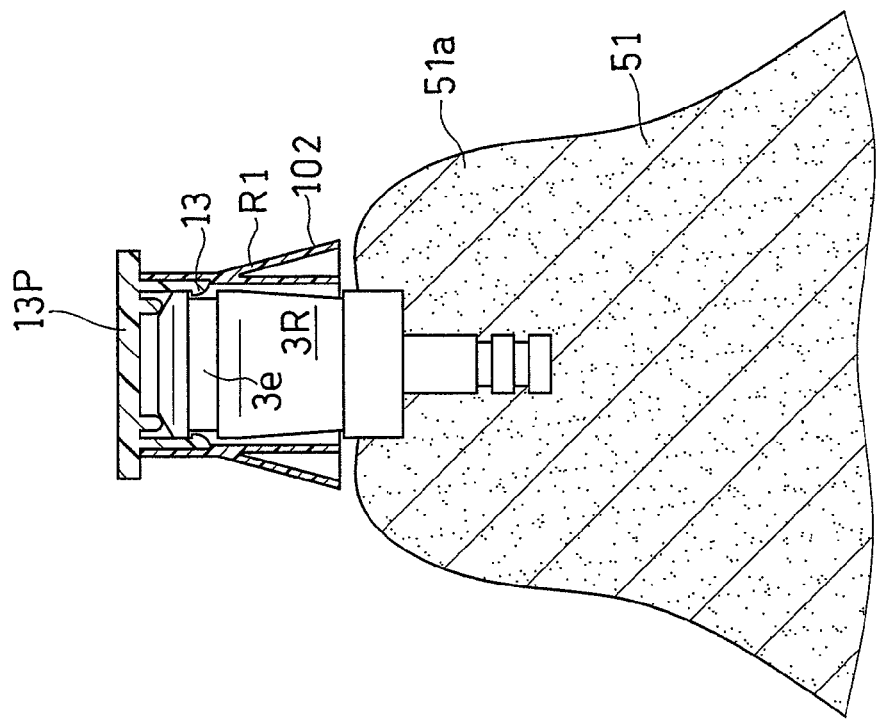

Next, as shown in FIG. 63A, the engagement piece 13P is fitted to the replica 3R. In the piece 13P, the tubular member R1 of FIG. 62B is externally fitted to the male mold 51 of FIG. 62A. Thereby, the engagement element 13e of the engagement piece 13P is engaged with the groove 3e of the replica 3R.

Note the height of the tubular member R1 is set so that the lower end of the skirt 102 closes to the plaster of the male mold 51.

After the external engagement described above, as shown FIG. 63B, the tubular member R1 is moved in the axis direction of the replica 3R so that the lower end of the skirt 102 contacts the plaster. Note that although a slight (tiny) gap is formed between the skirt 102 and the plaster, the gap is filled with plaster (not shown).

Figure 64A:
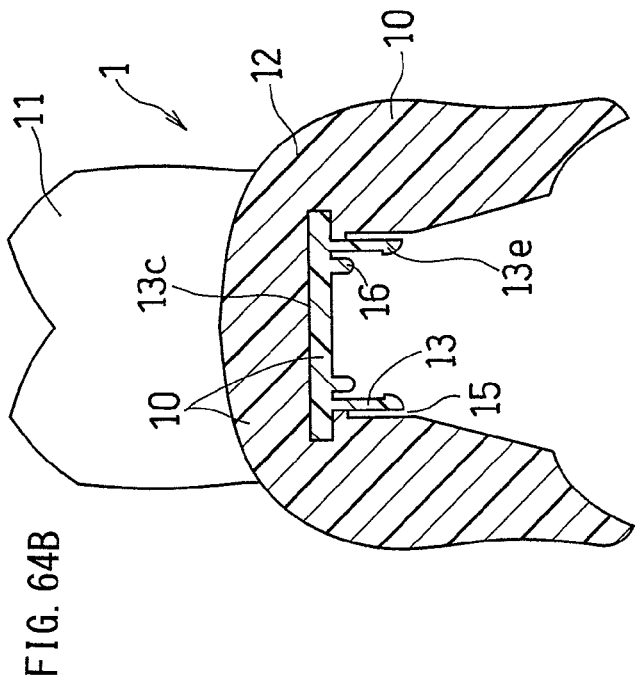
FIG. 64A and FIG. 64B are cross sectional views each showing the process in the method for producing a denture.

Molten resin made of nylon containing 0.10 to 0.20 weight percent of pigment is injected into between the male mold 51 and a well-known female mold (not shown) of a denture 1, thereby molding the resin body part 12 of the denture base 10 of FIG. 64A as well as producing the denture base 10 in which the engagement piece 13P is integral with the body part 12 of the denture base 10. After the body part 12 is hardened, the plaster of the male mold 51 and the tubular member R1 are removed.

Figure 64B:
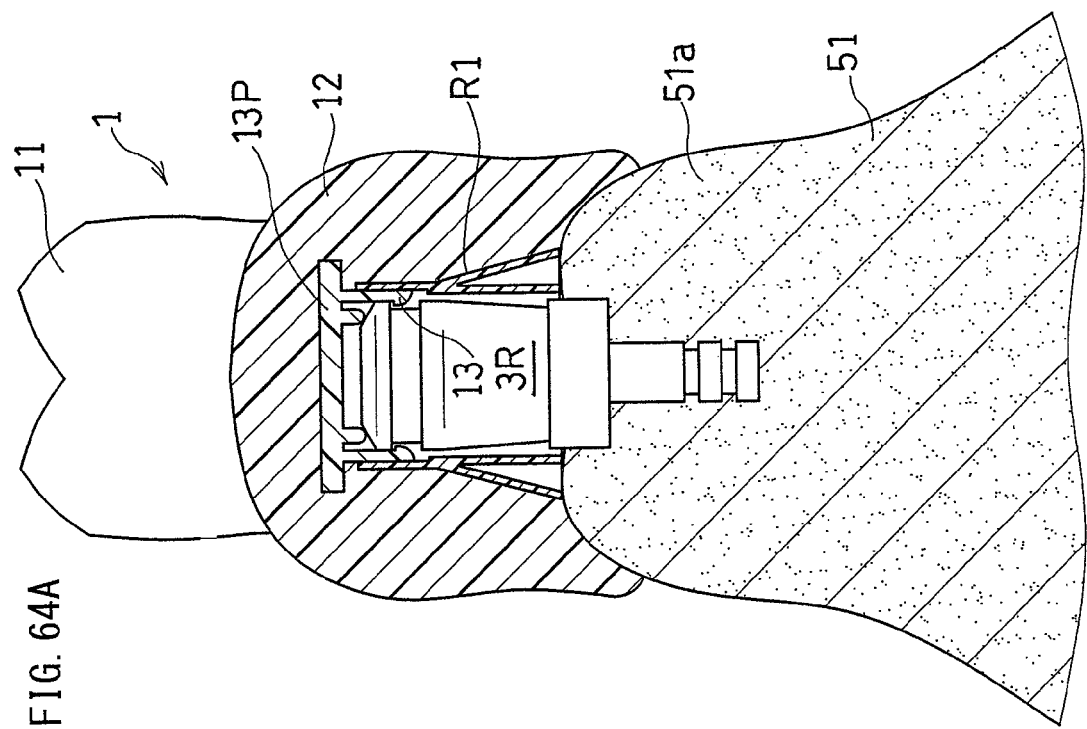

Thus, the denture 1 having the allowance portion 15 of FIG. 64B is produced.

FIG. 65A to FIG. 66B show still another embodiment.

FIG. 65B shows the engagement piece 13P and the tubular member R1. In this embodiment, the skirt 102 is slidable in the up-down direction with respect to the base 101 of the tubular member R1. Furthermore, an end of the skirt 102 contacting the plaster may be in wave shape so that it becomes easy for the end to be along oral shapes of many patients.

In this embodiment, the tubular part R1 may be formed of metallic pipe such as copper pipe and steel pipe. Note that, in this embodiment, the continuous portion 13P1 of FIG. 62C is not provided. The other structure is the same as the embodiment of FIG. 62B to FIG. 62D.

In this embodiment, the denture 1 is produced in accordance with the process described as follows.

As with the description above, after the processes of FIG. 52A, FIG. 52B, and FIG. 53A, as shown in FIG. 65A, the male mold 51 in which the replica 3R protrudes from the plaster part 51a is produced.

On the other hand, the tubular member R1 is externally inserted into around the engagement piece members 13 of the engagement piece 13P. On this occasion, the state that the tubular member R1 is hold on the engagement piece members 13 is maintained because of elasticity of resin of the engagement piece members 13.

Next, the engagement piece 13P is fitted to the replica 3R, as shown in FIG. 66A, with the tubular member R1 of FIG. 65B externally fit to the male mold 51 of FIG. 65A. Thereby, the engagement element 13e of the engagement piece 13P is engaged with the groove 3e of the replica 3R.

On this occasion, the skirt 102 slides with respect to the base 101 in the axis direction of the replica 3R, and then the tip of the skirt 102 contacts with the plaster part 51a of the male mold 51. Thereafter, a gap formed between the skirt 102 and the plaster 51a is filled with plaster (not shown).

Note that the base 101 and the skirt 102 are fixed with each other by adhesive or sticker.

Molten resin made of nylon containing 0.10 to 0.20 weight percent of pigment is injected into between the male mold 51 and a well-known female mold (not shown) of a denture 1, thereby molding the resin body part 12 of the denture base 10 of FIG. 66B as well as producing the denture base 10 in which the engagement piece 13P is integral with the body part 12 of the denture base 10. After the body part 12 is hardened, the plaster part 51a of the male mold 51 and the tubular member R1 are removed.

Thus, the denture 1 having the allowance portion 15 of FIG. 66B is produced.

In the embodiment of FIG. 62A to FIG. 66B, the number of process remarkably decreases, and thereby work forming the allowance portion 15 by a dental technician becomes more simple and easier.

Note that, in the embodiment of FIG. 65A to FIG. 66B, the engagement piece 13P of FIG. 51A to FIG. 51C or FIG. 58D to FIG. 58E may be employed.

While preferred embodiments have been described above with reference to the drawings, various obvious changes and modifications will readily occur to those skilled in the art upon reading the present specification.

For example, the cushion portion may not be provided.

The denture 1 may be a partial denture.

The following structure may be employed: a depressed portion as an engagement element 13e is formed in an engagement piece member 13, and a ridge as an engaged groove 3e is formed in an abutment 3.

Therefore, such changes and modifications shall be deemed to fall within the scope of the present invention.

Industrial Applicability

The present invention can be applied to dental treatment.

Reference Signs List

1: Denture, 10: Denture base, 10c: Accommodating depressed portion, 10g: Anchor groove, 10h: Deep hole, 11: Artificial tooth, 12: Main Body 13: Engagement piece member, 13a: End portion, 13c: Lid portion, 13d: Restraint portion, 13e: Engagement element, 13g: Anchor groove, 13p: Engagement piece, 13s: Slit, 130: Cylindrical area, 131: rib, 132: engagement depressed portion, 139: flange 14: Fitting hole, 14A: Hole 15: Allowance portion (groove), 15A: Groove, 15P: Projecting portion 16: Cushion portion, 16K: Cushion, 17A: Hole 18: Buried material 19: Coupling layer, 19R: Engagement ring, 19s: Gap 2: Fixture, 20: Window, 21, 21A: Tray, 22: Guide pin, 23: Impression material 3: Abutment, 3L: Axis, 3R: Replica, 3e: Engaged groove, 3f: Tapered surface, 3g: Longitudinal groove, 3h: Through hole, 3s: Male screw portion, 3t: Top portion (top), 3p: Projection (ridge), 39: Cylindrical outer circumferential surface 301 to 304: Abutment, 301s to 304s: Axial line 31: First surface, 32: Second surface, 33: Third surface, 34: fourth surface, 34c: corner 4: Oral tissue, 40: Gum, 41: Alveolar bone 50: Female mold, 51: Male mold, 51a: Plaster part, 51b: Area corresponding to abutment, 51g: Longitudinal groove, 52: Matrix, 53: Filler, 54: Resin mold, 55: Model, 56: Plaster mold, 56A: Plaster mold, 519: Corresponding area, 500: depressed portion 60: Replica, 61: First replica, 62: Second replica 70: First core, 70D: Divided cores, 70e: End face, 71: First part, 71A: Blade portion, 72: Second part, 72A: Cylindrical portion, 73: Blade, 79: Positioning portion 80: Second core, 81: Portion, 90: Core θ: Center angle, S: Gap X: Horizontal direction, X1: Left-right direction, Y: Front-back direction, Z: Vertical direction (Up-down direction)

The invention claimed is:

1. A denture system comprising: a plurality of abutments each having a surface to be exposed in an oral cavity; and a denture to be detachably attached to the abutments,
the denture including a body part of a denture base, the denture base formed by a resin and to be in contact with a gum; an artificial tooth supported by the body part of the denture base; and a plurality of engagement pieces for engaging the body part of the denture base to the abutments, the engagement pieces formed by a nylon-based thermoplastic resin and integral with the denture base, wherein each engagement piece of the plurality of the engagement pieces includes:
a lid portion to cover an entire surface of a top of each of the abutments and to be covered by the body part of the denture base, and
a plurality of engagement piece members extending from the lid portion in an up-down direction, wherein the engagement piece members elastically deform to spread around each end portion thereof in the up-down direction when attaching and detaching the denture, engage with each of the abutments when worn, and are divided from one another in a circumferential direction,
wherein each of the engagement piece members has a first surface to be in contact with an outer circumferential surface of each of the abutments and has a second surface opposite to the first surface, and the first surfaces of the engagement piece members define a fitting hole to be detachably fitted over the outer circumferential surface of each of the abutments,
the lid portion closes one end, in the up-down direction, of the fitting hole defined by the engagement piece members,
the lid portion and the top of the abutment define a space therebetween allowing the artificial tooth to be replaced with respect to the gum,
each of the engagement pieces further comprises an outer portion extending in the up-down direction from a circumference of the lid portion and facing the engagement piece members, the outer portion has a third surface being further from an axis of each of the abutments than the second surfaces of the engagement piece members, and the outer portion is joined to the body part of the denture base and is non-contact with each of the abutments, and the outer portion and the engagement piece members are formed by the nylon-based thermoplastic resin,
an allowance portion is defined between the second surfaces and the third surface of the outer portion and allows the engagement piece members to be elastically deformed to spread in a direction from the first surface toward the second surface, and
the lid portion closes one end, in the up-down direction, of the fitting hold defined by the engagement piece members and the one end, in the up-down direction, of the allowance portion.

2. The denture system according to claim 1, wherein:
the outer portion of each of the engagement pieces extends in the up-down direction from an outer circumference of the lid portion and is formed in tubular shape, and an inner circumferential surface of the tubular outer portion defines the third surface.

3. The denture system according to claim 1, wherein:
a plurality of protruding portions are integrally formed in the lid portion and divided from one another in a circumferential direction, and each of the protruding portions projects from the lid portion toward each of the abutments in the fitting hole surrounded by the plurarity of engagement piece members and contacts with an outer circumferential edge of the top of each of the abutments.

4. The denture system according to claim 1, wherein:
a ratio of a pigment to a resin forming the engagement piece is set to be from 0 weight percent to 0.07 weight percent.

5. The denture system according to claim 1, wherein a ratio of a pigment contained in a resin forming the engagement piece is smaller than a ratio of a pigment contained in a resin forming the body part.

6. A manufacturing method of the denture system of claim 1, comprising:
a step of coupling the resin to be the denture base to the lid portion and the outer portion of each of the engagement pieces while the allowance portion of each of the engagement pieces is maintained.

* * * * *